US008906952B2

(12) United States Patent
Lee et al.

(10) Patent No.: US 8,906,952 B2
(45) Date of Patent: Dec. 9, 2014

(54) INDOLE DERIVATIVE OR PHARMACEUTICALLY ACCEPTABLE SALT THEREOF, PREPARATION METHOD THEREOF, AND PHARMACEUTICAL COMPOSITION FOR PREVENTING OR TREATING METABOLIC DISEASES CONTAINING SAME AS ACTIVE INGREDIENT

(71) Applicant: Korea Research Institute of Bioscience and Biotechnology, Daejeon (KR)

(72) Inventors: Hyun Sun Lee, Daejeon (KR); Mun-Ock Kim, Daejeon (KR); Yongseok Choi, Seoul (KR); Kyeong Lee, Seoul (KR); Jeong-Jun Park, Daejeon (KR); Jee-Hee Seo, Daejeon (KR); Hwayoung Jung, Gyeongsangbuk-do (KR); Sungchan Cho, Daejeon (KR)

(73) Assignee: Korea Research Institute of Bioscience & Biotechnology, Daejeon (KR)

( * ) Notice: Subject to any disclaimer, the term of this patent is extended or adjusted under 35 U.S.C. 154(b) by 0 days.

(21) Appl. No.: 14/070,683

(22) Filed: Nov. 4, 2013

(65) Prior Publication Data
US 2014/0057909 A1 Feb. 27, 2014

Related U.S. Application Data

(63) Continuation-in-part of application No. PCT/KR2012/003308, filed on Apr. 27, 2012.

(30) Foreign Application Priority Data

May 3, 2011 (KR) .................... 10-2011-0042124
Apr. 27, 2012 (KR) .................... 10-2012-0044527

(51) Int. Cl.
| C07D 209/12 | (2006.01) |
| C07D 209/14 | (2006.01) |
| C07D 401/12 | (2006.01) |
| C07D 209/20 | (2006.01) |
| C07D 295/155 | (2006.01) |
| C07D 209/26 | (2006.01) |

(52) U.S. Cl.
CPC ............ *C07D 401/12* (2013.01); *C07D 209/20* (2013.01); *C07D 295/155* (2013.01); *C07D 209/12* (2013.01); *C07D 209/14* (2013.01); *C07D 209/26* (2013.01)
USPC .......................................... 514/415; 548/495

(58) Field of Classification Search
CPC ........................ C07D 209/12; C07D 209/14
USPC ................................................. 548/495
See application file for complete search history.

(56) References Cited

U.S. PATENT DOCUMENTS

| 5,245,046 A | 9/1993 | Youngdale et al. |
| 6,432,682 B1 | 8/2002 | Omura et al. |
| 6,608,185 B1 | 8/2003 | Omura et al. |
| 7,902,190 B2 | 3/2011 | Lee et al. |

FOREIGN PATENT DOCUMENTS

| JP | 52139855 A | 10/1992 |
| JP | 2001122855 A | 5/2001 |
| KR | 100460438 B1 | 6/2003 |
| KR | 100577320 B1 | 4/2004 |
| KR | 100807718 B1 | 2/2008 |
| KR | 1020100070664 A | 6/2010 |
| WO | 2006004200 A | 1/2006 |
| WO | 2006019020 A | 2/2006 |
| WO | 2006044775 A | 4/2006 |

OTHER PUBLICATIONS

Diabetes [online]. Retrieved from the internet on Mar. 10, 2014. URL; http://www.mayoclinic.org/diseases-conditions/diabetes/basics/definition/con-20033091.*
Chen et al., "DGAT and Triglyceride Synthesis: A New Target for Obesity Treatment?", Trends. Cardiovasc. Med., 10, 188-192, 2000.
Chen et al., "Analysis of energy expenditure at different ambient temperatures in mice lacking DGAT1", Am J Physiol Endocrinol Metab, 284, E213-E218, 2003.
Chen et al., "Dissociation of Obesity and Impaired Glucose Disposal in Mice Overexpressing Acyl Coenzyme A: Diacylglycerol Acyltransferase 1 in White Adipose Tissue", Diabetes, 51, 3189-3195, 2002.
Chen et al., "Increased insulin and leptin sensitivity in mice lacking acyl CoA: diacylglycerol acyltransferase 1", Journal of Clinical Investigation, 109, 1049-1055, 2002.
Chen et al., "Obesity resistance and enhanced glucose metabolismin mice transplanted with white adipose tissue lacking acyl CoA: diacylglycerol acyltransferase 1", Journal of Clinical Investigation, 111, 1715-1722, 2003.
Farese et al., "Triglyceride synthesis: insights from the cloning of diacylglycerol acyltransferase", Current Opinion in Lipidology, 11, 229-234, 2000.

(Continued)

*Primary Examiner* — Shawquia Young
(74) *Attorney, Agent, or Firm* — Cheryl H. Agris; Agris & van Natzmer, LLP

(57) ABSTRACT

The present invention relates to an indole derivative, The indole derivative according to the present invention effectively inhibits the activity of diacylglycerol acyltransferase (DGAT) which induces metabolic diseases, such as obesity, diabetes, hyperlipidemia, or fatty liver and the like in lipid metabolism, thereby effectively regulating lipid metabolism and energy metabolism, and thus can be useful in pharmaceutical compositions for preventing or treating metabolic disease.

11 Claims, No Drawings

(56) References Cited

OTHER PUBLICATIONS

Ganji et al., "Niacin noncompetitively inhibits DGAT2 but not DGAT1 activity in HepG2 cells." Journal of Lipid Research, 45, 1835-1845, 2004.

Ko et al., "Inhibitory activity of diacylglycerol acyltransferase by tanshinones from the root of *Salvia miltiorrhiza*", Archives of Pharm. Research, 25, 446-448, 2002.

Lee et al., "Inhibitory Activity of Diacylglycerol Acyltransferase by Cochlioquinones A and A1", Journal of Antibiotics, 56, 967-969, 2003.

Lee et al., "New polyacetylenes, DGAT inhibitors from the roots of *Panax ginseng*", Planta Medica, 70, 197-200, 2004.

Yoganathan et al. "Cochlioquinones and Epi-Cochlioquinones: Antagonists of the Human Chemokine Receptor CCR5 from *Bipolaris brizae* and *Stachybotrys chartarum*", J. Antibiot., 57, 59-63, 2004.

* cited by examiner

INDOLE DERIVATIVE OR PHARMACEUTICALLY ACCEPTABLE SALT THEREOF, PREPARATION METHOD THEREOF, AND PHARMACEUTICAL COMPOSITION FOR PREVENTING OR TREATING METABOLIC DISEASES CONTAINING SAME AS ACTIVE INGREDIENT

TECHNICAL FIELD

The present invention relates to novel indole derivatives or pharmaceutically acceptable salts thereof, a preparation method thereof, or pharmaceutical composition for preventing or treating metabolic diseases such as obesity, diabetes, hyperlipidemia, or fatty liver comprising the pharmaceutically acceptable salts thereof as active ingredients.

BACKGROUND ART

Acyl CoA or diacylglycerol acyltransferase ("DGAT") is the enzyme that catalyzes the last stage of the glyceryl 3-phosphate path, and plays a role of synthesizing triglycerides using 1,2-diacylglycerol and fatty acyl CoA as a substrate. For the biosynthesis of triglycerides, glycerol 3-phosphate path (liver and adipose tissue, etc.), and the monoacylglycerol (intestinal epithelial cells of the small intestine) are used.

Recently, Gladstone Institute of Cardiovascular Diseases in USA reported evidence that according to DGAT function researche using the DGAT-1 deficient mouse, the DGAT-1 deficient mouse had effectively inhibited diet-induced obesity by administration of a high fat diet, and increased sensitivity to insulin and leptin, thus indicating improved glucose metabolism. The follow-up researche reported that in insulin-sensitive tissues like fat tissues, skeletal muscles, liver, and pancreatic beta cells, selective inhibition of DGAT, which is the catalytic enzyme of the biosynthesis process of triglycerides, was effective in the prevention and treatment of obesity and type 2 diabetes (Chen H C, et al., Trends Cardiovasc. Med., 10, 188-192, 2000; Farese Jr. et al., Curr. Opin. Lipidol., 11, 229-234, 2000; A. Subauste et. al., Current Drug Target-Immun, Endocrine & Metabol Disorders, 3, 263-270, 2003; Y. Yu et. al. Anals of Medicine, 36, 252-261).

When the activity of DGAT is inhibited, the enzyme catalytic reaction of DGAT for the synthesis of triglycerides is blocked or has reduced synthetic reaction efficiency. By inhibiting biosynthesis of the triglycerides via the inhibition of DGAT which is the final stage in the triglyceride synthesis, accumulation of fat in the fat cells decrease with the size of the fatty cells reduced, and energy consumption increased due to increasing momentum, coupled with the increased expression of the uncoupling protein, and accordingly, high fat-induced weight gains are suppressed. (Smith SJ. et al., Nature Genetics, 25, 87-90, 2000; Chen et al., J Clin Invest., 109 (8), 1049-1055, 2002; Chen et al., J Clin Invest., 111, 1715-1722, 2003; Chen et al. Am. J. Physiol. Endocrono I. Metab., 284, E213-218, 2003).

In addition, DGAT inhibition is known to bring about improved insulin resistance (IR), by suppressing fat accumulation in skeletal muscle, liver, pancreas and other non-adipose tissue.

That is, in response to stimuli by insulin, cells have reduced inhibitory phosphorylation at the serine site of insulin receptor substrate-1 (IRS-1) and increased phosphorylation at the tyrosine sites, thus have increased number of GLUT-4, the sugar transporter, via the activation of insulin signaling along phosphatidylinositol-3 kinase (PI-3K), protein kinase B, Akt (PKB), protein kinase C (PK0), etc.

With the inhibition of DGAT activity in the cells, activities of PI-3K, PKB, and PKC increases, thus causing increased number of GLUT-4 ectocytosized to the membrane, and finally increasing the number of cells introduced into cells. That is, DGAT inhibition increases sensitivity to insulin (Chen et al., Arterioscler Thromb Vase Biol. 25 (3), 482-486, 2005; Chen et al., J Clin Invest. 111 (11), 1715-22, 2003; Chen et al., J Clin Invest. 109 (8), 1049-1055, 2002; Chen et al., Diabetes. 51 (11), 3189-3195, 2002; Subauste and bur ant., Curr Drug Targets Immune Endocr Metabol Disord. 3 (4), 263-270, 2003). As the direct linkage between DGAT inhibition and overcoming insulin resistance is elucidated, it is also understood that the DGAT inhibition can be applicable as a treatment target for type 2 diabetes, the abnormal condition caused due to insulin resistance that blocks glucose absorption, even with normal insulin secretion.

The known compounds as the DGAT enzyme inhibitors include biphenyl-4-yl-carbonyl-amino acid derivatives (WO2006044775, Bayer Pharmaceuticals Corp), urea derivatives (WO2006019020, WO2006004200, Sankyo Co), pyrrole carboxylic acid derivatives (JP05213985A, Mitsubishi Kasei Corp, Japan), and phosphonic acid ester derivative (JP2004067635A—Otsuka Pharmaceut Factory INC, Japan), etc. On the other hand, DGAT enzyme inhibitors from natural products of ginseng polyacetylenes (Korea Patent No. 0460438, Lee et al. Planta Med. 70, 179-200, 2004), quinolone alkaloid, tanshinones, prenyl flavonoids) isolated from evodia, salvia, and saphora (Korea Patent No. 0577320, Ko et al., Arch. Phar. Res. 25, 446-448, 2002, Korea Patent No. 0507989).

In addition, the Omura research group of the Kitasato Institute (Japan) reported inhibitor such as roselipins (U.S. Pat. No. 6,432,682 (2002), U. S. Pat. No. 6,608,185 (2003)), cochlioqui none A and Al, I. Antibiot., 56,: 967, 2003; J. Antibiot., 57, 59, 2004), amidepsines and xanthohumols, and eicosapentaenoic acid, 2-bromooctanoate, and niacin (Rustan et al., J. Lipid. Res., 29, 1417-1426, 1988, Ganji et al. J. Lipid. Res., 45, 1835-1845).

Objects

It is an object of the present invention to provide novel indole derivative or a pharmaceutically acceptable salt thereof.

It is another object of the present invention to provide a method for preparing the indole derivatives.

It is yet another object of the present invention to provide a pharmaceutical composition for preventing or treating metabolic disease such as obesity, diabetes, hyperlipidemia, and fatty liver comprising the indole derivatives or pharmaceutically acceptable salt thereof.

It is yet another object of the present invention to provide a composition for health food for preventing or improving metabolic disease including obesity, diabetes, hyperlipidemia, and fatty liver, comprising the indole derivative or pharmaceutically acceptable salt thereof.

It is yet another object of the present invention to provide an inhibitor to diacylglycerol acyl transferase (DGAT) activity, comprising the indole derivatives or pharmaceutically acceptable salts thereof.

BRIEF SUMMARY

To achieve the above objects, the present invention provides indole derivative represented by Formula 1 below or a pharmaceutically acceptable salt thereof:

[Formula 1]

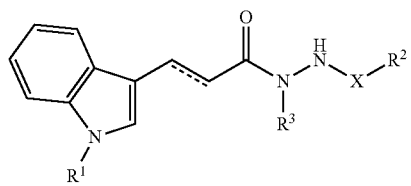

In Formula 1, $R^1$ is —H, $C_{1-10}$ linear or branched alkyl group, $C_{2-10}$ linear or branched alkenyl group, $C_{3-12}$ cycloalkyl group, $C_{3-12}$ cycloalkyl $C_{1-5}$ alkyl group, $C_{5-12}$ aryl group, $C_{5-12}$ aryl $C_{1-5}$ alkyl group, $C_{5-12}$ aryl carbonyl group, $C_{1-10}$ linear or branched alkyl carbonyl group or $C_{1-10}$ linear or branched alkoxy carbonyl group;

$R^2$ is $C_{5-12}$ aryl group or $C_{5-12}$ heteroaryl group including one or more of N, O and S in a ring, in which the aryl group or heteroaryl group is non-substituted or substituted with —OH, $C_{1-10}$ linear or branched alkyl group, halogen or

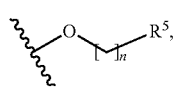

$R^5$ is —H, —OH, —$NH_2$, carboxyl group, amino carbonyl group, $C_{1-10}$ linear or branched alkyl group, $C_{1-5}$ linear or branched alkoxy group, $C_{1-10}$ linear or branched alkoxy carbonyl group or $C_{5-12}$ heterocycloalkyl group including one or more of N, O and S in a ring, n is an integer between 0-5;

$R^3$ is —H or $C_{1-5}$ linear or branched alkyl group;

$R^4$ is —H, $C_{1-5}$ linear or branched alkyl group or halogen;

X is carbonyl group or sulfonyl group; and

===== is single or double bond.

In addition, the present invention provides a preparation method of indole derivative represented by Formula 1, as represented by Reaction Formulae 1, 2, 3 or 4.

[Reaction Formula 1]

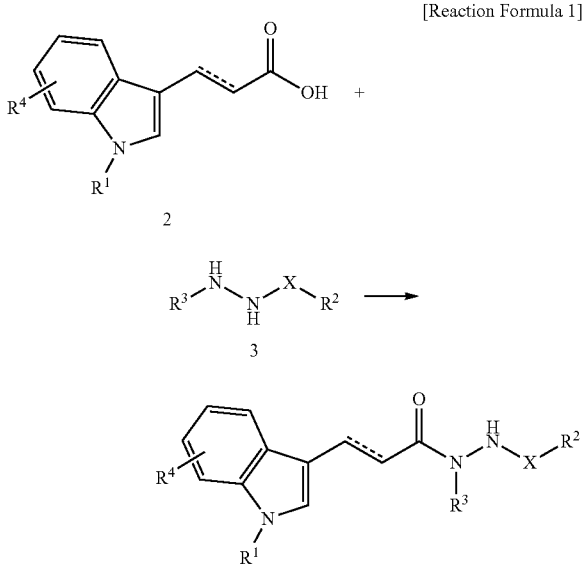

where, $R^1$, $R^2$, $R^3$, $R^4$, X and ===== are as defined herein.

[Reaction Formula 2]

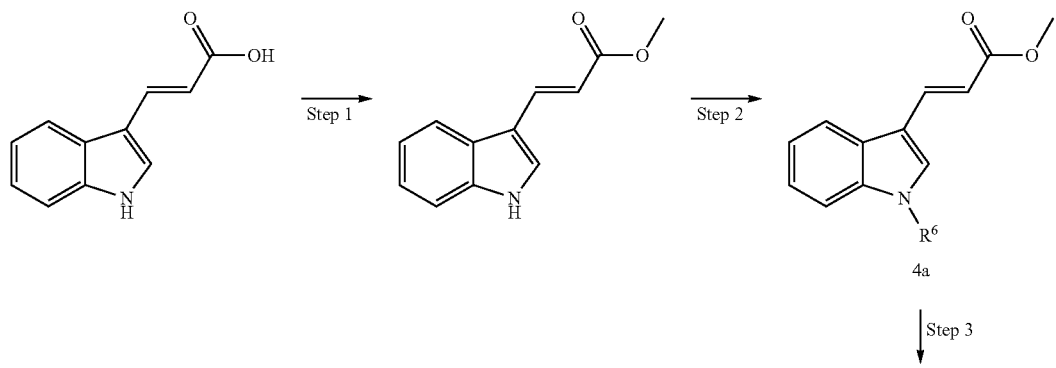

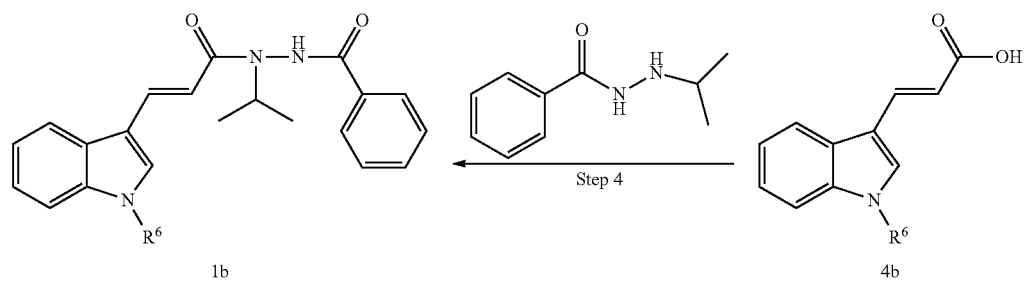

where, $R^6$ is as defined herein.

[Reaction Formula 3]
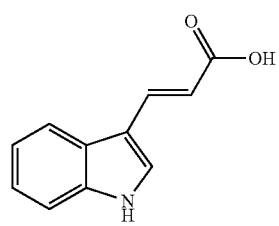
+
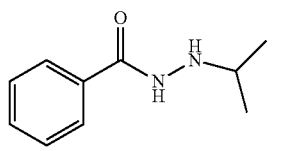 →Step 1→
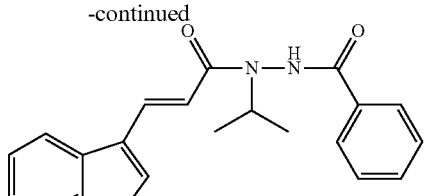
↓ Step 2
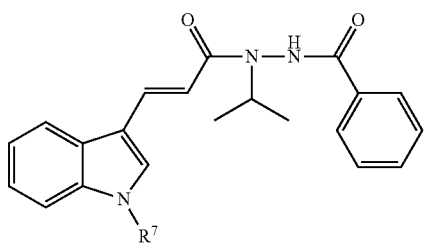
1c
where, R⁷ is as defined herein.
[Reaction Formula 4]
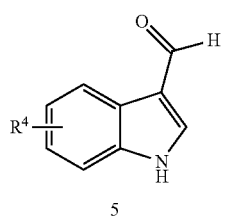 →Step 1→ 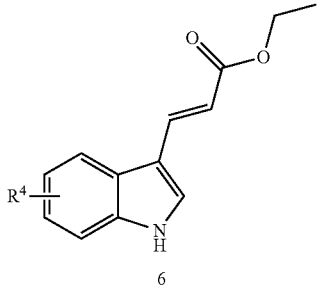 →Step 2→ 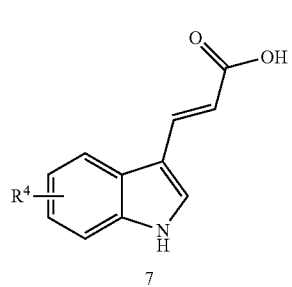
5          6          7
↓ Step 3
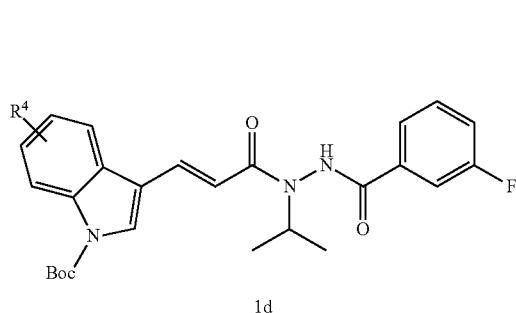 ←Step 4, 3a← 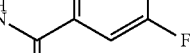 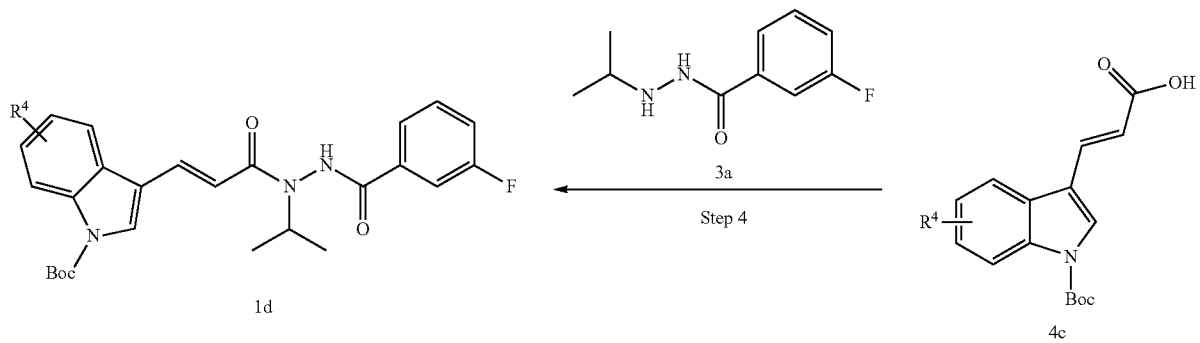
1d          4c
where, R⁴ and Boc are as defined herein.

Furthermore, the present invention provides a composition, particularly a pharmaceutical composition for preventing or treating metabolic disease including obesity, diabetes, hyperlipidemia, and fatty liver, comprising the indole derivative represented by Formula 1 or pharmaceutically acceptable salt thereof.

In addition, the present invention provides a composition for health food for preventing or improving metabolic disease including obesity, diabetes, or fatty liver, comprising indole derivative represented by Formula 1 or pharmaceutically acceptable salt thereof as active ingredient.

Also provided is a method for preventing or treating metabolic disease in a patient in need thereof comprising administering to said patient an amount of the indole derivative or represented by Formula 1 or pharmaceutically active salt thereof or said compositions effective to prevent or treat said metabolic disease.

Furthermore, the present invention provides an inhibitor to diacylglycerol acyl transferase (DGAT) activity, comprising the indole derivatives or pharmaceutically acceptable salts thereof.

The indole derivative represented by Formula 1 effectively inhibits activity of diacylglycerol acyltransferase (DGAT) which causes metabolic diseases in the process of the lipid metabolism and effectively regulate the lipid metabolism and energy metabolism, and thus can be advantageously used as a pharmaceutical composition for preventing or treating metabolic disease such as obesity, diabetes, hyperlipidemia, or fatty liver.

DETAILED DESCRIPTION

Hereinafter, the present invention will be described in detail.

The invention provides indole derivative represented by Formula 1 or pharmaceutically salt thereof:

[Formula 1]

In Formula 1, $R^1$ is —H, $C_{1-10}$ linear or branched alkyl group, $C_{2-10}$ linear or branched alkenyl group, $C_{3-12}$ cycloalkyl group, $C_{3-12}$ cycloalkyl $C_{1-5}$ alkyl group, $C_{5-12}$ aryl group, $C_{5-12}$ aryl $C_{1-5}$ alkyl group, $C_{5-12}$ aryl carbonyl group, $C_{1-10}$ linear or branched alkyl carbonyl group or $C_{1-10}$ linear or branched alkoxy carbonyl group;

$R^2$ is $C_{5-12}$ aryl group or $C_{5-12}$ heteroaryl group including one or more of N, O and S in a ring, in which the aryl group or heteroaryl group is non-substituted or substituted with —OH, $C_{1-10}$ linear or branched alkyl group, halogen or $R^5$ is —H, —OH, —$NH_2$, carboxyl group, amino carbonyl group, $C_{1-10}$ linear or branched alkyl group, $C_{1-5}$ linear or branched alkoxy group, $C_{1-10}$ linear or branched alkoxy carbonyl group or $C_{5-12}$ heterocycloalkyl group including one or more of N, O and S in a ring, n is an integer between 0-5;

$R^3$ is —H or $C_{1-5}$ linear or branched alkyl group;

$R^4$ is —H, $C_{1-5}$ linear or branched alkyl group or halogen;

X is carbonyl group or sulfonyl group; and

═══ is single or double bond.

Preferably, $R^1$ is —H, $C_{1-5}$ linear or branched alkyl group, $C_{2-6}$ linear or branched alkenyl group, $C_{3-6}$ cycloalkyl group, $C_{3-6}$ cycloalkyl $C_{1-3}$ alkyl group, $C_{5-7}$ aryl group, $C_{5-7}$ aryl $C_{1-3}$ alkyl group, $C_{5-7}$ arylcarbonyl group, $C_{1-6}$ linear or branched alkylcarbonyl group or $C_{1-5}$ linear or branched alkoxycarbonyl group;

$R^2$ is $C_{5-7}$ aryl group or $C_{5-7}$ heteroaryl group including one or more of N, O and S in a ring, in which the aryl group or heteroaryl group is non-substituted or substituted with —OH, $C_{1-5}$ linear or branched alkyl group, halogen or $R^5$ is —H, —OH, —$NH_2$, carboxyl group, aminocarbonyl group, $C_{1-5}$ linear or branched alkyl group, $C_{1-5}$ linear or branched alkoxy group, $C_{1-5}$ linear or branched alkoxycarbonyl group or $C_{5-7}$ heterocycloalkyl group including one or more of N, O and S in a ring, n is integer between 0-3;

$R^3$ is —H or $C_{1-10}$ linear or branched alkyl group;

$R^4$ is —H, $C_{1-10}$ linear or branched alkyl group or halogen;

X is carbonyl group or sulfonyl group;

═══ is single or double bond.

More preferably, $R^1$ is —H, —$CH_3$, (Boc),

, or

;

R² is

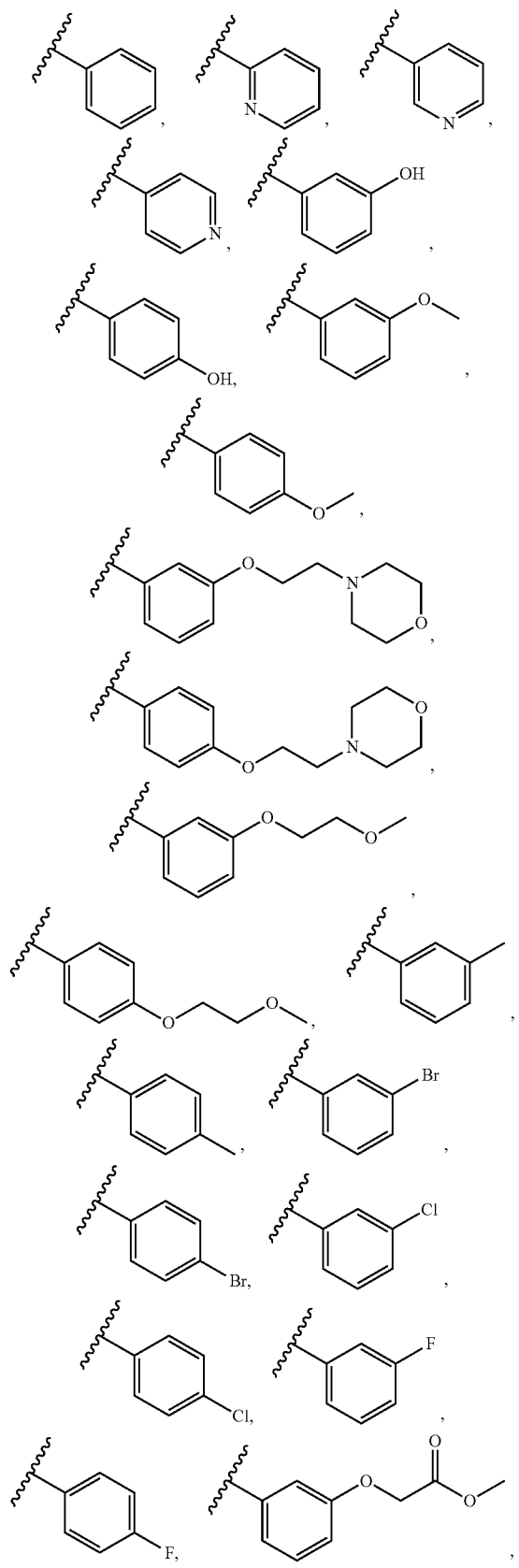

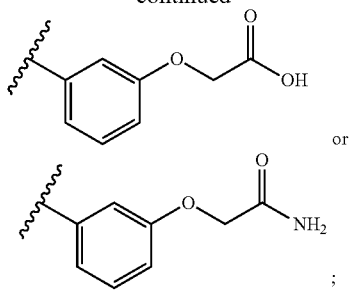

R³ is independently —H or isopropyl;
R⁴ is —H, —CH₃, isopropyl or fluoro;
X is carbonyl group or sulfonyl group; and
==== is single or double bond.

According to the present invention, the indole derivative represented by Formula 1 includes but is not limited to one selected from a group consisting of:

1) (E)-tert-butyl 3-(3-(2-benzoyl-1-isopropylhydrazinyl)-3-oxoprop-1-enyl)-1H-indole-1-carboxylate;
2) (E)-tert-butyl 3-(3-(1-isopropyl-2-picolinoylhydrazinyl)-3-oxoprop-1-enyl)-1H-indole-1-carboxylate;
3) (E)-tert-butyl 3-(3-(1-isopropyl-2-nicotinoylhydrazinyl)-3-oxoprop-1-enyl)-1H-indole-1-carboxylate;
4) (E)-tert-butyl 3-(3-(2-(3-hydroxybenzoyl)-1-isopropylhydrazinyl)-3-oxoprop-1-enyl)-1H-indole-1-carboxylate;
5) (E)-tert-butyl 3-(3-(2-(4-hydroxybenzoyl)-1-isopropylhydrazinyl)-3-oxoprop-1-enyl)-1H-indole-1-carboxylate;
6) (E)-tert-butyl 3-(3-(1-isopropyl-2-(3-methoxybenzoyl)hydrazinyl)-3-oxoprop-1-enyl)-1H-indole-1-carboxylate;
7) (E)-tert-butyl 3-(3-(1-isopropyl-2-(4-methoxybenzoyl)hydrazinyl)-3-oxoprop-1-enyl)-1H-indole-1-carboxylate;
8) (E)-tert-butyl 3-(3-(1-isopropyl-2-(3-(2-morpholinoethoxy)benzoyl)hydrazinyl)-3-oxoprop-1-enyl)-1H-indole-1-carboxylate;
9) (E)-tert-butyl 3-(3-(1-isopropyl-2-(4-(2-morpholinoethoxy)benzoyl)hydrazinyl)-3-oxoprop-1-enyl)-1H-indole-1-carboxylate;
10) (E)-tert-butyl 3-(3-(1-isopropyl-2-(3-(2-methoxyethoxy)benzoyl)hydrazinyl)-3-oxoprop-1-enyl)-1H-indole-1-carboxylate;
11) (E)-tert-butyl 3-(3-(1-isopropyl-2-(4-(2-methoxyethoxy)benzoyl)hydrazinyl)-3-oxoprop-1-enyl)-1H-indole-1-carboxylate;
12) (E)-tert-butyl 3-(3-(2-(3-bromobenzoyl)-1-isopropylhydrazinyl)-3-oxoprop-1-enyl)-1H-indole-1-carboxylate;
13) (E)-tert-butyl 3-(3-(2-(4-bromobenzoyl)-1-isopropylhydrazinyl)-3-oxoprop-1-enyl)-1H-indole-1-carboxylate;
14) (E)-tert-butyl 3-(3-(2-(4-chlorobenzoyl)-1-isopropylhydrazinyl)-3-oxoprop-1-enyl)-1H-indole-1-carboxylate;
15) (E)-tert-butyl 3-(3-(2-(3-fluorobenzoyl)-1-isopropylhydrazinyl)-3-oxoprop-1-enyl)-1H-indole-1-carboxylate;
16) (E)-tert-butyl 3-(3-(2-benzoylhydrazinyl)-3-oxoprop-1-enyl)-1H-indole-1-carboxylate;
17) (E)-tert-butyl 3-(3-oxo-3-(2-(phenylsulfonyl)hydrazinyl)prop-1-enyl)-1H-indole-1-carboxylate;

18) (E)-tert-butyl 3-(3-(1-isopropyl-2-(3-(2-methoxy-2-oxoethoxy)benzoyl)hydrazinyl)-3-oxoprop-1-enyl)-1H-indole-1-carboxylate;
19) (E)-2-(3-(2-(3-(1-(tert-butoxycarbonyl)-1H-indol-3-yl)acryloyl)-2-isopropylhydrazinecarbonyl)phenoxy)acetic acid;
20) (E)-tert-butyl 3-(3-(2-(3-(2-amino-2-oxoethoxy)benzoyl)-1-isopropylhydrazinyl)-3-oxoprop-1-enyl)-1H-indole-1-carboxylate;
21) N'-(3-(1-benzyl-1H-indol-3-yl)propanoyl)-N'-isopropylbenzohydrazide;
22) (E)-N'-(3-(1H-indol-3-yl)acryloyl)-N'-isopropylbenzohydrazide;
23) N'-(3-(1H-indol-3-yl)propanoyl)-N'-isopropylbenzohydrazide;
24) tert-butyl 3-(3-(2-benzoyl-1-isopropylhydrazinyl)-3-oxopropyl)-1H-indole-1-carboxylate;
25) (E)-N'-isopropyl-N'-(3-(1-methyl-1H-indol-3-yl)acryloyl)benzohydrazide);
26) (E)-N'-(3-(1-benzyl-1H-indol-3-yl)acryloyl)-N'-isopropylbenzohydrazide;
27) (E)-N'-isopropyl-N'-(3-(1-(3-methylbut-2-enyl)-1H-indol-3-yl)acryloyl)benzohydrazide;
28) (E)-N'-(3-(1-(cyclopropylmethyl)-1H-indol-3-yl)acryloyl)-N'-isopropylbenzohydrazide;
29) (E)-N'-(3-(1-cyclopropyl-1H-indol-3-yl)acryloyl)-N'-isopropylbenzohydrazide;
30) (E)-N'-(3-(1-acetyl-1H-indol-3-yl)acryloyl)-N'-isopropylbenzohydrazide;
31) (E)-N'-isopropyl-N'-(3-(1-pivaloyl-1H-indol-3-yl)acryloyl)benzohydrazide;
32) (E)-N'-(3-(1-benzoyl-1H-indol-3-yl)acryloyl)-N'-isopropylbenzohydrazide;
33) (E)-N'-(3-(1-(3,3-dimethylbutanoyl)-1H-indol-3-yl)acryloyl)-N'-isopropylbenzohydrazide;
34) (E)-3-fluoro-N'-isopropyl-N'-(3-(1-(3-methylbut-2-enyl)-1H-indol-3-yl)acryloyl)benzohydrazide);
35) (E)-tert-butyl 3-(3-(2-(3-fluorobenzoyl)-1-isopropylhydrazinyl)-3-oxoprop-1-enyl)-5-methyl-1H-indole-1-carboxylate;
36) (E)-tert-butyl 3-(3-(2-(3-fluorobenzoyl)-1-isopropylhydrazinyl)-3-oxoprop-1-enyl)-6-isopropyl-1H-indole-1-carboxylate;
37) (E)-tert-butyl 3-(3-(2-(3-fluorobenzoyl)-1-isopropylhydrazinyl)-3-oxoprop-1-enyl)-6-methyl-1H-indole-1-carboxylate;
38) (E)-tert-butyl 6-fluoro-3-(3-(2-(3-fluorobenzoyl)-1-isopropylhydrazinyl)-3-oxoprop-1-enyl)-1H-indole-1-carboxylate;
39) (E)-3-fluoro-N'-(3-(1-isopentyl-1H-indol-3-yl)acryloyl)-N'-isopropylbenzohydrazide;
40) (E)-3-fluoro-N'-isopropyl-N'-(3-(1-methyl-1H-indol-3-yl)acryloyl)benzohydrazide;
41) (E)-N'-(3-(1-ethyl-1H-indol-3-yl)acryloyl)-3-fluoro-N'-isopropylbenzohydrazide;
42) (E)-3-fluoro-N'-isopropyl-N'-(3-(1-propyl-1H-indol-3-yl)acryloyl)benzohydrazide;
43) (E)-tert-butyl 3-(3-(2-isonicotinoyl-1-isopropylhydrazinyl)-3-oxoprop-1-enyl)-1H-indole-1-carboxylate;
44) (E)-tert-butyl 3-(3-(2-(4-fluorobenzoyl)-1-isopropylhydrazinyl)-3-oxoprop-1-enyl)-1H-indole-1-carboxylate;
45) (E)-tert-butyl 3-(3-(2-(3-chlorobenzoyl)-1-isopropylhydrazinyl)-3-oxoprop-1-enyl)-1H-indole-1-carboxylate;
46) (E)-4-fluoro-N'-(3-(1-isopentyl-1H-indol-3-yl)acryloyl)-N'-isopropylbenzohydrazide;
47) (E)-tert-butyl 3-(3-(1-isopropyl-2-(3-methylbenzoyl)hydrazinyl)-3-oxoprop-1-enyl)-1H-indole-1-carboxylate;
48) (E)-tert-butyl 3-(3-(1-isopropyl-2-(4-methylbenzoyl)hydrazinyl)-3-oxoprop-1-enyl)-1H-indole-1-carboxylate;
49) (E)-4-fluoro-N'-isopropyl-N'-(3-(1-(3-methylbut-2-enyl)-1H-indol-3-yl)acryloyl)benzohydrazide;
50) (E)-N'-isopropyl-3-methyl-N'-(3-(1-(3-methylbut-2-enyl)-1H-indol-3-yl)acryloyl)benzohydrazide; and
51) (E)-N'-isopropyl-4-methyl-N'-(3-(1-(3-methylbut-2-enyl)-1H-indol-3-yl)acryloyl)benzohydrazide, or pharmaceutically acceptable salt thereof.

The structure of the indole derivatives of Formula 1 is tabulated below:

TABLE 1

| Indole derivative | Structure |
| --- | --- |
| 1 | 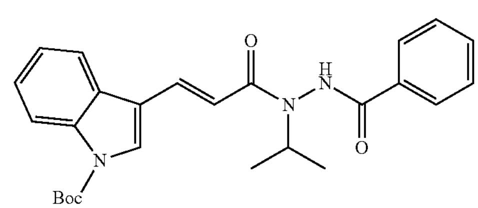 [SMILES: CC(C)N(NC(=O)c1ccccc1)C(=O)/C=C/c1cn(C(=O)OC(C)(C)C)c2ccccc12] |
| 2 | 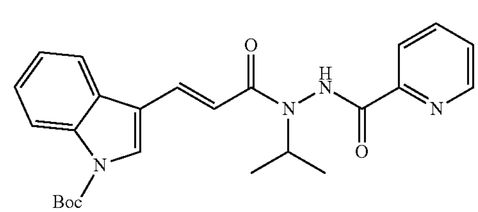 [SMILES: CC(C)N(NC(=O)c1ccccn1)C(=O)/C=C/c1cn(C(=O)OC(C)(C)C)c2ccccc12] |

TABLE 1-continued

| Indole derivative | Structure |
|---|---|
| 3 | (indole-Boc)-CH=CH-C(O)-N(iPr)-NH-C(O)-(3-pyridyl) |
| 4 | (indole-Boc)-CH=CH-C(O)-N(iPr)-NH-C(O)-(3-hydroxyphenyl) |
| 5 | (indole-Boc)-CH=CH-C(O)-N(iPr)-NH-C(O)-(4-hydroxyphenyl) |
| 6 | (indole-Boc)-CH=CH-C(O)-N(iPr)-NH-C(O)-(3-methoxyphenyl) |
| 7 | (indole-Boc)-CH=CH-C(O)-N(iPr)-NH-C(O)-(4-methoxyphenyl) |
| 8 | (indole-Boc)-CH=CH-C(O)-N(iPr)-NH-C(O)-(3-(2-morpholinoethoxy)phenyl) |
| 9 | (indole-Boc)-CH=CH-C(O)-N(iPr)-NH-C(O)-(4-(2-morpholinoethoxy)phenyl) |

TABLE 1-continued
| Indole derivative | Structure |
|---|---|
| 10 | 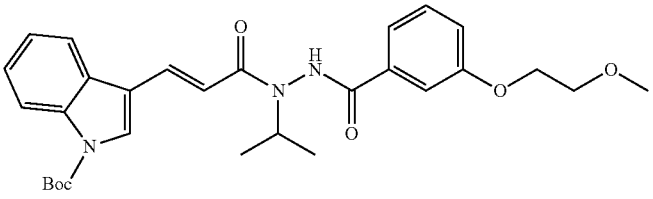 [SMILES: COCCOc1cccc(C(=O)NN(C(=O)/C=C/c2cn(C(=O)OC(C)(C)C)c3ccccc23)C(C)C)c1] |
| 11 | 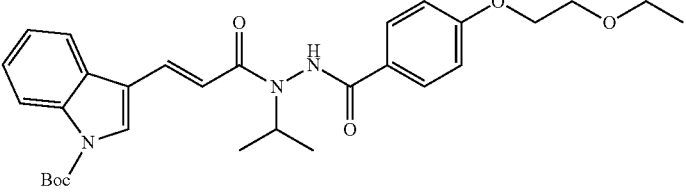 |
| 12 | 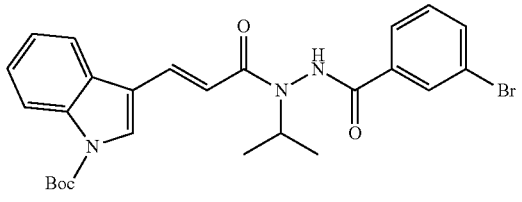 [SMILES: CC(C)N(NC(=O)c1cccc(Br)c1)C(=O)/C=C/c1cn(C(=O)OC(C)(C)C)c2ccccc12] |
| 13 | 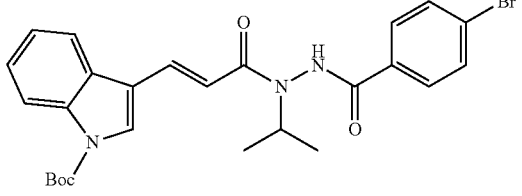 |
| 14 | 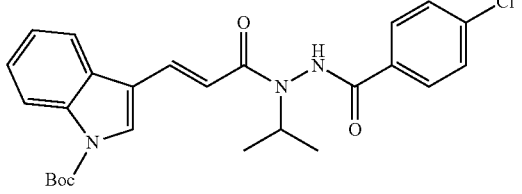 |
| 15 | 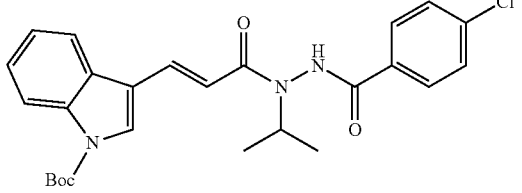 |
| 16 | 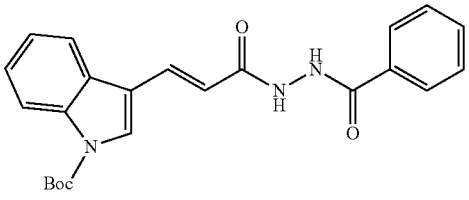 [SMILES: CC(C)(C)OC(=O)n1cc(/C=C/C(=O)NNC(=O)c2ccccc2)c2ccccc21] |

TABLE 1-continued

| Indole derivative | Structure |
|---|---|
| 17 | (structure) |
| 18 | (structure) |
| 19 | (structure) |
| 20 | (structure) |
| 21 | (structure) |
| 22 | (structure) |
| 23 | (structure) |

TABLE 1-continued
| Indole derivative | Structure |
|---|---|
| 24 | 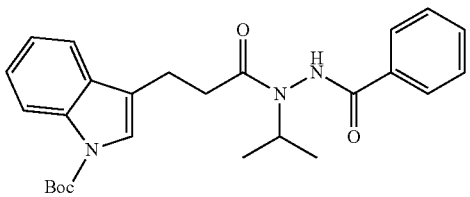 [SMILES: CC(C)N(NC(=O)c1ccccc1)C(=O)CCc1cn(C(=O)OC(C)(C)C)c2ccccc12] |
| 25 | 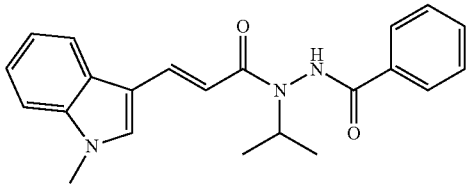 [SMILES: CC(C)N(NC(=O)c1ccccc1)C(=O)/C=C/c1cn(C)c2ccccc12] |
| 26 | 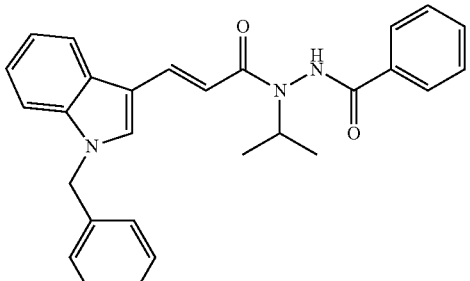 |
| 27 | 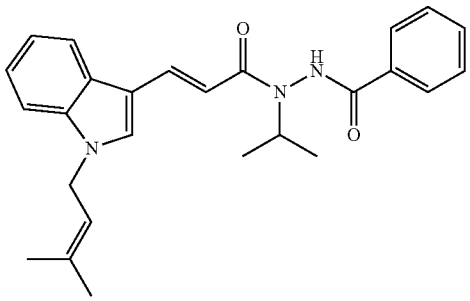 [SMILES: CC(C)=CCn1cc(/C=C/C(=O)N(NC(=O)c2ccccc2)C(C)C)c2ccccc21] |
| 28 | 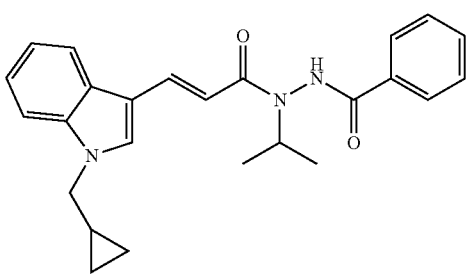 [SMILES: CC(C)N(NC(=O)c1ccccc1)C(=O)/C=C/c1cn(CC2CC2)c2ccccc12] |
| 29 | 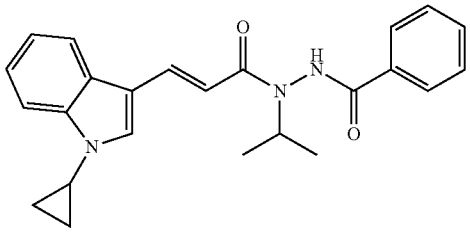 [SMILES: CC(C)N(NC(=O)c1ccccc1)C(=O)/C=C/c1cn(C2CC2)c2ccccc12] |

TABLE 1-continued

| Indole derivative | Structure |
|---|---|
| 30 | 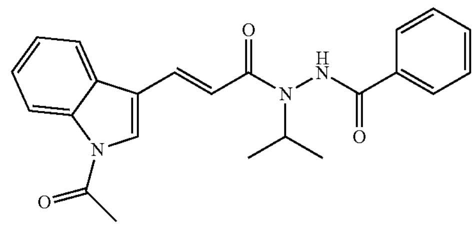 [SMILES: CC(=O)n1cc(/C=C/C(=O)N(NC(=O)c2ccccc2)C(C)C)c2ccccc21] |
| 31 | 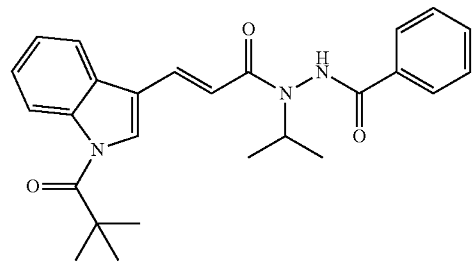 [SMILES: CC(C)N(NC(=O)c1ccccc1)C(=O)/C=C/c1cn(C(=O)C(C)(C)C)c2ccccc12] |
| 32 | 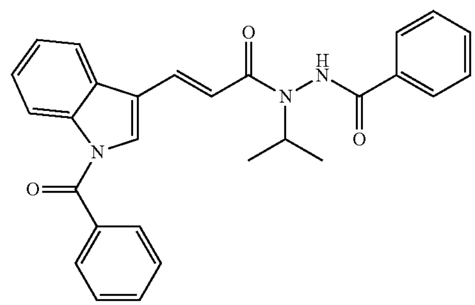 [SMILES: CC(C)N(NC(=O)c1ccccc1)C(=O)/C=C/c1cn(C(=O)c2ccccc2)c2ccccc12] |
| 33 | 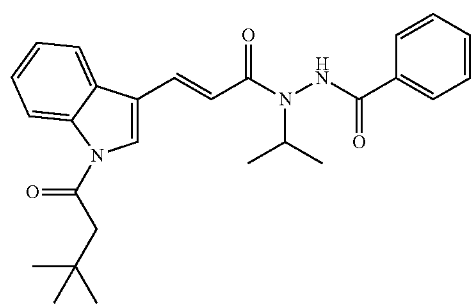 [SMILES: CC(C)N(NC(=O)c1ccccc1)C(=O)/C=C/c1cn(C(=O)CC(C)(C)C)c2ccccc12] |
| 34 | 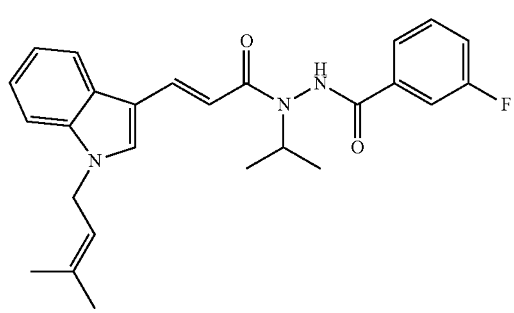 [SMILES: CC(C)=CCn1cc(/C=C/C(=O)N(NC(=O)c2cccc(F)c2)C(C)C)c2ccccc21] |

TABLE 1-continued
| Indole derivative | Structure |
|---|---|
| 35 | 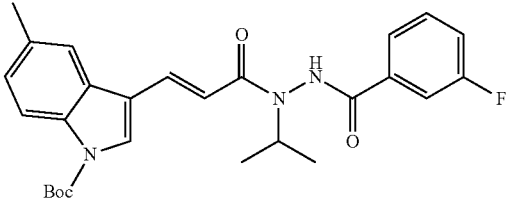 [SMILES: Cc1ccc2c(c1)c(/C=C/C(=O)N(NC(=O)c1cccc(F)c1)C(C)C)cn2C(=O)OC(C)(C)C] |
| 36 | 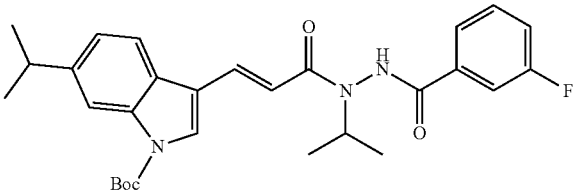 [SMILES: CC(C)c1ccc2c(/C=C/C(=O)N(NC(=O)c3cccc(F)c3)C(C)C)cn(C(=O)OC(C)(C)C)c2c1] |
| 37 | 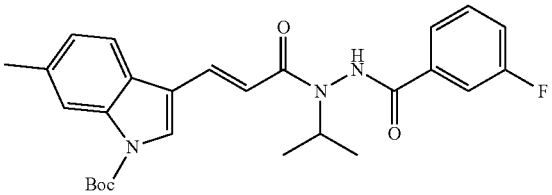 [SMILES: Cc1ccc2c(/C=C/C(=O)N(NC(=O)c3cccc(F)c3)C(C)C)cn(C(=O)OC(C)(C)C)c2c1] |
| 38 | 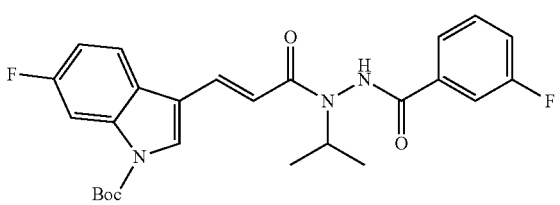 [SMILES: CC(C)N(NC(=O)c1cccc(F)c1)C(=O)/C=C/c1cn(C(=O)OC(C)(C)C)c2cc(F)ccc12] |
| 39 | 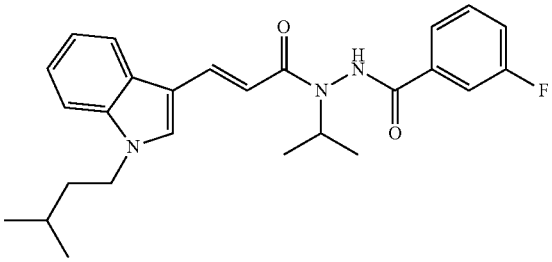 [SMILES: CC(C)CCn1cc(/C=C/C(=O)N(NC(=O)c2cccc(F)c2)C(C)C)c2ccccc21] |
| 40 | 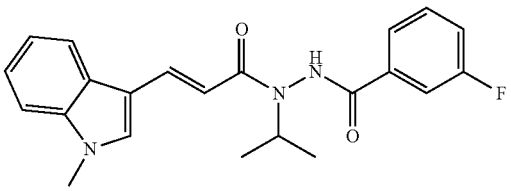 [SMILES: CC(C)N(NC(=O)c1cccc(F)c1)C(=O)/C=C/c1cn(C)c2ccccc12] |
| 41 | 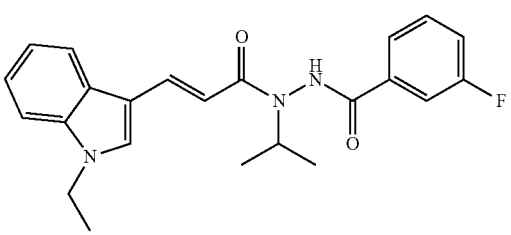 [SMILES: CCn1cc(/C=C/C(=O)N(NC(=O)c2cccc(F)c2)C(C)C)c2ccccc21] |

TABLE 1-continued

| Indole derivative | Structure |
|---|---|
| 42 | 1-propyl-indole-3-yl cinnamoyl-N-isopropyl-N'-(3-fluorobenzoyl)hydrazide |
| 43 | 1-Boc-indole-3-yl cinnamoyl-N-isopropyl-N'-(isonicotinoyl)hydrazide |
| 44 | 1-Boc-indole-3-yl cinnamoyl-N-isopropyl-N'-(4-fluorobenzoyl)hydrazide |
| 45 | 1-Boc-indole-3-yl cinnamoyl-N-isopropyl-N'-(3-chlorobenzoyl)hydrazide |
| 46 | 1-isopentyl-indole-3-yl cinnamoyl-N-isopropyl-N'-(4-fluorobenzoyl)hydrazide |
| 47 | 1-Boc-indole-3-yl cinnamoyl-N-isopropyl-N'-(3-methylbenzoyl)hydrazide |
| 48 | 1-Boc-indole-3-yl cinnamoyl-N-isopropyl-N'-(4-methylbenzoyl)hydrazide |

TABLE 1-continued

| Indole derivative | Structure |
| --- | --- |
| 49 | 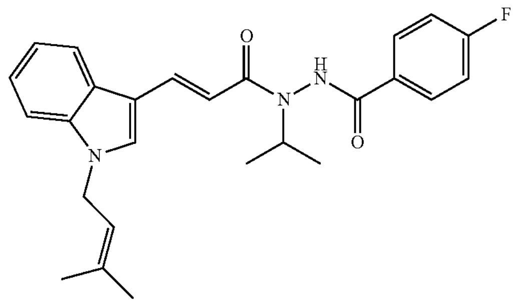 [SMILES: CC(C)=CCn1cc(/C=C/C(=O)N(NC(=O)c2ccc(F)cc2)C(C)C)c2ccccc21] |
| 50 | 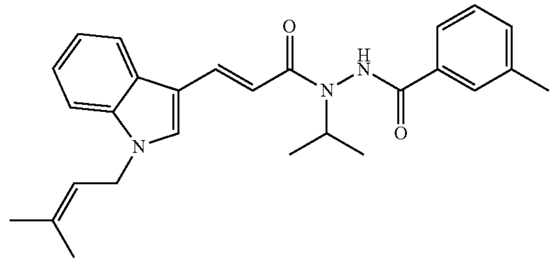 [SMILES: CC(C)=CCn1cc(/C=C/C(=O)N(NC(=O)c2cccc(C)c2)C(C)C)c2ccccc21] |
| 51 | 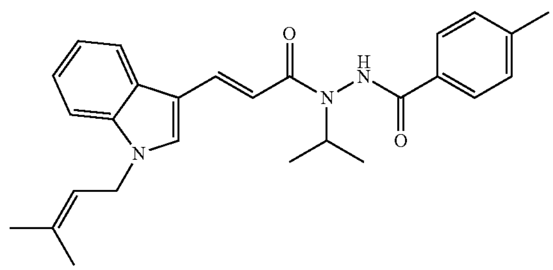 [SMILES: CC(C)=CCn1cc(/C=C/C(=O)N(NC(=O)c2ccc(C)cc2)C(C)C)c2ccccc21] |

The present invention comprises not only indole derivative represented by Formula 1 or pharmaceutically acceptable salt thereof, but also solvates, hydrates, or prodrug that may be prepared from the same.

The indole derivative represented by Formula 1 according to the present invention may be used in the form of pharmaceutically acceptable salt, and the pharmaceutically acceptable salt may advantageously use acid addition salt formed by pharmaceutically acceptable free acid. The acid addition salt is obtained from inorganic acid such as, for example, hydrochloric acid, nitric acid, phosphoric acid, sulfuric acid, hydrobromic acid, iodinated acid, nitrous acid, or phosphorous acid, and nontoxic organic acid such as, for example, mono- and di-carboxylic acids, phenyl-substituted alkanoate, hydroxy alkanoate, and alkanedioate, aromatic acids, aliphatic and aromatic sulfonic acids. The pharmaceutically non-toxic salts include sulfate, pyrosulfite, bisulfate, sulfite, bisulfate, sulfite, nitrate, phosphate, mono-hydrogen phosphate, dehydrogen phosphate, meta phosphate, pyrophosphate chloride, bromide, iodide, fluoride, acetate, propionate, decanoate, caprylate, acrylate, formate, isobutylate, caprate, heptanoate, propyolate, oxalate, malonate, succinate, suberate, sebacate, fumarate, maliate, butin-1,4-dioate, hexane-1,6-dioate, benzoate, chloro-benzoate, methylbenzoate, dinitrobenzoate, hydroxybenzoate, methoxybenzoate, phthalate, terephthalate, benzenesulfonate, toluenesulfonate, chlorobenzene sulfonate, xylenesulfonate, phenylacetate, phenylpropionate, phenylbutyrate, citrate, lactate, β-hydroxy-butyrate, glycolate, malate, tatrate, methanesulfonate, propanesulfonate, naphthalene-1-sulfonate, naphthalene-2-sulfonate, or mandelate.

Acid addition salt according to the present invention may be prepared by a conventional manner, for example, by dissolving indole derivative represented by Formula 1 in excess acid aqueous solution, and precipitating the salt using water-miscible organic solvent such as, for example, methanol, ethanol, acetone, or acetonitrile. It is also possible to prepare the salt by heating a same amount of the indole derivative represented by Formula 1 and acid or alcohol in water, and subsequently drying by evaporating the mixture, or suction-filtering the precipitate salt.

In addition, the pharmaceutically acceptable salt may be prepared using the base. It is possible to prepare the alkali metal or alkaline earth metal salt, by dissolving the compound in, for example, excess alkali metal or alkaline earth metal hydroxide solution, filtering the non-dissolved compound salt, and evaporating and drying the filtrate. The metal salt may be prepared with the sodium salt, potassium salt or calcium salt, considering manufacturing constraints. In addition, corresponding silver salt may be obtained by reacting metal or alkaline earth metal salt with suitable silver salt (e.g., silver nitrate).

In addition, the present invention provides a preparation method of indole derivative represented by the Formula 1.

According to the present invention, the preparation method of the indole derivatives of Formula 1 may include a step of obtaining compound represented by Formula 1a, by dehydration reacting the indole derivative represented by Formula 2 with the compound represented by Formula 3, as indicated by Reaction Formula 1 below:

[Reaction Formula 1]

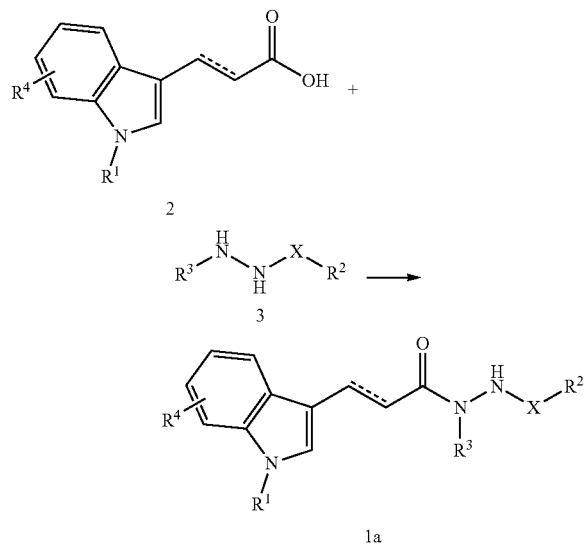

where, $R^1$, $R^2$, $R^3$, $R^4$, X and ===== are as defined in Formula 1; and Formula 1a is included in Formula 1.

Referring to Reaction Formula 1 according to the present invention, the indole derivative represented by Formula 2 and the compound represented by Formula 3 may be those that are readily available commercially or prepared by known methods.

The organic solvent used in the reaction may be that which does not adversely affect the reaction, and preferably be DMF.

The reaction temperature may be included in a range from room temperature to boiling point of the solvent, although not limited thereto.

Specifically, after slowly drop-wise adding N,N-diisopropylethylamine to a solution in which the compounds of Formulae 2 and 3 is dissolved in DMF solvent with HATU and allowing reaction to occur, column chromatography performed upon completion of the reaction gave compound represented by Formula 1a.

In addition, according to another embodiment of the present invention, the indole derivative of Formula 1 may be prepared by, as indicated by Reaction Formula 2 below:

adding iodomethane to (E)-3-(1H-indol-3-yl) acrylic acid for the purpose of introducing protecting group, for methylation which gives (E)-methyl 3-(1H-indol-3-yl) acrylate (step 1);

obtaining compound 4a introduced with $R^6$ substituent, by alkylation of nitrogen in (E)-methyl 3-(1H-indol-3-yl) acrylate obtained at step 1 (step 2);

obtaining compound 4b by adding sodium hydroxide to the compound of 4a obtained at step 2 for de-protecting purpose (step 3); and obtaining compound 1b by adding N'-isopropylbenzohydrazide to the compound 4b obtained at step 3 for dehydration purpose (step 4).

[Reaction Formula 2]

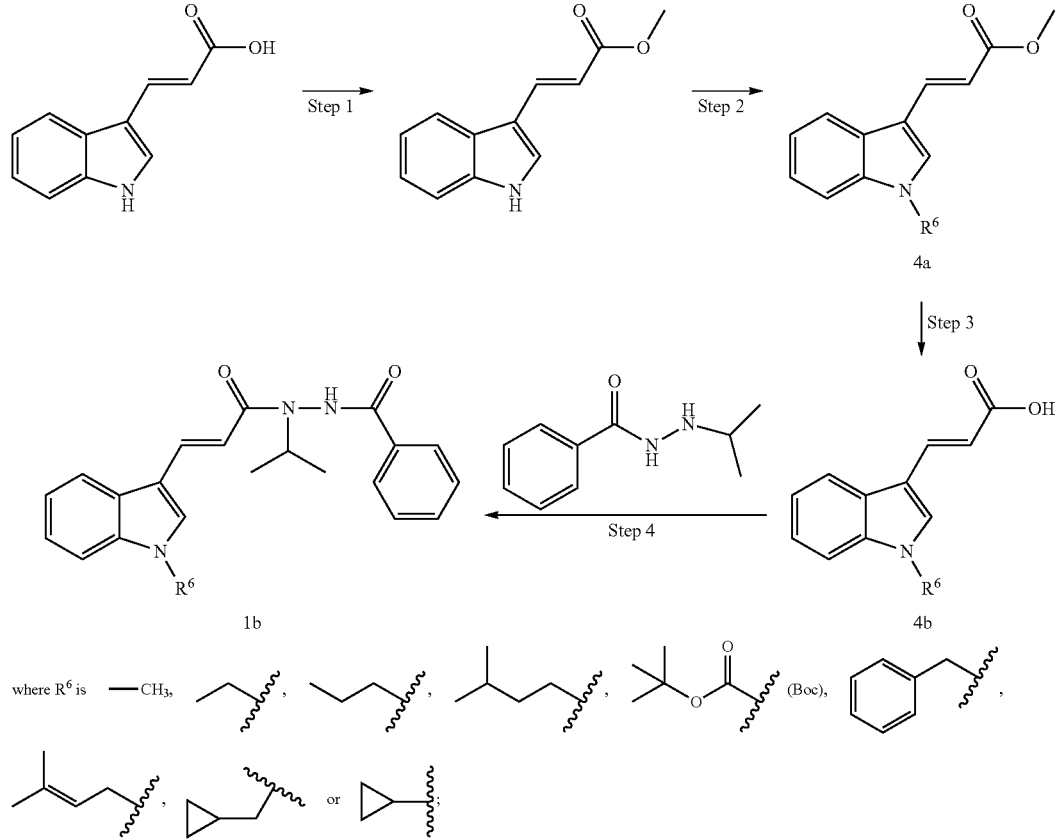

and

Formula 1b is included in Formula 1.

Referring to Reaction Formula 2, step 1 involves obtaining (E)-methyl 3-(1H-indol-3-yl)acrylate by adding iodomethane and base to (E)-3-(1H-indol-3-yl)acrylic acid to introduce the protecting group.

For the base, $K_2CO_3$, NaH etc. may be used, and for $R^6$ substituent, substituted halogen element, or cyclopropyl boronic acid may be used.

In addition, for the solvent, acetone, which does not adversely affect the reaction, may be used.

Furthermore, the reaction temperature is not particularly limited, but may be within a range between room temperature and boiling point of the solvent.

Specifically, it is possible to slowly drop-wise add iodomethane, which is the solution obtained by adding starting materials, i.e., trans-3-indole acrylic acid and $K_2CO_3$ to acetone, and perform column chromatography upon completion of the reaction to thus obtain (E)-methyl-3-(1H-indol-3-yl)acrylate.

Step 2 involves obtaining the compound of Formula 4a, by adding $R^6$ substituent and base to (E)-methyl 3-(1H-indol-3-yl)acrylate prepared at step 1 for the purpose of introducing $R^6$ substituent.

At this time, for the solvent, those such as DMF that do not adversely affect the reaction may be used.

In addition, for the base, $K_2CO_3$, NaH, etc. may be used, and for the reagent to help the reaction, DMAP or the like may be used.

Furthermore, the reaction temperature is not particularly limited, but may be within a range from room temperature to boiling point of the solvent.

Specifically, it is possible to add NaH and (E)-methyl 3-(1H-indol-3-yl)acrylate obtained at step 1 to DMF solution, slowly drop-wise add halogen-substituted $R^6$ substituent for reaction, and after the end of the reaction, perform column chromatography to obtain compound of Formula 4a.

Step 3 involves preparing compound of Formula 4b from which the protecting group, introduced by the addition of sodium hydroxide to the compound of Formula 4a of step 2, is eliminated.

At this time, the solvent such as THF, methanol, water, etc. which does not adversely affect the reaction may be used alone or in combination.

Specifically, the compound obtained at step 2 and compound of Formula 4a and sodium hydroxide are added to THF, methanol, water-miscible solvent for reaction, and upon completion of the reaction, the column chromatography is performed to obtain a compound of Formula 4b.

Step 4 involves preparing compound 1b by dehydration reaction of the compound of Formula 4b obtained at step 3 with N'-isopropylbenzohydrazide.

At this time, the organic solvent such as DMF that does not adversely affect the reaction may preferably be used.

In addition, the reaction temperature is not particularly limited, but may be in a range between room temperature and boiling point of the solvent.

Specifically, after slowly drop-wise adding N,N-diisopropylethylamine (DIPEA) to a solution obtained by dissolving the compound of Formula 4b and HATU in DMF solvent for reaction, the compound represented by Formula 1b may be obtained by column chromatography.

In addition, according to another embodiment of the present invention, a preparation method of indole derivative of Formula 1 may include following steps as indicated by Reaction Formula 3 below:

obtaining (E)-N'-(3-(1H-indol-3-yl)acryloyl)-N'-isopropylbenzohydrazide by adding N'-isopropylbenzohydrazide to (E)-3-(1H-indol-3-yl)acrylic acid for dehydration reaction (step 1); and obtaining compound 1c introduced with $R^7$ substituent, by alkylation of nitrogen in the (E)-N'-(3-(1H-indol-3-yl)acryloyl)-N'-isopropyl benzohydrazide obtained at step 1 (step 2).

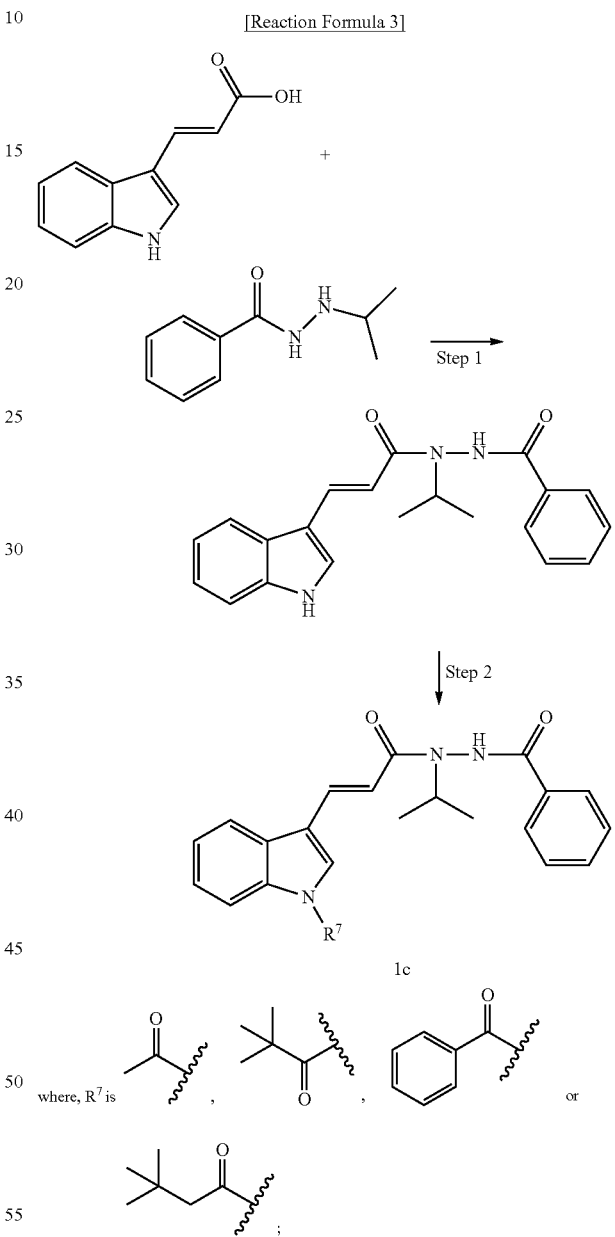

[Reaction Formula 3]

and

Formula 1c is included in Formula 1.

Referring to Reaction Formula 3 according to the present invention, step 1 involves preparing (E)-N'-(3-(1H-indol-3-yl)acryloyl)-N'-isopropylbenzohydrazide by adding N'-isopropylbenzohydrazide to (E)-3-(1H-indol-3-yl)acrylic acid for dehydration reaction.

At this time, the organic solvent such as DMF that does not adversely affect the reaction may preferably be used.

In addition, the reaction temperature is not particularly limited, but may be in a range between room temperature and boiling point of the solvent.

Specifically, after slowly drop-wise adding N,N-diisopropylethylamine (DIPEA) to a solution obtained by dissolving the trans-3-indole acrylic acid and n'-isopropylbenzohydrazide and HATU in DMF solvent for reaction, (E)-N'-(3-(1H-indol-3-yl)acryloyl)-N'-isopropylbenzohydrazide may be obtained by column chromatography.

Step 2 involves obtaining compound 1c by adding R⁷ substituent and base to (E)-N'-(3-(1H-indol-3-yl)acryloyl)-N'-isopropyl benzohydrazide obtained at step 1 for alkylation reaction to introduce R⁷ substituent therein.

At this time, for the solvent, those such as DMF that do not adversely affect the reaction may be used.

In addition, for the base, K₂CO₃, NaH, etc. may be used, and for the reagent to help the reaction, DMAP or the like may be used.

Furthermore, the reaction temperature is not particularly limited, but may be within a range from room temperature to boiling point of the solvent.

Specifically, it is possible to add K₂CO₃, NaH and E)-N'-(3-(1H-indol-3-yl)acryloyl)-N'-isopropyl benzohydrazide obtained at step 1 to DMF solution, slowly drop-wise add halogen-substituted R⁷ substituent for reaction, and after the end of the reaction, perform column chromatography to obtain compound of Formula 1c.

Furthermore, according to another embodiment of the present invention, a preparation method of indole derivative of Formula 1 may include following steps as indicated by Reaction Formula 4 below:

preparing compound represented by Formula 6 by allowing the compound represented by Formula 5 to react with ethyl(triphenylphosphoranylidene)acetate (step 1);

preparing compound represented by Formula 7 by adding sodium hydroxide to the compound of Formula 6 prepared at step 1 for deprotecting purpose (step 2);

preparing compound represented by Formula 4c with protected amino group, by allowing amino group of compound represented by Formula 7 prepared at step 2 to react with di-tert-buthyl dicarbonate (step 3); and preparing compound represented by Formula 1d by dehydrating the compound of Formula 4c prepared at step 3 with the compound represented by Formula 3a (step 4).

[Reaction Formula 4]

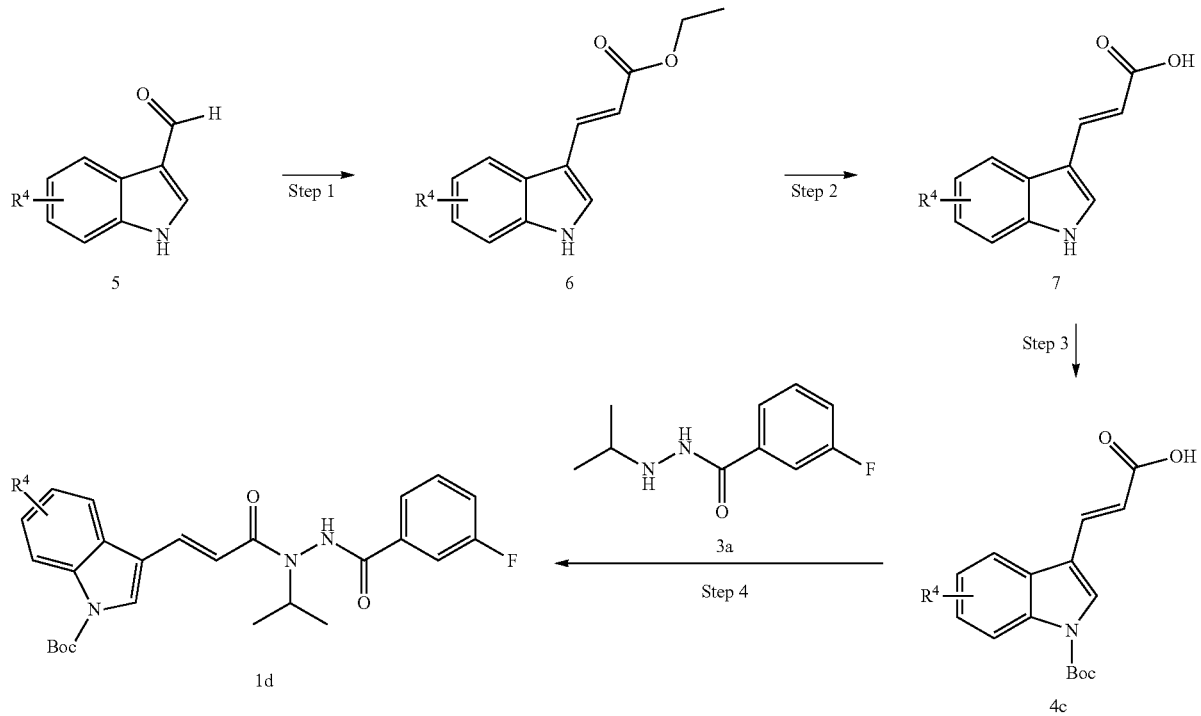

where, $R^4$ is as defined in Formula 1;

Boc is

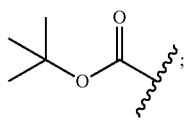 [SMILES: *C(=O)OC(C)(C)C]

and

Formula 1d is included in Formula 1.

Referring to Reaction Formula 4, step 1 involves preparing compound represented by Formula 6 by allowing the compound represented by Formula 5 to react with ethyl(triphenylphosphoranylidene)acetate.

For the organic solvent, any solvent that does not adversely affect the reaction may be used, and preferably, benzene may be used.

Further, the reaction temperature may be within a boiling point range of the solvent, although not limited thereto.

To be specific, the compound of Formula 6 may be obtained by dissolving the compound represented by Formula 5 in benzene, slowly drop-wise adding ethyl(triphenylphosphoranylidene)acetate, stirring under reflux for reaction, and performing column chromatography after completion of the reaction.

Step 2 involves preparing compound represented by Formula 7 by adding sodium hydroxide to the compound of Formula 6 prepared at step 1 for deprotecting purpose The solvent such as THF, methanol, or water that does not adversely affect the reaction may be used singly or in combination.

To be specific, it is possible to obtain the compound of Formula 7 by adding the compound of Formula 6 obtained at step 1 and sodium hydroxide to a mixture solution of THF, methanol and water for reaction, and performing column chromatography after the completion of the reaction.

Step 3 involves preparing compound represented by Formula 4c with protected amino group, by allowing amino group of compound represented by Formula 7 prepared at step 2 to react with di-tert-buthyl dicarbonate.

For the organic solvent, any solvent that does not adversely affect the reaction may be used, and preferably, THF may be used.

Further, the reaction temperature may be within a boiling point range of the solvent, although not limited thereto.

Further, the base such as TEA may be used, and reagent such as DMAP may be used to help the reaction.

To be specific, it is possible to obtain the compound of Formula 4c with protected amino group, by dissolving the compound of Formula 7 in TMF, sequentially drop-wise adding DMAP, TEA and di-tert-buthyl dicarbonate, allowing reaction to occur at room temperature, and re-crystallizing after completion of the reaction.

Step 4 involves preparing compound represented by Formula 1d by dehydrating the compound of Formula 4c prepared at step 3 with the compound represented by Formula 3a.

For the organic solvent, any solvent that does not adversely affect the reaction may be used, and preferably, DMF may be used.

Further, the reaction temperature may be within a range between room temperature and a boiling point of the solvent, although not limited thereto.

To be specific, it is possible to obtain the compound of Formula 1d by dissolving the compound of Formula 4c obtained at step 3 with HATU in DMF, slowly drop-wise adding N,N-diisopropylethylamine (DIPEA) in DMF solution for reaction, and performing column chromatography after completion of the reaction.

Furthermore, the present invention provides a composition, particularly a pharmaceutical composition for preventing and treating metabolic disease such as obesity, diabetes, hyperlipidemia or fatty liver, comprising the indole derivative represented by Formula 1 or pharmaceutically acceptable salt thereof as active ingredient.

The diabetes may preferably be type II diabetes.

In addition, the present invention provides a composition, particularly a health food composition for preventing or treating metabolic disease such as obesity, diabetes, hyperlipidemia or fatty liver, comprising the indole derivative represented by Formula 1 as active ingredient.

Furthermore, the present invention provides a diacylglycerol acyltransferase (DGAT) inhibitor comprising indole derivative of Formula 1.

In addition, the present invention provides a method for treating metabolic disease such as obesity, diabetes, hyperlipidemia or fatty liver, or complications thereof, comprising a step of administering indole derivative represented by Formula 1 or pharmaceutically acceptable salt thereof to a patient in need of the same.

Furthermore, the present invention provides the indole derivative of Formula 1 or pharmaceutically acceptable salt thereof, for use in preventing or treating metabolic disease or complications thereof.

The composition containing indole derivative of Formula 1 or pharmaceutically acceptable salt thereof as active ingredient according to the present invention will be explained below in detail.

DGAT is a catalytic enzyme of the last process of the glycerol 3-phosphate path that plays a role of synthesizing triglyceride using sn-1,2-diacylglycerol and fatty acyl CoA as a substrate, and the biosynthesis of triglyceride is performed along the path of glycerol 3-phosphate (liver and adipose tissues, etc.). Accordingly, with the inhibited DGAT activity, the catalytic reaction of the DGAT enzyme of synthesizing triglyceride is blocked or has reduced synthesis efficiency.

With the inhibition of triglyceride synthesis, report says that accumulation of fat in adipose tissue is inhibited, the size of the fat cells is reduced, secretion of adiponectin from cells is promoted, momentum increases, and high fat diet-induced weight gain is suppressed (Smith S J. et al., Nature genetics, 25, 87-90, 2000; Chen et al.,/Clin Invest., 109 (8), 1049-1055, 2002; Chen et al., J Clin Invest., Ill, 1715-1722, 2003; Chen et al. Am. J. Physiol. Endocronol. Metab., 284,; E213-218, 2003).

In addition, DGAT inhibition is reported as having benefit of improving insulin resistance by preventing accumulation of fat in the non-adipose tissue such as muscle, liver, or pancreas.

When cells are stimulated by insulin, the insulin receptor substance-1 has reduced inhibitory phosphorylation and glucose transporter-4 (GLUT-4) is ectocytosized to the membrane via signaling path of phosphatidylinosito-3 kinase (PI-3K), protein kinase B (PKB) and protein kinase $C_\lambda$ ($PKC_\lambda$). As a result, glucose is introduced into cells. When DGAT activity is inhibited in the cells, activities of PI-3K, PKB, and $PKC_\lambda$ increase to thus increase the number of GLUT-4 ectocytosized to membrane, and subsequently increase the number of glucose to be introduced into the cells. That is, the DGAT activity inhibition increases insulin sensitivity, to thus improve insulin resistance (Chen et al., Arterioscler Thromb Vase Biol. 25 (3): 482-486, 2005; Chen et al.,/Clin Invest: 111 (11): 1715-22, 2003; Chen et J Clin Invest. 109 (8): 1049 to 1055, 2002; Chen et Al., Diabetes. 51 (11). '3189 to 3195, 2002; Subauste ant and bur., Curr Drug Targets Immune Endocr Disord Metabol., 3 (4): 263-270, 2003).

Therefore, DGAT activity-inhibiting substances can be advantageously used to prevent and treat metabolic disease such as obesity, diabetes, hyperlipidemia, and fatty liver, as is well documented by a variety of researches (Chen H C, et al., Trends Cardiovasc. Med., 10, 188-192, 2000; Farese Jr. et al., Curr, Op/n. Lip idol., 11, 229-234, 2000; A. Subauste et. al., Cur runt Drug Target t-Immun, Endocrine & Metabol Disorders, 3, 263-270, 2003; Y. Yu et. al. Ana Is of Medicine, 36'252-261; Hubert C. et al., Arterioscler. Thromb. Vase. Biol., 25, 1-5, 2005; Smith SJ. et al., Nature genetics, 25, 87-90, 2000).

The indole derivatives of Formula 1 of the present invention uses microsomal protein separated from DGAT1 & 2-expressing sf-9 insect cells as a source of enzymes for the purpose of measuring human DGAT1 & 2 enzyme activity, and uses a substrate of 1,2-diacylglycerol and [$^{14}$C]palmitoyl-CoA. Accordingly, in the experiment of measuring amount of radioactivity of [$^{14}$C]triacylglycerol produced after enzymatic reaction with 1,2-diacylglycerol and [$^{14}$C]palmitoyl-CoA, it was confirmed that the DGAT enzymatic activity was inhibited in a concentration-dependent manner (see Experimental Example 1).

In addition, when HepG2 cells and HuTu80 cells were treated with the indole derivative of Formula 1 according to the present invention, it was confirmed that the generation of triglyceride in the cells was inhibited (see Experimental Examples 2 and 3).

Further, as a result of orally administering mouse with indole derivative of Formula 1 according to the present invention and observing variations in triglyceride concentration by administering corn oil, it was confirmed that the mouse administered with the indole derivative of formula 1 according to the present invention showed superior inhibitory effect of the rising of triglyceride concentration compared to other mouse group (see Experimental Example 4). The result of acute toxicity evaluation on mouse also revealed no toxicity in vivo and safety for human body (see Experimental Example 5).

Accordingly, since the indole derivative represented by Formula 1 according to the present invention can effectively inhibit activity of diacylglycerol acyltransferase (DGAT) which is an inducer of metabolis disease such as obesity, diabetes, hyperlipidemia or fatty liver in the course of lipid metabolism and effectively regulate the lipid metabolism and energy metabolism, it is possible to advantageously use the indole derivative as a pharmaceutical composition for preventing or treating metabolic disease including obesity, diabetes, hyperlipidemia or fatty liver.

The term "prevent" as used herein encompasses all the actions to inhibit or delay onset of disease with administration of the composition. Further, the term "enhance" or "treat" as used herein encompasses all the actions that improve or change the symptoms of the disease in a beneficial way, by the administration of the composition.

As used herein, the term "administer" refers to provision of a predetermined substance to a patient in an arbitrarily suitable manner, and may include all the generally-available routes of administration including oral or non-oral route to a targeted site. Further, the composition may be administered with a predetermined device by which the active substance can move to the targeted cells.

The pharmaceutical composition according to the invention may be formulated, in which case the generally-used filling agents, extenders, binders, wetting agents, disintegrants, surfactants, or excipients may be used.

The solid formulation for oral administration may include tablets, pills, powders, granules, capsules, or troche, and may be formulated by mixing one or more compounds represented by the present invention with one or more excipients such as, for example, starch, calcium carbonate, sucrose or lactose or gelatin. Also, in addition to the simple excipients, lubricant such as talc, or magnesium stearate may be used. A liquid formulation for oral administration includes suspension, liquid formulations, emulsion, or syrup, which may contain commonly used simple diluent such as water, liquid paraffin, and other various excipients, such as, for example, wetting agents, sweeteners, fragrances, or preservatives.

Formulation for parenteral administration contains sterile aqueous solutions, non-aqueous solvents, suspensions, emulsions, lyophilized preparations, or suppositories.

For non-aqueous solvents, and suspensions, propylene glycol, polyethylene glycol, vegetable oil such as olive oil, and the injectable ester such as ethyl oleate may be used. For the suppositories, base such as witepsol, macrogol, tween 61, cacao butter, laurinum, glycerol, or gelatin may be used.

The composition according to the present invention is administered in a pharmaceutically effective amount. In the present invention, the expression "pharmaceutically effective amount" refers to a sufficient amount to treat diseases with a reasonably applicable benefit/risk ratio for the medical treatment, and the level of the effective amount may be determined according to type of patient's diseases, severity, drug activity, sensitivity to the drug, administration time, administration route and excretion rate, duration of therapy, concurrent medications used, and other well-known factors in the medical field. The composition according to the present invention may be administered to an individual treatment or in combination with other drugs, may be administered sequentially or simultaneously with conventional treatment, and may be single or multiple doses. It is important to administer the amount to obtain maximum effect with the least amount possible without causing side effect, by considering all the above factors, which may be easily determined by those skilled in the art.

Specifically, according to the present invention, an effective amount of compound may vary depending on the patient's age, sex, or weight, and in general, the effective amount may be 0.1 to 100 mg per 1 kg of body weight, or preferably, 0.5 to 10 mg for daily administration or administration for every other day, or may be 1 to 3 divided doses a day. However, since the effective amount can increase or decrease depending on the route of administration, the severity of obesity, gender, weight, or age, the dose does not in any way constrain the scope of the present invention.

Since the health food composition according to the present invention effectively inhibits lipid metabolism and energy metabolism by effectively inhibiting activity of diacylglycerol acyltransferase (DGAT) which is an inducer of metabolic disease such as obesity, diabetes, hyperlipidemia, or fatty liver, in the process of lipid metabolism, it is possible to add the indole derivative of Formula 1 to health supplements such as food or beverages for the purpose of preventing or enhancing metabolic diseases.

The food is not particularly limited to any specific kind. An example of the food that can be added with the above materials includes drink, meat, sausage, bread, biscuits, cake, chocolate, candies, snacks, cookies, pizza, noodles, other noodles, gums, dairy products including ice cream, various soups, beverages, alcohol drinks and vitamin complexes, milk and dairy products, and all the health functional foods in a general acceptable range.

The indole derivatives of Formula 1 of the present invention may be added to the food as is or used in combination with other food ingredients and used appropriately in accordance with conventional methods. The mixing ratio of the active ingredients may be determined appropriately depending on the purpose of use (i.e., prevention or enhancement). In general, the amount of the chemical compound in the healthy foods may be by 0.1 to 90 parts by weight for total food weight. However, for the purpose of health and hygiene, or for the purpose of long-term intake for health control, the amount may be less than the above range, and since there are no problems in terms of safety, the amount of the active ingredient may be used over the above range.

The functional health beverage composition according to the present invention is not limited otherwise, except that it contains the above compound as an essential ingredient in a prescribed ratio, and it may contain additional ingredient such as various flavors or natural carbohydrates. Examples of the aforementioned natural carbohydrate may include general sugar such as: monosaccharides, for example, glucose, fructose, etc.; disaccharide, for example, maltose, sucrose, etc.;, and poly-saccharide, for example dextrin, cyclodextrin, etc., and sugar alcohol such as xylitol, sorbitol, erythritol, etc.

Additionally, other flavors such as natural flavors (thaumatin, stevia extract (e.g., rebaudioside A, glycyrrhizin, etc.) and synthetic flavoring agents (e.g., saccharin, aspartame, etc.) may be used advantageously. The ratio of the natural carbohydrate may be in a range of about 1 to 20 g per 100 of composition of the present invention, or preferably, about 5 to 12 g.

In addition, the indole derivative of Formula 1 according to the present invention may contain various nutrients, vitamins and minerals (electrolytes), flavors such as synthetic flavors and natural flavors, coloring agents and promoters (cheese, chocolate, etc.), pectic acid and its salts, alginic acid and its salts, organic acid, protective colloidal thickening agent, pH control agents, stabilizers, preservatives, glycerin, alcohol, or carbonate for use in carbonated beverages. The indole derivatives according to the present invention may also contain natural fruit juice and fruit juice and vegetable pulp for the manufacture of vegetable beverages.

These ingredients may be used independently or in combination. The ratio of these additives, although not important, may generally be selected from a range of about 0.1 to 20 parts by weight per 100 parts by weight.

Since the indole derivative represented by Formula 1 according to the present invention can effectively inhibit the activity of diacylglycerol acyltransferase (DGAT), which is the inducer of metabolic diseases in the process of lipid metabolism, and thus can effectively regulate lipid metabolism and energy metabolism, the indole derivative can be advantageously used for the pharmaceutical composition for preventing or treating metabolic diseases such as obesity, diabetes, hyperlipidemia or fatty liver.

EXAMPLES

Hereinafter, the present invention will be explained in more detail with reference to the following Examples. However, the following Examples are only provided only for illustrative purpose, and therefore, do not limit the scope of the present invention.

Example 1

Preparation of (E)-tert-butyl 3-(3-(2-benzoyl-1-isopropylhydrazinyl)-3-oxoprop-1-enyl)-1H-indole-1-carboxylate

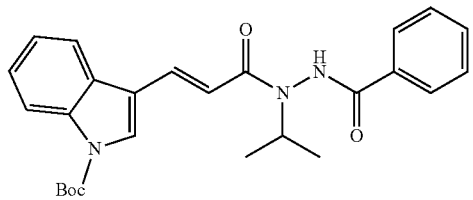 [SMILES: CC(C)N(NC(=O)c1ccccc1)C(=O)/C=C/c1cn(C(=O)OC(C)(C)C)c2ccccc12]

To solution containing (E)-3-(1-(tert-butoxycarbonyl)-1H-indol-3-yl)acrylic acid (1000 mg, 3.48 mmol), N'-isopropylbenzohydrazide (930.51 mg, 5.22 mmol) and HATU (1985.12 mg, 5.22 mmol) dissolved in DMF (15.0 ml), N,N-diisopropylethylamine (DIPEA)(0.90943 ml, 5.22 mmol) was slowly drop-wise added and stirred at room temperature for 12 hr. The reaction mixture was diluted with EtOAc, washed with water and brine, dried with anhydrous $MgSO_4$ filtered, and concentrated under reduced pressure. The residue was separated through silica gel chromatography (n-hexane:EtOAc=3:1) and dried so that ivory (E)-tert-butyl 3-(3-(2-benzoyl-1-isopropylhydrazinyl)-3-oxoprop-1-enyl)-1H-indole-1-carboxylate was obtained as white solid (970 mg, 62.3%).

$^1$H-NMR (DMSO, 500 MHz): δ 10.82 (brs, 1H, —NH), 8.13 (s, 1H, Ind-H), 8.10 (d, J=8.31 Hz, 1H, Ind-H), 7.99 (d, J=7.8 Hz, 2H, Ind-H, Ar—H), 7.74 (d, J=16.13 Hz, 1H, Ind-CH=CH—), 7.68 (d, J=7.33 Hz, 1H, Ind-H), 7.61 (m, 2H, Ar—H), 7.54 (d, J=8.31 Hz, 1H, Ar—H), 7.35 (t, J=7.82 Hz, 1H, Ind-H), 7.08 (t, J=7.33 Hz, 1H, Ind-H), 6.89 (d, J=15.6 Hz, 1H, Ind-CH=CH—), 4.82 (q, J=6.35 Hz, 1H, —NCH(CH$_3$)$_2$), 1.62 (s, 9H, —NCOOC(CH$_3$)$_3$), 1.20 (d, J=6.84 Hz, 3H, —NCH(CH$_3$)$_2$), 1.12 (d, J=6.34 Hz, 3H, —NCH(CH$_3$)$_2$ Example 2

Preparation of (E)-tert-butyl 3-(3-(1-isopropyl-2-picolinoylhydrazinyl)-3-oxoprop-1-enyl)-1H-indole-1-carboxylate

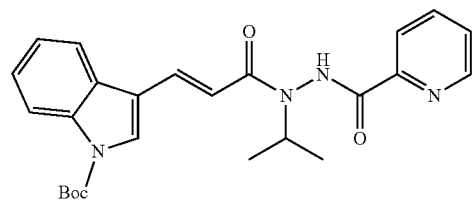 [SMILES: CC(C)N(NC(=O)c1ccccn1)C(=O)/C=C/c1cn(C(=O)OC(C)(C)C)c2ccccc12]

To solution containing (E)-3-(1-(tert-butoxycarbonyl)-1H-indol-3-yl)acrylic acid (200 mg, 0.696 mmol), N'-isopropyl picolino hydrazide (187.14 mg, 1.04 mmol) and HATU (397.02 mg, 1.04 mmol) dissolved in DMF (7.0 ml), N,N-diisopropylethylamine (DIPEA)(0.1819 ml, 1.04 mmol) was slowly drop-wise added and stirred at room temperature for 12 hr. The reaction mixture was diluted with EtOAc, washed with water and brine, dried with anhydrous $MgSO_4$ filtered, filtered, and concentrated under reduced pressure. The residue was separated through silica gel chromatography (n-hexane:EtOAc=3:1) dried so that the ivory (E)-tert-butyl 3-(3-(1-isopropyl-2-picolinoyl hydrazinyl)-3-oxoprop-1-enyl)-1H-indole-1-carboxylate was obtained (108.1 mg, 34.6%).

$^1$H-NMR (DMSO, 500 MHz): δ 11.21 (brs, 1H, —NH), 8.84 (s, 1H, Ind-H), 8.09 (m, 4H, Ar—H), 7.72(t, J=15.65 Hz, 2H, Ind-CH=CH—), 7.50(m, 1H, Ind-H), 7.32 (m, 1H, Ind-H), 6.97 (t, J=16.13 Hz, 1H, Ind-CH=CH—), 4.80 (m, 1H, —NCH(CH$_3$)$_2$), 1.62 (s, 9H, —NCOOC(CH$_3$)$_3$), 1.18 (m, 6H, —NCH(CH$_3$)$_2$)

Example 3

Preparation of (E)-tert-butyl 3-(3-(1-isopropyl-2-nicotinoylhydrazinyl)-3-oxoprop-1-enyl)-1H-indole-1-carboxylate

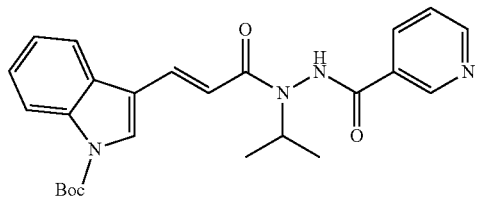 [SMILES: CC(C)N(NC(=O)c1cccnc1)C(=O)/C=C/c1cn(C(=O)OC(C)(C)C)c2ccccc12]

To solution containing (E)-3-(1-(tert-butoxycarbonyl)-1H-indol-3-yl)acrylic acid (200 mg, 0.696 mmol), N'-isopropylnicotino hydrazide (187.14 mg, 1.04 mmol) and HATU (397.02 mg, 1.04 mmol) dissolved in DMF (7.0 ml), N,N-diisopropylethylamine (DIPEA)(0.1819 ml, 1.04 mmol) was slowly drop-wise added and stirred at room temperature for 12 hr. The reaction mixture was diluted with EtOAc, washed with water and brine, dried with anhydrous MgSO₄, filtered, and concentrated under reduced pressure. The residue was separated through silica gel chromatography (n-hexane: EtOAc=3:1) and dried, so that ivory (E)-tert-butyl 3-(3-(1-isopropyl-2-nicotinoyl hydrazinyl)-3-oxoprop-1-enyl)-1H-indole-1-carboxylate was obtained (83 mg, 26.6%).

¹H-NMR (DMSO, 500 MHz): δ 10.98(brs, 1H, —NH), 9.14(s, 1H, aromatic), 8.84(d, J=4.89 Hz, 1H, aromatic) 8.33 (d, J=7.82 Hz, 1H, aromatic), 8.14(s, 1H, aromatic), 8.10(d, J=8.31 Hz, 1H, aromatic), 7.76(d, J=16.65 Hz, 1H, indole-CH=CH—), 7.65(m, 1H, aromatic), 7.55(d, J=7.82 Hz, 1H, aromatic), 7.36(t, J=7.82 Hz, 1H, aromatic), 7.11(t, J=7.33 Hz, 1H, aromatic), 6.90(d, J=15.65 Hz, 1H, indole-CH=CH—), 4.82(q, J=6.84 Hz, 1H, —N—CH—(CH₃)₂), 1.62(s, 9H, Boc), 1.21(d, J=6.84 Hz, 3H, —N—CH—(CH₃)₂), 1.14 (d, J=6.84 Hz, 3H, —N—CH—(CH₃)₂)

Example 4

Preparation of (E)-tert-butyl 3-(3-(2-(3-hydroxybenzoyl)-1-isopropylhydrazinyl)-3-oxoprop-1-enyl)-1H-indole-1-carboxylate

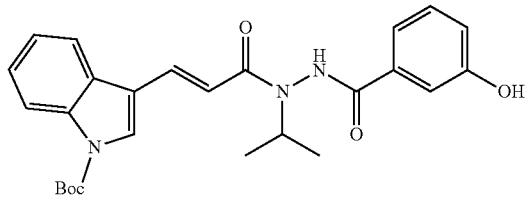 [SMILES: CC(C)N(NC(=O)c1cccc(O)c1)C(=O)/C=C/c1cn(C(=O)OC(C)(C)C)c2ccccc12]

To solution containing (E)-3-(1-(tert-butoxycarbonyl)-1H-indol-3-yl)acrylic acid (200 mg, 0.696 mmol), 3-hydroxy-N'-isopropylbenzohydrazide (202.81 mg, 1.04 mmol) and HATU (397.02 mg, 1.04 mmol) dissolved in DMF (7.0 ml), N,N-diisopropylethylamine (DIPEA) (0.1819 ml, 1.04 mmol) was slowly drop-wise added and stirred at room temperature for 12 hr. The reaction mixture was diluted with EtOAc, washed with water and brine, dried with anhydrous MgSO₄, filtered, and concentrated under reduced pressure. The residue was separated through silica gel chromatography (28% EtOAc) and dried so that ivory (E)-tert-butyl 3-(3-(2-(3-hydroxybenzoyl)-1-isopropylhydrazinyl)-3-oxoprop-1-enyl)-1H-indole-1-carboxylate was obtained (54 mg, 16.7%).

¹H-NMR (DMSO, 500 MHz): δ 10.11(brs, 1H, —NH), 8.13(m, 2H, aromatic), 7.75(d, J=16.62 Hz, 1H, indole-CH=CH—), 7.58(m, 1H, aromatic), 7.40(m, 4H, aromatic), 7.13(m, 2H, aromatic), 6.89(d, J=16.13 Hz, 1H, indole-CH=CH—), 4.82(m, 1H—N—CH—(CH₃)₂), 1.64(s, 9H, Boc), 1.20 (m, 3H, —N—CH—(CH₃)₂), 1.13(m, 3H, —N—CH—(CH₃)₂)

Example 5

Preparation of (E)-tert-butyl 3-(3-(2-(4-hydroxybenzoyl)-1-isopropylhydrazinyl)-3-oxoprop-1-enyl)-1H-indole-1-carboxylate

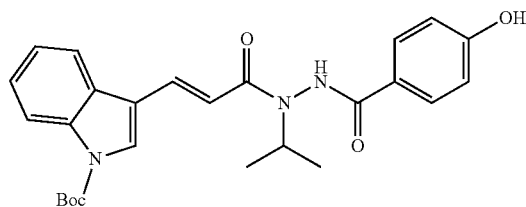 [SMILES: CC(C)N(NC(=O)c1ccc(O)cc1)C(=O)/C=C/c1cn(C(=O)OC(C)(C)C)c2ccccc12]

To solution containing (E)-3-(1-(tert-butoxycarbonyl)-1H-indol-3-yl)acrylic acid (200 mg, 0.696 mmol), 4-hydroxy-N'-isopropylbenzohydrazide (202.81 mg, 1.04 mmol) and HATU (397.02 mg, 1.04 mmol) dissolved in DMF (7.0 ml), N,N-diisopropylethylamine (DIPEA)(0.1819 ml, 1.04 mmol) was slowly drop-wise added and stirred at room temperature for 12 hr. The reaction mixture was diluted with EtOAc, washed with water and brine, dried with anhydrous MgSO₄, filtered, and concentrated under reduced pressure. The residue was separated through silica gel chromatography (40% EtOAc) and dried so that ivory (E)-tert-butyl 3-(3-(2-(4-hydroxybenzoyl)-1-isopropylhydrazinyl)-3-oxoprop-1-enyl)-1H-indole-1-carboxylate was obtained (102.5 mg, 31.8%).

¹H-NMR (DMSO, 500 MHz): δ 10.55 (brs, 1H, —NH), 8.11 (d, J=3.91 Hz, 2H, Ar—H), 7.86~7.88 (m, 2H, Ar—H), 7.73 (d, J=16.13 Hz, 1H, Ind-CH=CH—), 7.52 (d, J=7.34 Hz, 1H, Ind-H), 7.35 (t, J=7.33 Hz, 1H, Ind-H), 7.08 (t, J=7.33 Hz, 1H, Ind-H), 6.93 (t, J=7.82 Hz, 2H, Ind-H), 6.89 (d, J=16.13 Hz, 1H, Ind-CH=CH—), 4.80 (q, J=6.35 Hz, 1H, —NCH(CH₃)₂), 1.63 (s, 9H, —NCOOC(CH₃)₃), 1.19 (d, J=6.35 Hz, 3H, —NCH(CH₃)₂), 1.11 (d, J=6.35 Hz, 3H, —NCH(CH₃)₂)

Example 6

Preparation of (E)-tert-butyl 3-(3-(1-isopropyl-2-(3-methoxybenzoyl)hydrazinyl)-3-oxoprop-1-enyl)-1H-indole-1-carboxylate

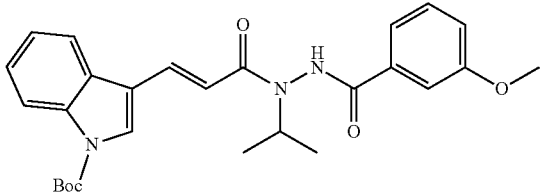 [SMILES: COc1cccc(C(=O)NN(C(=O)/C=C/c2cn(C(=O)OC(C)(C)C)c3ccccc23)C(C)C)c1]

To solution containing (E)-tert-butyl 3-(3-(2-(3-hydroxybenzoyl)-1-isopropylhydrazinyl)-3-oxoprop-1-enyl)-1H-indole-1-carboxylate (100 mg, 0.22 mmol) and K₂CO₃ (35.8 mg, 0.26 mmol) dissolved in anhydrous acetonitrile (10.0 ml), iodomethane (0.0673 ml, 1.08 mmol) was added dropby-drop at 0° C. The reaction mixture was refluxed for 12 hr at 85° C. After concentration under reduced pressure, the solution was separated through the silica gel chromatography (30% EtOAc) so that ivoty solid form of (E)-tert-butyl 3-(3-(1-isopropyl-2-(3-methoxybenzoyl)hydrazinyl)-3-oxoprop-1-enyl)-1H-indole-1-carboxylate was obtained (43.5 mg, 42.2%).

¹H-NMR (DMSO, 500 MHz): δ 10.77(brs, 1H, —NH), 8.12(s, 1H, aromatic), 8.10(d, J=8.31 Hz, 1H, aromatic), 7.74 (d, J=15.65 Hz, 1H, indole-CH═CH—), 7.53(m, 4H, aromatic), 7.35(t, J=7.82 Hz, 1H, aromatic), 7.24(d, J=7.82 Hz, 1H, aromatic), 7.07(t, J=7.82 Hz, 1H, aromatic), 6.89(d, J=16.13 Hz, 1H, indole-CH═CH—), 4.80(q, J=6.35 Hz, 1H, —N—CH—(CH₃)₂), 3.83(s, 3H, —OCH₃), 1.61(s, 9H, Boc), 1.19(d, J=6.84 Hz, 3H, —N—CH—(CH₃)₂), 1.12(d, J=5.86 Hz, 3H, —N—CH—(CH₃)₂)

Example 7

Preparation of (E)-tert-butyl 3-(3-(1-isopropyl-2-(4-methoxybenzoyl)hydrazinyl)-3-oxoprop-1-enyl)-1H-indole-1-carboxylate

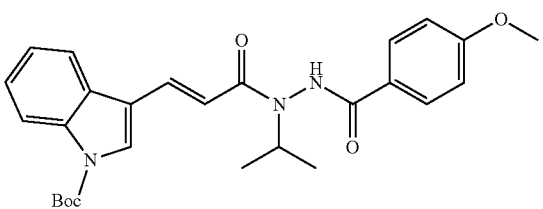 [SMILES: COc1ccc(C(=O)NN(C(=O)/C=C/c2cn(C(=O)OC(C)(C)C)c3ccccc23)C(C)C)cc1]

To solution containing (E)-tert-butyl 3-(3-(2-(4-hydroxybenzoyl)-1-isopropylhydrazinyl)-3-oxoprop-1-enyl)-1H-indole-1-carboxylate (100 mg, 0.22 mmol) and K₂CO₃ (35.8 mg, 0.26 mmol) dissolved in acetone (5.0 ml), iodomethane (0.0673 ml, 1.08 mmol) was added drop-by-drop at 0° C. The reaction mixture was refluxed at 60° C. for 72 hr. After concentration under reduced pressure, the solution was separated through silica gel chromatography (CHCl₃:methanol=70:1) so that ivory solid form of (E)-tert-butyl 3-(3-(1-isopropyl-2-(4-methoxybenzoyl)hydrazinyl)-3-oxoprop-1-enyl)-1H-indole-1-carboxylate was obtained (38.4 mg, 37.2%).

¹H-NMR (DMSO, 500 MHz): δ 10.64(brs, 1H, —NH), 8.09(d, J=8.31 Hz, 2H, aromatic), 7.97(d, J=8.80 Hz, 2H, aromatic), 7.72(d, J=15.65 Hz, 1H, indole-CH═CH—), 7.51 (d, J=7.82 Hz, 1H, aromatic), 7.34(t, J=7.82 Hz, 1H, aromatic), 7.13(d, J=8.80 Hz, 2H, aromatic), 7.09(t, J=7.82 Hz, 1H, aromatic), 6.87(d, J=16.13 Hz, 1H, indole-CH═CH—), 4.80(q, J=6.35 Hz, 1H, —N—CH—(CH₃)₂), 3.85(s, 3H, —OCH₃), 1.61(s, 9H, Boc), 1.18(d, J=6.84 Hz, 3H, —N—CH—(CH₃)₂), 1.10(d, J=6.35 Hz, 3H, —N—CH—(CH₃)₂)

Example 8

Preparation of (E)-tert-butyl 3-(3-(1-isopropyl-2-(3-(2-morpholinoethoxy)benzoyl)hydrazinyl)-3-oxoprop-1-enyl)-1H-indole-1-carboxylate

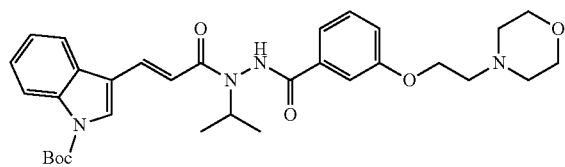 [SMILES: CC(C)N(NC(=O)c1cccc(OCCN2CCOCC2)c1)C(=O)/C=C/c1cn(C(=O)OC(C)(C)C)c2ccccc12]

To solution containing (E)-tert-butyl 3-(3-(2-(3-hydroxybenzoyl)-1-isopropylhydrazinyl)-3-oxoprop-1-enyl)-1H-indole-1-carboxylate (67.3 mg, 0.15 mmol) and K₂CO₃ (40.13 mg, 0.29 mmol) dissolved in anhydrous acetonitrile (10.0 ml), 1,2-dibromoethane (0.0313 ml, 0.36 mmol) was added drop-by-drop. The reaction mixture was refluxed at 80° C. for 48 hr. After concentration under reduced pressure, the solution was separated through silica gel chromatography (n-hexane:EtOAc:methanol=10:3:1) so that ivory solid form of (E)-tert-butyl 3-(3-(2-(3-(2-bromoethoxy)benzoyl)-1-isopropylhydrazinyl)-3-oxoprop-1-enyl)-1H-indole-1-carboxylate was obtained (15 mg, 18.1%). The resultant (E)-tert-butyl 3-(3-(2-(3-(2-bromoethoxy)benzoyl)-1-isopropylhydrazinyl)-3-oxoprop-1-enyl)-1H-indole-1-carboxylate (15.0 mg, 0.026 mmol) and K₂CO₃ (7.27 mg, 0.053 mmol) were dissolved in anhydrous acetonitrile (10.0 ml) and the solution was drop-wise added with morpholine (0.01 ml, 0.053 mmol). The reaction mixture was refluxed at 85° C. for 12 hr. After concentration under reduced pressure, the solution was separated through silica gel chromatography (MC:methanol=24:1) so that ivory solid form of (E)-tert-butyl 3-(3-(1-isopropyl-2-(3-(2-morpholinoethoxy)benzoyl)hydrazinyl)-3-oxoprop-1-enyl)-1H-indole-1-carboxylate was obtained (10.6 mg, 69.9%).

¹H-NMR (DMSO, 500 MHz): δ 10.76(brs, 1H, —NH), 8.12(s, 1H, aromatic), 8.10(d, J=8.31 Hz, 1H, aromatic), 7.74 (d, J=16.13 Hz, 1H, indole-CH═CH—), 7.53(m, 4H, aromatic), 7.35(t, J=7.82 Hz, 1H, aromatic), 7.25(d, J=7.82 Hz, 1H, aromatic), 7.08(t, J=7.82 Hz, 1H, aromatic), 6.89(d, J=16.13 Hz, 1H, indole-CH═CH—), 4.80(q, J=6.84 Hz, 1H, —N—CH—(CH₃)₂), 4.16(t, J=5.86 Hz, 2H, —O—CH₂—CH₂—N), 3.56(t, J=4.40 Hz, 4H, —CH₂—O—CH₂—), 2.71(t, J=5.86 Hz, 2H, —O—CH₂—CH₂—N), 2.46(m, 4H, morpholine), 1.62(s, 9H, Boc), 1.19(d, J=6.35 Hz, 3H, —N—CH—(CH₃)₂), 1.12(d, J=6.84 Hz, 3H, —N—CH—(CH₃)₂)

Example 9

Preparation of (E)-tert-butyl 3-(3-(1-isopropyl-2-(4-(2-morpholinoethoxy)benzoyl)hydrazinyl)-3-oxoprop-1-enyl)-1H-indole-1-carboxylate

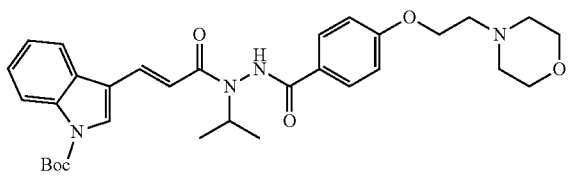 [SMILES: CC(C)N(NC(=O)c1ccc(OCCN2CCOCC2)cc1)C(=O)/C=C/c1cn(C(=O)OC(C)(C)C)c2ccccc12]

(E)-tert-butyl 3-(3-(2-(4-hydroxybenzoyl)-1-isopropylhydrazinyl)-3-oxoprop-1-enyl)-1H-indole-1-carboxylate (50.0 mg, 0.11 mmol) and K₂CO₃ (59.63 mg, 0.43 mmol) dissolved in anhydrous acetonitrile (10.0 ml), 1,2-dibromoethane (0.0465 ml, 0.54 mmol) was added drop-by-drop. The reaction mixture was refluxed at 85° C. for 48 hr. After concentration under reduced pressure, the solution was separated through silica gel chromatography (n-hexane:EtOAc:methanol=14:3:1) so that ivory solid form of (E)-tert-butyl 3-(3-(2-(4-(2-bromoethoxy)benzoyl)-1-isopropylhydrazinyl)-3- oxoprop-1-enyl)-1H-indole-1-carboxylate was obtained.(34 mg, 55.3%). The resultant (E)-tert-butyl 3-(3-(2-(4-(2-bromoethoxy)benzoyl)-1-isopropylhydrazinyl)-3-oxoprop-1-enyl)-1H-indole-1-carboxylate (34.0 mg, 0.06 mmol) and $K_2CO_3$ (16.5 mg, 0.12 mmol) were dissolved in anhydrous acetonitrile (10.0 ml), and the solution was drop-wise added with morpholine (0.01031 ml, 0.053 mmol). The reaction mixture was refluxed at 85° C. for 12 hr. After concentration under reduced pressure, the solution was separated through silica gel chromatography (MC:methanol=30:1) so that ivory solid form of (E)-tert-butyl3-(3-(1-isopropyl-2-(4-(2-morpholinoethoxy)benzoyl)hydrazinyl)-3-oxoprop-1-enyl)-1H-indole-1-carboxylate was obtained (8.2 mg, 23.9%).

$^1$H-NMR (DMSO, 500 MHz): δ 10.64 (brs, 1H, —NH), 8.10 (d, J=7.82 Hz, 2H, aromatic), 7.95 (d, J=8.80 Hz, 2H, aromatic), 7.72 (d, J=16.13 Hz, 1H, indole-C$\underline{H}$=CH—), 7.52 (d, J=7.33 Hz, 1H, aromatic), 7.34 (t, J=7.82 Hz, 1H, aromatic), 7.14 (d, J=8.80 Hz, 2H, aromatic), 7.08 (t, J=8.31 Hz, 1H, aromatic), 6.87 (d, J=16.13 Hz, 1H, indole-CH=C$\underline{H}$—), 4.79 (q, J=6.84 Hz, 1H, —N—C$\underline{H}$—(CH$_3$)$_2$), 4.21 (t, J=5.86 Hz, 2H, —O—C$\underline{H}_2$—CH$_2$—N), 3.60 (t, J=4.40 Hz, 4H, —C$\underline{H}_2$—O—C$\underline{H}_2$), 2.73 (t, J=5.86 Hz, 3H, morpholine), 2.63 (m, 2H, —O—CH$_2$—C$\underline{H}_2$—N), 2.36 (m, 1H, morpholine), 1.61 (s, 9H, Boc), 1.19 (d, J=6.35 Hz, 3H, —N—CH—(C$\underline{H}_3$)$_2$), 1.10 (d, J=6.35 Hz, 3H, —N—CH—(C$\underline{H}_3$)$_2$)

EXAMPLE 10

Preparation of (E)-tert-butyl 3-(3-(1-isopropyl-2-(3-(2-methoxyethoxy)benzoyl)hydrazinyl)-3-oxoprop-1-enyl)-1H-indole-1-carboxylate

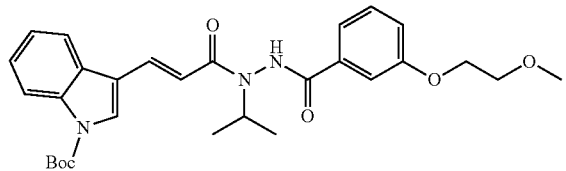 [SMILES: COCCOc1cccc(C(=O)NN(C(=O)/C=C/c2cn(C(=O)OC(C)(C)C)c3ccccc23)C(C)C)c1]

To solution containing (E)-tert-butyl 3-(3-(2-(3-hydroxybenzoyl)-1-isopropylhydrazinyl)-3-oxoprop-1-enyl)-1H-indole-1-carboxylate (100.0 mg, 0.22 mmol) and $K_2CO_3$ (35.8 mg, 0.26 mmol) dissolved in acetone (5.0 ml), 1-bromo-2-methoxyethane (0.024 ml, 0.26 mmol) was added drop-wise. The reaction mixture was refluxed at 60° C. for 48 hr. After concentration under reduced pressure, the solution was separated through silica gel chromatography (CHCl$_3$:methanol=60:1) so that ivory solid form of (E)-tert-butyl 3-(3-(1-isopropyl-2-(3-(2-methoxyethoxy)benzoyl)hydrazinyl)-3-oxoprop-1-enyl)-1H-indole-1-carboxylate was obtained (62.4 mg, 55.5%).

$^1$H-NMR (DMSO, 500 MHz): δ 10.75 (brs, 1H, —NH), 8.11 (s, 1H, aromatic), 8.10 (d, J=8.31 Hz, 1H, aromatic), 7.73 (d, J=16.13 Hz, 1H, indole-C$\underline{H}$=CH—), 7.53 (m, 4H, aromatic), 7.35 (t, J=7.82 Hz, 1H, aromatic), 7.25 (d, J=7.82 Hz, 1H, aromatic), 7.09 (t, J=7.82 Hz, 1H, aromatic), 6.89 (d, J=16.13 Hz, 1H, indole-CH=C$\underline{H}$—), 4.80 (q, J=6.84 Hz, 1H, —N—C$\underline{H}$—(CH$_3$)$_2$), 4.17 (t, J=4.40 Hz, 2H, —O—(C$\underline{H}_2$)$_2$—O—CH$_3$), 3.68 (t, J=4.40 Hz, 2H, —O—(C$\underline{H}_2$)$_2$—O—CH$_3$), 3.31 (s, 3H, —OCH$_3$), 1.61 (s, 9H, Boc), 1.19 (d, J=6.35 Hz, 3H, —N—CH—(C$\underline{H}_3$)$_2$), 1.12 (d, J=6.84 Hz, 3H, —N—CH—(C$\underline{H}_3$)$_2$)

Example 11

Preparation of (E)-tert-butyl 3-(3-(1-isopropyl-2-(4-(2-methoxyethoxy)benzoyl)hydrazinyl)-3-oxoprop-1-enyl)-1H-indole-1-carboxylate

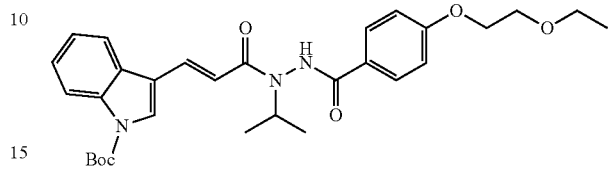

To solution containing (E)-tert-butyl 3-(3-(1-isopropyl-2-(4-methoxybenzoyl)hydrazinyl)-3-oxoprop-1-enyl)-1H-indole-1-carboxylate (100.0 mg, 0.22 mmol) and $K_2CO_3$ (35.8 mg, 0.26 mmol) dissolved in acetone (5.0 ml), 1-bromo-2-methoxyethane (0.024 ml, 0.26 mmol) was added drop-wise. The reaction mixture was refluxed at 60° C. for 48 hr. After concentration under reduced pressure, the solution was separated through silica gel chromatography (CHCl$_3$: methanol=65:1) so that ivory solid form of (E)-tert-butyl 3-(3-(1-isopropyl-2-(4-(2-methoxyethoxy)benzoyl)hydrazinyl)-3-oxoprop-1-enyl)-1H-indole-1-carboxylate was obtained (66.4 mg, 59%).

$^1$H-NMR (DMSO, 500 MHz): δ 10.64 (brs, 1H, —NH), 8.10 (s, 1H, aromatic), 8.08 (m, 1H, aromatic), 7.95 (d, J=8.80 Hz, 2H, aromatic), 7.72 (d, J=15.65 Hz, 1H, indole-C$\underline{H}$=CH—), 7.51 (d, J=7.82 Hz, 1H, aromatic), 7.34 (t, J=7.82 Hz, 1H, aromatic), 7.14 (d, J=8.31 Hz, 2H, aromatic), 7.08 (t, J=7.82 Hz, 1H, aromatic), 6.87 (d, J=16.13 Hz, 1H, indole-CH=C$\underline{H}$—), 4.79 (q, J=6.84 Hz, 1H, —N—C$\underline{H}$—(CH$_3$)$_2$), 4.21 (t, J=4.89 Hz, 2H, —O—(C$\underline{H}_2$)$_2$—O—CH$_3$), 3.69 (t, J=4.89 Hz, 2H, —O—(C$\underline{H}_2$)$_2$—O—CH$_3$), 3.32 (s, 3H, —OC$\underline{H}_3$), 1.61 (s, 9H, Boc), 1.18 (d, J=6.35 Hz, 3H, —N—CH—(C$\underline{H}_3$)$_2$), 1.10 (d, J=6.84 Hz, 3H, —N—CH—(C$\underline{H}_3$)$_2$)

Example 12

Preparation of (E)-tert-butyl 3-(3-(2-(3-bromobenzoyl)-1-isopropylhydrazinyl)-3-oxoprop-1-enyl)-1H-indole-1-carboxylate

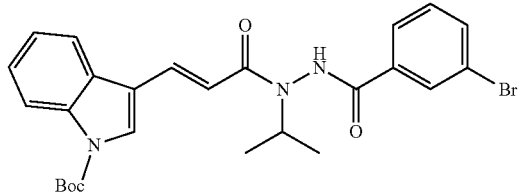 [SMILES: CC(C)N(NC(=O)c1cccc(Br)c1)C(=O)/C=C/c1cn(C(=O)OC(C)(C)C)c2ccccc12]

To solution containing (E)-3-(1-(tert-butoxycarbonyl)-1H-indol-3-yl)acrylic acid (100 mg, 0.35 mmol), 3-bromo-N'-isopropylbenzohydrazide (134.24 mg, 0.52 mmol) and HATU (198.5 mg, 0.52 mmol) dissolved in DMF (4.0 ml), N,N-diisopropylethylamine (DIPEA)(0.09094 ml, 0.52 mmol) was slowly drop-wise added and stirred at room temperature for 12 hr. The reaction mixture was diluted with EtOAc, washed with water and brine, dried with anhydrous $MgSO_4$, filtered, and concentrated under reduced pressure. The residue was separated through silica gel chromatography (n-hexane:EtOAc=3:1) and dried so that ivory (E)-tert-butyl 3-(3-(2-(3-bromobenzoyl)-1-isopropylhydrazinyl)-3-oxoprop-1-enyl)-1H-indole-1-carboxylate was obtained (53.6 mg, 29.3%).

$^1$H-NMR (DMSO, 500 MHz): δ 10.89 (brs, 1H, —NH), 8.16 (s, 1H, aromatic), 8.13 (s, 1H, aromatic), 8.10 (d, J=8.31 Hz, 1H, aromatic), 7.96 (d, J=7.82 Hz, 1H, aromatic), 7.89 (d, J=7.82 Hz, 1H, aromatic), 7.74 (d, J=15.65 Hz, 1H, indole-CH=CH—), 7.56 (q, J=7.82 Hz, 2H, aromatic), 7.38 (t, J=7.82 Hz, 1H, aromatic), 7.14 (t, J=7.82 Hz, 1H, aromatic), 6.88 (d, J=16.13 Hz, 1H, indole-CH=CH—), 4.82 (q, J=6.84 Hz, 1H, —N—CH—(CH$_3$)$_2$), 1.61 (s, 9H, Boc), 1.19 (d, J=6.84 Hz, 3H, —N—CH—(CH$_3$)$_2$), 1.12 (d, J=6.84 Hz, 3H, —N—CH—(CH$_3$)$_2$)

Example 13

Preparation of (E)-tert-butyl 3-(3-(2-(4-bromobenzoyl)-1-isopropylhydrazinyl)-3-oxoprop-1-enyl)-1H-indole-1-carboxylate

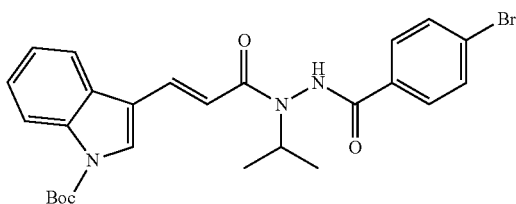 [SMILES: CC(C)N(NC(=O)c1ccc(Br)cc1)C(=O)/C=C/c1cn(C(=O)OC(C)(C)C)c2ccccc12]

To solution containing (E)-3-(1-(tert-butoxycarbonyl)-1H-indol-3-yl)acrylic acid (100 mg, 0.35 mmol), 4-bromo-N'-isopropylbenzohydrazide (134.24 mg, 0.52 mmol) and HATU (198.5 mg, 0.52 mmol) dissolved in DMF (4.0 ml), N,N-diisopropylethylamine (DIPEA)(0.09094 ml, 0.52 mmol) was slowly drop-wise added and stirred at room temperature for 12 hr. The reaction mixture was diluted with EtOAc, washed with water and brine, dried with anhydrous $MgSO_4$, filtered, and concentrated under reduced pressure. The residue was separated through silica gel chromatography (n-hexane:EtOAc=3:1) and dried so that ivory (E)-tert-butyl 3-(3-(2-(4-bromobenzoyl)-1-isopropylhydrazinyl)-3-oxoprop-1-enyl)-1H-indole-1-carboxylate was obtained (85.5 mg, 46.7%).

$^1$H-NMR (DMSO, 500 MHz): δ 10.86 (brs, 1H, —NH), 8.11 (s, 1H, aromatic), 8.10 (d, J=8.31 Hz, 1H, aromatic), 7.92 (d, J=8.80 Hz, 2H, aromatic), 7.83 (d, J=8.31 Hz, 2H, aromatic), 7.74 (d, J=15.65 Hz, 1H, indole-CH=CH—), 7.52 (d, J=7.82 Hz, 1H, aromatic), 7.36 (t, J=7.82 Hz, 1H, aromatic), 7.12 (t, J=7.33 Hz, 1H, aromatic), 6.85 (d, J=15.65 Hz, 1H, indole-CH=CH—), 4.80 (q, J=6.48 Hz, 1H, —N—CH—(CH$_3$)$_2$), 1.61 (s, 9H, Boc), 1.19 (d, J=6.35 Hz, 3H, —N—CH—(CH$_3$)$_2$), 1.11 (d, J=6.84 Hz, 3H, —N—CH—(CH$_3$)$_2$ Example 14

Preparation of (E)-tert-butyl 3-(3-(2-(4-chlorobenzoyl)-1-isopropylhydrazinyl)-3-oxoprop-1-enyl)-1H-indole-1-carboxylate

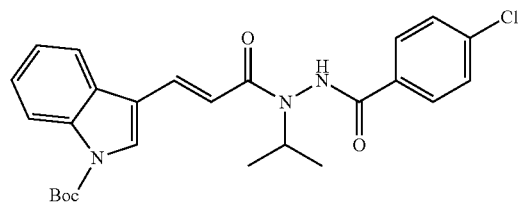 [SMILES: CC(C)N(NC(=O)c1ccc(Cl)cc1)C(=O)/C=C/c1cn(C(=O)OC(C)(C)C)c2ccccc12]

To solution containing (E)-3-(1-(tert-butoxycarbonyl)-1H-indol-3-yl)acrylic acid (200 mg, 0.7 mmol), 4-chloro-N'-isopropylbenzohydrazide (222.07 mg, 1.04 mmol) and HATU (397.02 mg, 1.04 mmol) dissolved in DMF (7.0 ml), N,N-diisopropylethylamine (DIPEA)(0.1819 ml, 1.04 mmol) was slowly drop-wise added and stirred at room temperature for 12 hr. The reaction mixture was diluted with EtOAc, washed with water and brine, dried with anhydrous $MgSO_4$, filtered, and concentrated under reduced pressure. The residue was separated through silica gel chromatography (40% EtOAc) and dried so that ivory ((E)-tert-butyl 3-(3-(2-(4-chlorobenzoyl)-1-isopropylhydrazinyl)-3-oxoprop-1-enyl)-1H-indole-1-carboxylate was obtained (165.6 mg, 49%).

$^1$H-NMR (DMSO, 500 MHz): δ 10.87 (brs, 1H, —NH), 8.12 (s, 1H, aromatic), 8.10 (d, J=8.31 Hz, 1H, aromatic), 8.00 (d, J=8.31 Hz, 2H, aromatic), 7.74 (d, J=15.65 Hz, 1H, indole-CH=CH—), 7.69 (d, J=8.31 Hz, 2H, aromatic), 7.52 (d, J=7.82 Hz, 1H, aromatic), 7.36 (t, J=7.33 Hz, 1H, aromatic), 7.11 (t, J=7.33 Hz, 1H, aromatic), 6.86 (d, J=16.13 HZ, 1H, INDOLE-CH=CH—), 4.80 (Q, J=6.84 Hz, 1H, —N—CH—(CH$_3$)$_2$), 1.61 (s, 9H, Boc), 1.19 (d, J=5.86 Hz, 3H, —N—CH—(CH$_3$)$_2$), 1.11 (d, J=5.38 Hz, 3H, —N—CH—(CH$_3$)$_2$)

Example 15

Preparation of (E)-tert-butyl 3-(3-(2-(3-fluorobenzoyl)-1-isopropylhydrazinyl)-3-oxoprop-1-enyl)-1H-indole-1-carboxylate

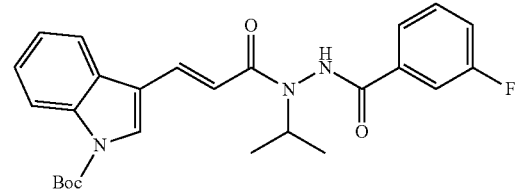 [SMILES: CC(C)N(NC(=O)c1cccc(F)c1)C(=O)/C=C/c1cn(C(=O)OC(C)(C)C)c2ccccc12]

To solution containing 3-(1H-indol-3-yl)-acrylic acid 3-(1H-indol-3-yl)-acrylic acid (200 mg, 0.7 mmol), 3-fluoro-N'-isopropylbenzohydrazide (204.9 mg, 1.04 mmol) and HATU (397.02 mg, 1.04 mmol) dissolved in DMF (7.0 ml), N,N-diisopropylethylamine (DIPEA)(0.1819 ml, 1.04 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (36% EtOAc) and dried so that ivory (E)-tert-butyl 3-(3-(2-(3-fluorobenzoyl)-1-isopropylhydrazinyl)-3-oxoprop-1-enyl)-1H-indole-1-carboxylate was obtained (159.5 mg, 49%).

$^1$H-NMR (DMSO, 500 MHz): δ 10.88 (brs, 1H, —NH), 8.13 (s, 1H, aromatic), 8.10 (d, J=8.80 Hz, 1H, aromatic), 7.84 (d, J=7.82 Hz, 1H, aromatic), 7.78 (d, J=8.80 Hz, 1H, aromatic), 7.74 (d, J=15.65 Hz, 1H, indole-CH=CH—), 7.67 (m, 1H, aromatic), 7.55 (t, J=8.31 Hz, 2H, aromatic), 7.35 (t, J=7.82 Hz, 1H, aromatic), 7.09 (t, J=7.82 Hz, 1H, aromatic), 6.88 (d, J=16.13 Hz, 1H, indole-CH=CH—), 4.81 (q, J=6.48 Hz, 1H, —N—CH—(CH$_3$)$_2$), 1.61 (s, 9H, Boc), 1.19 (d, J=6.84 Hz, 3H, —N—CH—(CH$_3$)$_2$), 1.12 (d, J=6.84 Hz, 3H, —N—CH—(CH$_3$)$_2$)

Example 16

Preparation of (E)-tert-butyl 3-(3-(2-benzoylhydrazinyl)-3-oxoprop-1-enyl)-1H-indole-1-carboxylate

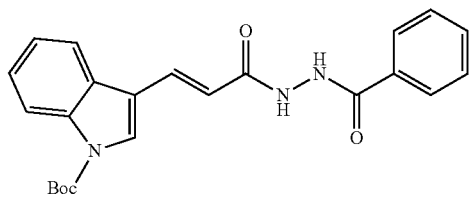 [SMILES: CC(C)(C)OC(=O)n1cc(/C=C/C(=O)NNC(=O)c2ccccc2)c2ccccc21]

To solution containing (E)-3-(1-(tert-butoxycarbonyl)-1H-indol-3-yl)acrylic acid (200 mg, 0.7 mmol), benzohydrazide (142.2 mg, 1.04 mmol) and HATU (397.02 mg, 1.04 mmol) dissolved in DMF (7.0 ml), N,N-diisopropylethylamine (DIPEA)(0.1819 ml, 1.04 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (n-hexane:EtOAc=3:1) and dried so that ivory (E)-tert-butyl 3-(3-(2-benzoyl hydrazinyl)-3-oxoprop-1-enyl)-1H-indole-1-carboxylate was obtained (223.5 mg, 79.2%).

$^1$H-NMR (DMSO, 500 MHz): δ 8.20 (s, 1H, aromatic), 8.17 (d, J=7.33 Hz, 1H, aromatic), 8.01 (d, J=8.07 Hz, 1H, aromatic), 7.93 (d, J=7.33 Hz, 2H, aromatic), 7.76 (d, J=16.13 Hz, 1H, 1H, indole-CH=CH—), 7.59 (t, J=6.60 Hz, 1H, aromatic), 7.52 (t, J=8.07 Hz, 2H, aromatic), 7.45 (m, 2H, aromatic), 6.98 (d, J=16.13 Hz, 1H, indole-CH=CH—), 1.65 (s, 9H, Boc)

Example 17

Preparation of (E)-tert-butyl 3-(3-oxo-3-(2-(phenylsulfonyl)hydrazinyl)prop-1-enyl)-1H-indole-1-carboxylate

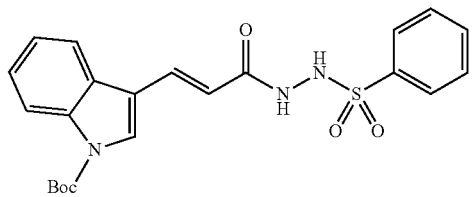 [SMILES: CC(C)(C)OC(=O)n1cc(/C=C/C(=O)NNS(=O)(=O)c2ccccc2)c2ccccc21]

To solution containing (E)-3-(1-(tert-butoxycarbonyl)-1H-indol-3-yl)acrylic acid (200 mg, 0.7 mmol), benzenesulfono hydrazide (179.8 mg, 1.04 mmol) and HATU (397.02 mg, 1.04 mmol) dissolved in DMF (7.0 ml), N,N-diisopropylethylamine (DIPEA)(0.1819 ml, 1.04 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (n-hexane:EtOAc=2:1) and dried so that ivory (E)-tert-butyl 3-(3-oxo-3-(2-(phenylsulfonyl)hydrazinyl)prop-1-enyl)-1H-indole-1carboxylate was obtained (56.2 mg, 16.7%).

$^1$H-NMR (DMSO, 500 MHz): δ 8.14 (d, J=8.80 Hz, 2H, aromatic), 7.91 (d, J=8.07 Hz, 1H, aromatic), 7.86 (d, J=7.33 Hz, 2H, aromatic), 7.65 (t, J=7.33 Hz, 1H, aromatic), 7.58 (t, J=7.33 Hz, 3H, aromatic), 7.44 (t, J=8.07 Hz, 1H, aromatic), 7.38 (t, J=7.33 Hz, 1H, aromatic), 6.75 (d, J=16.13 Hz, 1H, indole-CH=CH—), 1.63 (s, 9H, Boc)

Example 18

Preparation of (E)-tert-butyl 3-(3-(1-isopropyl-2-(3-(2-methoxy-2-oxoethoxy)benzoyphydrazinyl)-3-oxoprop-1-enyl)-1H-indole-1-carboxylate

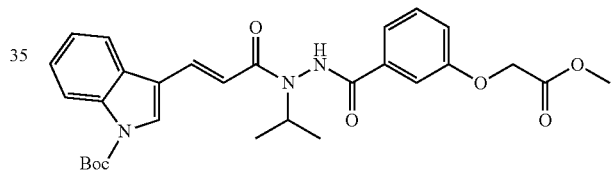

To solution containing (E)-tert-butyl 3-(3-(2-(3-hydroxybenzoyl)-1-isopropylhydrazinyl)-3-oxoprop-1-enyl)-1H-indole-1-carboxylate (1000.0 mg, 2.16 mmol) and K$_2$CO$_3$ (1192.6 mg, 8.63 mmol) dissolved in DMF (15 ml), methyl 2-bromoacetate (0.24506 ml, 2.59 mmol) was drop-wise added. The reaction mixture was refluxed at 60° C. for 24 hr. After concentration under reduced pressure, the solution was separated through silica gel chromatography (n-hexane:EtOAc=90:70) so that yellow solid form of (E)-tert-butyl 3-(3-(1-isopropyl-2-(3-(2-methoxy-2-oxoethoxy)benzoyl)hydrazinyl)-3-oxoprop-1-enyl)-1H-indole-1-carboxylate was obtained (378.6 mg, 33%).

$^1$H-NMR (DMSO, 500 MHz): δ 10.78 (brs, 1H, —NH), 8.12 (s, 1H, aromatic), 8.10 (d, J=8.80 Hz, 1H, aromatic), 7.74 (d, J=15.65 Hz, 1H, indole-CH=CH—), 7.59 (d, J=7.33 Hz, 1H, aromatic), 7.55 (d, J=8.31 Hz, 1H, aromatic), 7.51 (m, 2H, aromatic), 7.35 (t, J=7.82 Hz, 1H, aromatic), 7.24 (d, J=8.80 Hz, 1H, aromatic), 7.11 (t, J=7.82 Hz, 1H, aromatic), 6.88 (d, J=15.65 Hz, 1H, indole-CH=CH—), 4.90 (s, 2H, —O—CH$_2$—COO—), 4.80 (q, J=6.84 Hz, 1H, —N—CH—(CH$_3$)$_2$), 3.69 (s, 3H, —COO—CH$_3$), 1.61 (s, 9H, Boc), 1.19 (d, J=6.35 Hz, 3H, —N—CH—(CH$_3$)$_2$), 1.11 (d, J=6.35 Hz, 3H, —N—CH—(CH$_3$)$_2$)

Example 19

Preparation of (E)-2-(3-(2-(3-(1-(tert-butoxycarbonyl)-1H-indol-3-yl)acryloyl)-2-isopropylhydrazinecarbonyl)phenoxy)acetic acid

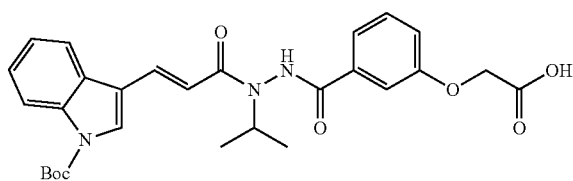 [SMILES: CC(C)N(NC(=O)c1cccc(OCC(=O)O)c1)C(=O)/C=C/c1cn(C(=O)OC(C)(C)C)c2ccccc12]

(E)-tert-butyl 3-(3-(1-isopropyl-2-(3-(2-methoxy-2-oxoethoxy)benzoyl)hydrazinyl)-3-oxoprop-1-enyl)-1H-indole-1-carboxylate (70 mg, 0.13 mmol) was dissolved in THF/H$_2$O (2 ml/1 ml), stirred for 20 min, lithiumhydroxide (10.96 mg, 0.26 mmol) was slowly drop-wise added, and stirred at room temperature for 12 hr. THF was concentrated under reduced pressure, and after titration with 6N HCl at pH=2, the reaction mixture was diluted with EtOAc, washed with water and brine, dried with anhydrous MgSO$_4$ filtered, and concentrated under reduced pressure so that while solid form of (E)-2-(3-(2-(3-(1-(tert-butoxycarbonyl)-1H-indol-3-yl)acryloyl)-2-isopropylhydrazinecarbonyl)phenoxy)acetic acid was obtained (68.1 mg, 99%).

$^1$H-NMR (DMSO, 500 MHz): δ 10.76 (brs, 1H, —NH), 8.09 (s, 1H, aromatic), 8.07 (d, J=7.82 Hz, 1H, aromatic), 7.72 (d, J=15.65 Hz, 1H, indole-CH=CH—), 7.52 (m, 4H, aromatic), 7.32 (t, J=7.33 Hz, 1H, aromatic), 7.23 (d, J=8.80 Hz, 1H, aromatic), 7.09 (t, J=8.31 Hz, 1H, aromatic), 6.87 (d, J=15.65 Hz, 1H, indole-CH=CH—), 4.78 (q, J=6.84 Hz, 1H, —N—CH—(CH$_3$)$_2$), 4.49 (s, 2H, —O—CH$_2$—COOH), 1.59 (s, 9H, Boc), 1.17 (d, J=4.89 Hz, 3H, —N—CH—(CH$_3$)$_2$), 1.09 (d, J=3.91 Hz, 3H, —N—CH—(CH$_3$)$_2$)

Example 20

Preparation of (E)-tert-butyl 3-(3-(2-(3-(2-amino-2-oxoethoxy)benzoyl)-1-isopropylhydrazinyl)-3-oxoprop-1-enyl)-1H-indole-1-carboxylate

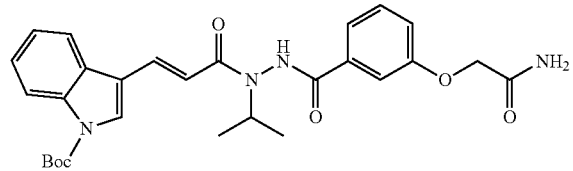 [SMILES: CC(C)N(NC(=O)c1cccc(OCC(N)=O)c1)C(=O)/C=C/c1cn(C(=O)OC(C)(C)C)c2ccccc12]

A 2-neck round bottom flask filled with methanol 10 ml was connected to reflux tube filled with acetone and dry ice, and NH$_3$ gas was bubbled. 3-(3-(1-isopropyl-2-(3-(2-methoxy-2-oxoethoxy)benzoyl)hydrazinyl)-3-oxoprop-1-enyl)-1H-indole-1-carboxylate was introduced into conical tube and dissolved in methanol, and transferred to the round bottom flask with bubbled NH$_3$ gas and stirred at room temperature for 12 hr. After methanol was concentrated under reduced pressure, and silica gel chromatography (n-hexane:EtOAc:methanol=8:3:1), ivory solid form of (E)-tert-butyl 3-(3-(2-(3-(2-amino-2-oxoethoxy)benzoyl)-1-isopropylhydrazinyl)-3-oxoprop-1-enyl)-1H-indole-1-carboxylate was obtained (37.9 mg, 78%).

$^1$H-NMR (DMSO, 500 MHz): δ 10.78 (brs, 1H, —NH), 8.08 (m, 2H, aromatic), 7.70 (d, J=16.13 Hz, 1H, indole-CH=CH—), 7.55 (d, J=8.80 Hz, 1H, aromatic), 7.42 (m, 4H, aromatic), 7.32 (m, 2H, —NH$_2$), 7.13 (t, J=8.80 Hz, 1H, aromatic), 7.08 (m, 1H, aromatic), 6.87 (d, J=15.65 Hz, 1H, indole-CH=CH—), 4.76 (q, J=6.84 Hz, 1H, —N—CH—(CH$_3$)$_2$), 4.19 (s, 2H, —O—CH$_2$—CO—NH$_2$), 1.59 (s, 9H, Boc), 1.16 (d, J=6.35 Hz, 3H, —N—CH—(CH$_3$)$_2$), 1.09 (d, J=5.38 Hz, 3H, —N—CH—(CH$_3$)$_2$)

Example 21

Preparation of N'-(3-(1-benzyl-1H-indol-3-yl)propanoyl)-N'-isopropylbenzohydrazide

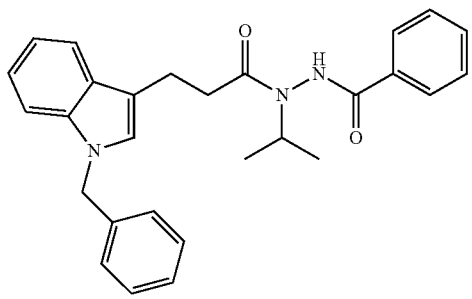 [SMILES: CC(C)N(NC(=O)c1ccccc1)C(=O)CCc1cn(Cc2ccccc2)c2ccccc12]

To solution containing 3-(1H-indol-3-yl)propanoic acid (200 mg, 1.06 mmol), N'-isopropylbenzohydrazide (283.4 mg, 1.59 mmol) and HATU (604.6 mg, 1.59 mmol) dissolved in DMF (7.0 ml), N,N-diisopropylethylamine (DIPEA) (0.277 ml, 1.59 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (n-hexane:EtOAc:methanol=20:3:1) and dried so that white solid form of N'-(3-(1H-indol-3-yl)propanoyl)-N'-isopropylbenzohydrazide was obtained (350 mg, 95%). In 2-neck round bottom flask, NaH (5.5 mg, 0.23 mmol) dissolved in DMF at 0° C. was stirred, and solution containing N'-(3-(1H-indol-3-yl)propanoyl)-N'-isopropylbenzohydrazide (20 mg, 0.06 mmol) dissolved in DMF was transported and stirred at 0° C. for 30. The reaction mixture was drop-wise added with (bromomethyl)benzene (0.01634 ml, 0.14 mmol), and stirred at 80° C. for 1 hr. The reaction mixture was diluted with EtOAc, washed with water and brine, dried with anhydrous MgSO$_4$, filtered, and concentrated under reduced pressure. The residue was separated through silica gel chromatography (n-hexane:EtOAc=2:1) and dried so that ivory solid form of N'-(3-(1-benzyl-1H-indol-3-yl)propanoyl)-N'-isopropylbenzohydrazide was obtained (5 mg, 20%).

$^1$H-NMR (DMSO, 500 MHz): δ 10.55 (brs, 1H, —NH), 7.91 (s, 1H, aromatic), 7.84 (d, J=6.84 Hz, 2H, aromatic), 7.56 (t, J=6.84 Hz, 1H, aromatic), 7.47 (t, J=7.82 Hz, 2H, aromatic), 7.40 (d, J=7.82 Hz, 2H, aromatic), 7.32 (d, J=8.31 Hz, 1H, aromatic), 7.20 (m, 5H, aromatic), 7.10 (d, J=7.82 Hz, 2H, aromatic), 6.99 (t, J=7.33 Hz, 1H, aromatic), 6.86 (t, J=7.33 Hz, 1H, aromatic), 5.26 (s, 2H, —N—CH$_2$-Benzene), 4.67 (q, J=6.35 Hz, 1H, —N—CH—(CH$_3$)$_2$), 2.69 (m, 2H, —CH₂—CH₂—), 2.46 (m, 2H, —CH₂—CH₂—), 1.09 (d, J=6.35 Hz, 3H, —N—CH—(CH₃)₂), 1.02 (d, J=6.84 Hz, 3H, —N—CH—(CH₃)₂)

Example 22

Preparation of (E)-N'-(3-(1H-indol-3-yl)acryloyl)-N'-isopropylbenzohydrazide

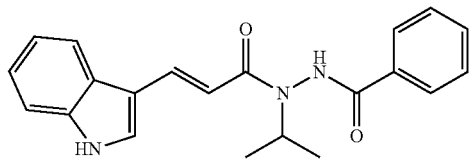 [SMILES: CC(C)N(NC(=O)c1ccccc1)C(=O)/C=C/c1c[nH]c2ccccc12]

To solution containing (E)-3-(1H-indol-3-yl)acrylic acid (200 mg, 1.06 mmol), N'-isopropylbenzohydrazide (283.4 mg, 1.59 mmol) and HATU (604.6 mg, 1.59 mmol) dissolved in DMF (7.0 ml), N,N-diisopropylethylamine (DIPEA) (0.277 ml, 1.59 mmol) was slowly drop-wise added and stirred at room temperature for 12 hr. The reaction mixture was diluted with EtOAc, washed with water and brine, dried with anhydrous MgSO₄, filtered, and concentrated under reduced pressure. The residue was separated through silica gel chromatography (n-hexane:EtOAc:methanol=15:3:1) and dried so that white solid form of (E)-N'-(3-(1H-indol-3-yl)acryloyl)-N'-isopropylbenzohydrazide was obtained (327 mg, 88%).

¹H-NMR (DMSO, 500 MHz): δ 11.06 (brs, 1H, aromatic), 10.73 (brs, 1H, —N—NH—CO—), 7.98 (m, 2H, aromatic), 7.71 (m, 5H, aromatic), 7.41 (m, 2H, aromatic), 7.11 (m, 1H, aromatic), 6.87 (m, 1H, aromatic), 6.71 (d, J=15.65 Hz, indole-CH=CH—), 4.81 (m, 1H, —N—CH—(CH₃)₂), 1.18 (m, 6H, —N—CH—(CH₃)₂)

Example 23

Preparation of N'-(3-(1H-indol-3-yl)propanoyl)-N'-isopropylbenzohydrazide

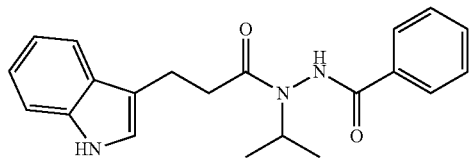 [SMILES: CC(C)N(NC(=O)c1ccccc1)C(=O)CCc1c[nH]c2ccccc12]

To solution containing 3-(1H-indol-3-yl)propanoic acid (200 mg, 1.06 mmol), N'-isopropylbenzohydrazide (283.4 mg, 1.59 mmol) and HATU (604.6 mg, 1.59 mmol) dissolved in DMF (7.0 ml), N,N-diisopropylethylamine (DIPEA) (0.277 ml, 1.59 mmol) was slowly drop-wise added and stirred at room temperature for 12 hr. The reaction mixture was diluted with EtOAc, washed with water and brine, dried with anhydrous MgSO₄, filtered, and concentrated under reduced pressure. The residue was separated through silica gel chromatography (n-hexane:EtOAc:methanol=20:3:1) and dried so that white solid form of N'-(3-(1H-indol-3-yl)propanoyl)-N'-isopropylbenzohydrazide was obtained (327 mg, 88%).

¹H-NMR (CDCl₃, 500 MHz): δ 8.38 (brs, 1H, —NH), 8.28 (s, 1H, Ind-H), 7.92 (s, 1H, Ind-H), 7.64 (m, 2H, Ar—H), 7.50 (t, J=7.34 Hz, 1H, Ar—H), 7.43 (d, J=7.82 Hz, 1H, Ind-H), 7.30 (m, 1H, Ar—H), 7.11 (t, J=7.82 Hz, 1H, Ar—H), 6.93 (t, J=7.82 Hz, 1H, Ind-H), 6.83 (s, 1H, Ind-H), 4.86 (q, J=6.35 Hz, 1H, —NCH(CH₃)₂), 2.89 (dd, 2H, —CH₂—CH₂—), 2.81 (dd, 2H, —CH₂—CH₂—), 1.11 (d, J=6.35 Hz, 3H, —NCH(CH₃)₂, 1.03 (d, J=6.35 Hz, 3H, —NCH(CH₃)₂)

Example 24

Preparation of tert-butyl 3-(3-(2-benzoyl-1-isopropylhydrazinyl)-3-oxopropyl)-1H-indole-1-carboxylate

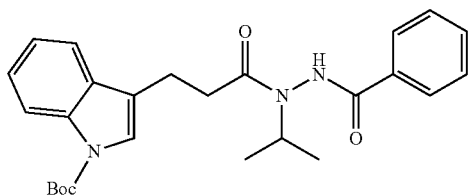 [SMILES: CC(C)N(NC(=O)c1ccccc1)C(=O)CCc1cn(C(=O)OC(C)(C)C)c2ccccc12]

To solution containing 3-(1H-indol-3-yl)propanoic acid (200 mg, 1.06 mmol), N'-isopropylbenzohydrazide (283.4 mg, 1.59 mmol) and HATU (604.6 mg, 1.59 mmol) dissolved in DMF (7.0 ml), N,N-diisopropylethylamine (DIPEA) (0.277 ml, 1.59 mmol) was slowly drop-wise added and stirred at room temperature for 12 hr. The reaction mixture was diluted with EtOAc, washed with water and brine, dried with anhydrous MgSO₄, filtered, and concentrated under reduced pressure. The residue was separated through silica gel chromatography (n-hexane:EtOAc:methanol=20:3:1) and dried so that white solid form of N'-(3-(1H-indol-3-yl)propanoyl)-N'-isopropylbenzohydrazide was obtained. After adding K₂CO₃ to N'-(3-(1H-indol-3-yl)propanoyl)-N'-isopropylbenzohydrazide, nitrogen substitution, and dissolving in THF/H₂O, (Boc)₂O was slowly drop-wise added and refluxed for 12 hr. After the reaction mixture was concentrated under reduced pressure, the residue was separated through silica gel chromatography (n-hexane:EtOAc:methanol=15:3:1) and dried so that white solid form of tert-butyl 3-(3-(2-benzoyl-1-isopropylhydrazinyl)-3-oxopropyl)-1H-indole-1-carboxylate was obtained. (285.9 mg, 60%)

¹H-NMR (CDCl₃, 500 MHz): δ 8.08 (brs, 1H, —NH), 7.72 (m, 3H, Ar—H), 7.56 (m, 2H, Ar—H), 7.45 (m, 5H, Ar—H), 4.92 (q, J=6.35 Hz, 1H, —NCH(CH₃)₂), 3.02 (dd, 2H, —CH₂—CH₂—), 2.69 (dd, 2H, —CH₂—CH₂—), 1.67 (s. 9H, Boc), 1.14 (m, 6H, —NCH(CH₃)₂

Example 25

Preparation of (E)-N'-isopropyl-N'-(3-(1-methyl-1H-indol-3-yl)acryloyl)benzohydrazide)

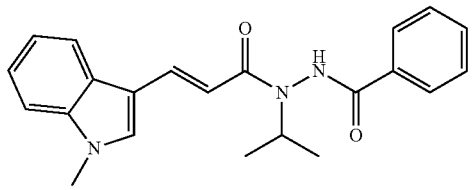 [SMILES: CC(C)N(NC(=O)c1ccccc1)C(=O)/C=C/c1cn(C)c2ccccc12]

To solution containing (E)-3-(1-methyl-1H-indol-3-yl)acrylic acid (50 mg, 0.24 mmol, 1.0 equivalent), N'-isopropylbenzohydrazide (66.43 mg, 0.37 mmol, 1.5 equivalent) and HATU (141.72 mg, 0.37 mmol, 1.5 equivalent) dissolved in DMF (5.0 ml), N,N-diisopropylethylamine (DIPEA)(0.06 ml, 0.37 mmol, 1.5 equivalent) was slowly drop-wise added and stirred at room temperature for 24 hr. The reaction mixture was diluted with EtOAc, washed with water and brine, dried with anhydrous $MgSO_4$, filtered, and concentrated under reduced pressure. The residue was separated through silica gel chromatography (n-hexane:EtOAc:methanol=9:3:1) and dried so that white solid form of (E)-N'-isopropyl-N'-(3-(1-methyl-1H-indol-3-yl)acryloyl)benzohydrazide was obtained.(82.62 mg, 92%).

$^1$H-NMR (CDCl$_3$, 500 MHz): δ 10.72 (1H, brs, NH), 7.98 (2H, dd, J=7.82 Hz, Ar—H, CH=CH), 7.77 (1H, s, Ar—H), 7.68 (2H, m, Ar—H), 7.59 (2H, t, J=7.82 Hz, Ar—H), 7.46 (2H, t, J=7.82 Hz, Ar—H), 7.19 (1H, t, J=7.33 Hz, Ar—H), 6.92 (1H, t, J=7.33 Hz, Ar—H), 6.70 (1H, d, J=15.65 Hz, CH=CH), 4.81 (1H,q, —N—CH—(CH$_3$)$_2$), 3.77 (3H, s, indole-CH$_3$), 1.18(3H, d, J=6.84 Hz, —N—CH—(CH$_3$)$_2$), 1.10(3H, d, J=6.35 Hz, —N—CH—(CH$_3$)$_2$)

Example 26

Preparation of (E)-N'-(3-(1-benzyl-1H-indol-3-yl)acryloyl)-N'-isopropylbenzohydrazide

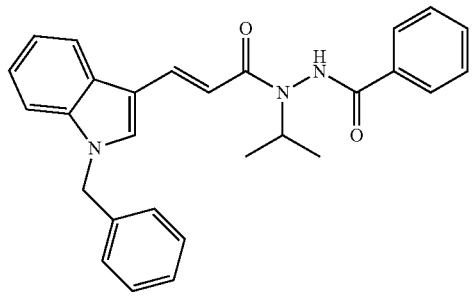 [SMILES: CC(C)N(NC(=O)c1ccccc1)C(=O)/C=C/c1cn(Cc2ccccc2)c2ccccc12]

To solution containing (E)-3-(1-benzyl-1H-indol-3-yl)acrylic acid (30 mg, 0.14 mmol, 1.0 equivalent), N'-isopropylbenzohydrazide (28.92 mg, 0.16 mmol, 1.5 equivalent) and HATU (61.6 mg, 0.16 mmol, 1.5 equivalent) dissolved in DMF (3.0 ml), N,N-diisopropylethylamine (DIPEA)(0.03 ml, 0.16 mmol, 1.5 equivalent) was slowly drop-wise added and stirred at room temperature for 24 hr. The reaction mixture was diluted with EtOAc, washed with water and brine, dried with anhydrous $MgSO_4$, filtered, and concentrated under reduced pressure. The residue was separated through silica gel chromatography (n-hexane:EtOAc=1:1) and dried so that white solid form of (E)-N'-(3-(1-benzyl-1H-indol-3-yl)acryloyl)-N'-isopropylbenzohydrazide was obtained (40.6 mg, 86%).

$^1$H-NMR (CDCl$_3$, 500 MHz): δ 10.73 (1H, brs, NH), 7.97 (3H, d, J=6.84 Hz, Ar—H), 7.73 (1H, d, J=715.65 Hz, CH=CH), 7.66 (1H, t, J=7.33 Hz, Ar—H), 7.59 (1H, t, J=7.33 Hz, Ar—H), 7.49 (2H, m, Ar—H), 7.29 (2H, t, J=7.33 Hz, Ar—H), 7.24 (1H, d, J=7.33 Hz, Ar—H), 7.20 (2H, d, J=7.33 Hz, Ar—H), 7.13 (1H, t, J=7.82 Hz, Ar—H), 6.90 (1H, t, J=7.33 Hz, Ar—H), 6.73 (1H, d, J=15.65 Hz, CH=CH), 5.42 (2H, s, N—CH$_2$—Ar—H), 4.81 (1H, q, —N—CH—(CH$_3$)$_2$), 1.18 (3H, d, J=6.84 Hz, —N—CH—(CH$_3$)$_2$), 1.12 (3H, d, J=6.84 Hz, —N—CH—(CH$_3$)$_2$)

Example 27

Preparation of (E)-N'-isopropyl-N'-(3-(1-(3-methylbut-2-enyl)-1H-indol-3-yl)acryloyl)benzohydrazide

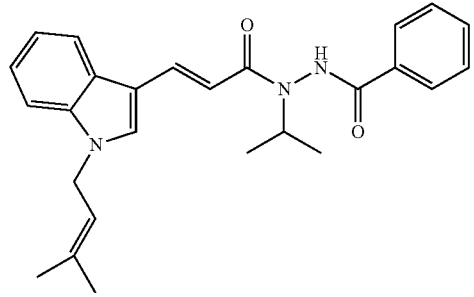 [SMILES: CC(C)=CCn1cc(/C=C/C(=O)N(NC(=O)c2ccccc2)C(C)C)c2ccccc21]

To solution containing (E)-3-(1-(3-methylbut-2-enyl)-1H-indol-3-yl)acrylic acid (160 mg, 0.62 mmol, 1.0 equivalent), N'-isopropylbenzohydrazide (167.5 mg, 0.94 mmol, 1.5 equivalent) and HATU (357.4 mg, 0.94 mmol, 1.5 equivalent) dissolved in DMF (5.0 ml), N,N-diisopropylethylamine (DIPEA)(0.16 ml, 0.94 mmol, 1.5 equivalent) was slowly drop-wise added and stirred at room temperature for 24 hr. The reaction mixture was diluted with EtOAc, washed with water and brine, dried with anhydrous $MgSO_4$, filtered, and concentrated under reduced pressure. The residue was separated through silica gel chromatography (n-hexane:EtOAc=1:1) and dried so that yellow solid form of (E)-N'-isopropyl-N'-(3-(1-(3-methylbut-2-enyl)-1H-indol-3-yl)acryloyl)benzohydrazide was obtained. (99.8 mg, 39%).

$^1$H-NMR (DMSO, 500 MHz): δ 10.72 (1H, brs, NH), 7.96 (2H, d, J=7.33 Hz, Ar—H), 7.78 (1H, s, Ar—H), 7.71 (1H, d, J=16.38 Hz, CH=CH), 7.66 (1H, d, J=7.33 Hz, Ar—H), 7.59 (2H, t, J=6.11 Hz, Ar—H), 7.45 (2H, t, J=9.41 Hz, Ar—H), 7.16 (1H, t, J=7.45 Hz, Ar—H), 6.91 (1H, t, J=9.04 Hz, Ar—H), 6.70 (1H, d, J=15.77 Hz, CH=CH), 5.30 (1H, t, J=7.33 Hz, CH$_2$—CH=(CH$_3$)$_2$), 4.80 (1H, t, J=7.58 Hz, N—CH—(CH$_3$)$_2$), 4.76 (2H, d, J=6.23 Hz, CH$_2$—CH—(CH$_3$)$_2$), 1.79 (3H, s, CH$_2$—CH=(CH$_3$)$_2$), 1.68 (3H, s, CH$_2$—CH=(CH$_3$)$_2$), 1.16 (3H, d, d, J=6.84 Hz, —N—CH—(CH$_3$)$_2$), 1.12 (3H, d, J=6.84 Hz, —N—CH—(CH$_3$)$_2$)

Example 28

Preparation of (E)-N'-(3-(1-(cyclopropylmethyl)-1H-indol-3-yl)acryloyl)-N'-isopropylbenzohydrazide

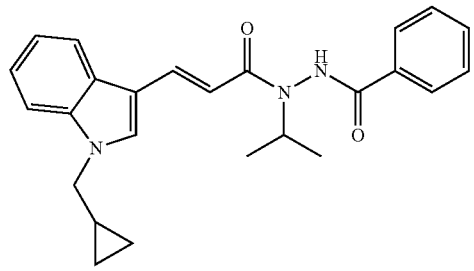 [SMILES: CC(C)N(NC(=O)c1ccccc1)C(=O)/C=C/c1cn(CC2CC2)c2ccccc12]

To solution containing (E)-3-(1-(cyclopropylmethyl)-1H-indol-3-yl)acrylic acid (165 mg, 0.68 mmol, 1.0 equivalent), N'-isopropylbenzohydrazide (182.8 mg, 1.02 mmol, 1.5 equivalent) and HATU (390 mg, 1.02 mmol, 1.5 equivalent) dissolved in DMF (5.0 ml), N,N-diisopropylethylamine (DIPEA)(0.18 ml, 1.02 mmol, 1.5 equivalent) was slowly drop-wise added and stirred at room temperature for 24 hr. The reaction mixture was diluted with EtOAc, washed with water and brine, dried with anhydrous MgSO$_4$, filtered, and concentrated under reduced pressure. The residue was separated through silica gel chromatography (n-hexane:EtOAc=1:1) and dried so that yellow solid form of (E)-N'-(3-(1-(cyclopropylmethyl)-1H-indol-3-yl)acryloyl)-N'-isopropylbenzohydrazide was obtained. (202 mg, 74%).

$^1$H-NMR (DMSO, 500 MHz): δ 10.73 (1H, brs, NH), 7.98 (2H, d, J=7.33 Hz, Ar—H), 7.88 (1H, s, Ar—H), 7.73 (1H, d, J=15.65 Hz, C$\underline{H}$=CH), 7.66 (1H, d, J=7.33 Hz, Ar—H), 7.59 (3H, m, Ar—H), 7.47 (1H, d, J=7.82 Hz, Ar—H), 7.17 (1H, t, J=7.82 Hz, Ar—H), 6.91 (1H, t, J=7.33 Hz, Ar—H), 6.71 (1H, d, J=15.65 Hz, CH=C$\underline{H}$), 4.80 (1H, t, J=6.84 Hz, N—C$\underline{H}$—(CH$_3$)$_2$), 4.02 dd, J=6.84 Hz, C$\underline{H}_2$-cyclopropane), 1.23 (1H, m, cyclopropane), 1.18 (3H, d, J=9.29 Hz, —N—CH—(C$\underline{H}_3$)$_2$), 1.12 (3H, d, J=6.35 Hz, —N—CH—(C$\underline{H}_3$)$_2$), 0.50 (2H, dd, J=6.84 Hz, cyclopropane), 0.37 (2H, dd, J=4.89 Hz, cyclopropane)

Example 29

Preparation of (E)-N'-(3-(1-cyclopropyl-1H-indol-3-yl)acryloyl)-N'-isopropylbenzohydrazide

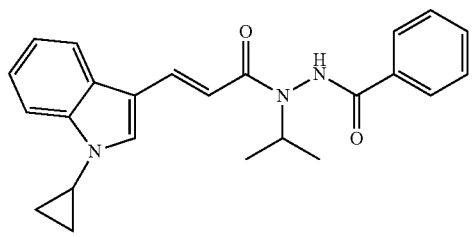 [SMILES: CC(C)N(NC(=O)c1ccccc1)C(=O)/C=C/c1cn(C2CC2)c2ccccc12]

To solution containing (E)-3-(1-cyclopropyl-1H-indol-3-yl)acrylic acid (160 mg, 0.70 mmol, 1.0 equivalent), N'-isopropylbenzohydrazide (188.8 mg, 1.05 mmol, 1.5 equivalent) and HATU (401.5 mg, 1.05 mmol, 1.5 equivalent) dissolved in DMF (5.0 ml), N,N-diisopropylethylamine (DIPEA)(0.18 ml, 1.05 mmol, 1.5 equivalent) was slowly drop-wise added and stirred at room temperature for 24 hr. The reaction mixture was diluted with EtOAc, washed with water and brine, dried with anhydrous MgSO$_4$, filtered, and concentrated under reduced pressure. The residue was separated through silica gel chromatography (n-hexane:EtOAc=1:1) and dried so that solid form of (E)-N'-(3-(1-cyclopropyl-1H-indol-3-yl)acryloyl)-N'-isopropylbenzohydrazide was obtained. (87.9 mg, 32%).

$^1$H-NMR (DMSO, 500 MHz): δ 10.72 (1H, brs, NH), 7.97 (2H, d, J=7.82 Hz, Ar—H), 7.79 (1H, s, Ar—H), 7.69 (1H, d, J=16.13 Hz, C$\underline{H}$=CH), 7.65 (1H, s, Ar—H), 7.59 (3H, t, J=7.82 Hz, Ar—H), 7.44 (1H, d, J=7.82 Hz, Ar—H), 7.20 (1H, t, J=7.33 Hz, Ar—H), 6.93 (1H, t, J=7.33 Hz, Ar—H), 6.72 (1H, d, J=15.16 Hz, CH=C$\underline{H}$), 4.80 (1H, t, J=6.84 Hz, N—C$\underline{H}$—(CH$_3$)$_2$), 3.46 (1H, m, N-cyclopropyl), 1.18 (3H, d, J=6.35 Hz, —N—CH—(C$\underline{H}_3$)$_2$), 1.11 (3H, d, J=6.35 Hz, —N—CH—(C$\underline{H}_3$)$_2$), 1.06 (2H, dd, J=6.35 Hz, cyclopropane), 0.93 (2H, dd, J=6.35 Hz, cyclopropane)

Example 30

Preparation of (E)-N'-(3-(1-acetyl-1H-indol-3-yl)acryloyl)-N'-isopropylbenzohydrazide

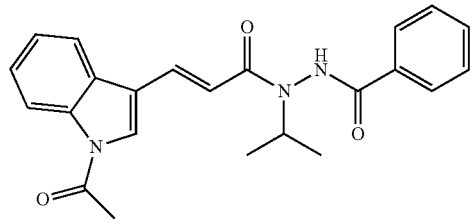 [SMILES: CC(=O)n1cc(/C=C/C(=O)N(NC(=O)c2ccccc2)C(C)C)c2ccccc21]

To a round bottom flask, (E)-N'-(3-(1H-indol-3-yl)acryloyl)-N'-isopropylbenzohydrazide (27 mg, 0.07 mmol, 1.0 equivalent), K$_2$CO$_3$ (32.2 mg, 0.23 mmol, 3.0 equivalent), DMAP (cat, 0.12 equivalent) were introduced and dissolved in DMF, after which acetic anhydride (0.015 ml, 0.15 mmol, 2.0 equivalent) was introduced. After stirring at room temperature for 24 hr, the reaction mixture was diluted with EtOAc, washed with water and brine, dried with anhydrous MgSO$_4$, filtered, and concentrated under reduced pressure. The residue was separated through silica gel chromatography (n-hexane:EtOAc:methanol=7:3:1) and dried so that solid form of (E)-N-(3-(1-acetyl-1H-indol-3-yl)acryloyl)-N'-isopropylbenzohydrazide was obtained. (2.6 mg, 8.9%).

$^1$H-NMR (CDCl$_3$, 500 MHz): δ 8.42 (1H, d, J=8.31 Hz, Ar—H), 7.91 (3H, m, Ar—H), 7.86 (1H, d, J=15.65 Hz, C$\underline{H}$=CH), 7.65 (1H, t, J=7.82 Hz, Ar—H), 7.58 (4H, m, Ar—H), 7.34 (1H, t, J=7.82 Hz, Ar—H), 7.15 (1H, brs, —NH), 6.96 (1H, d, J=15.65 Hz, CH=C$\underline{H}$), 5.04 (1H, m, N—C$\underline{H}$—(CH$_3$)$_2$), 2.63 (3H, s, -Acetyl), 1.31 (3H, d, J=6.84 Hz, —N—CH—(C$\underline{H}_3$)$_2$), 1.28 (3H, d, J=6.35 Hz, —N—CH—(C$\underline{H}_3$)$_2$)

Example 31

Preparation of (E)-N'-isopropyl-N'-(3-(1-pivaloyl-1H-indol-3-yl)acryloyl)benzohydrazide

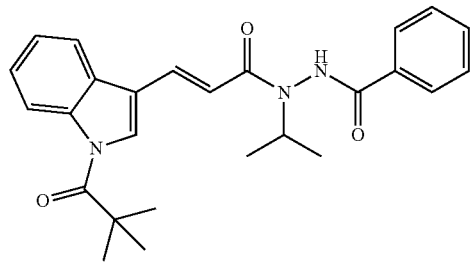 [SMILES: CC(C)N(NC(=O)c1ccccc1)C(=O)/C=C/c1cn(C(=O)C(C)(C)C)c2ccccc12]

To a round bottom flask, (E)-N'-(3-(1H-indol-3-yl)acryloyl)-N'-isopropylbenzohydrazide (60 mg, 0.17 mmol, 1.0 equivalent), K$_2$CO$_3$ (71.6 mg, 0.51 mmol, 3.0 equivalent), and DMAP (cat, 0.12 equivalent) were introduced and dissolved in DMF, after which Piv-Cl (0.04 ml, 0.34 mmol, 2.0 equivalent) was introduced. After stirring at room temperature for 24 hr, the reaction mixture was diluted with EtOAc, washed with water and brine, dried with anhydrous MgSO$_4$, filtered, and concentrated under reduced pressure. The residue was separated through silica gel chromatography (n-hexane:EtOAc:methanol=7:3:1) and dried so that solid form of (E)-N'-(3-(1-acetyl-1H-indol-3-yl)acryloyl)-N'-isopropylbenzohydrazide was obtained. (10.3 mg, 14%).

¹H-NMR (DMSO, 500 MHz): δ 10.82 (1H, brs, —NH), 8.63 (1H, s, Ar—H), 8.39 (1H, d, J=7.82 Hz, Ar—H), 7.98 (2H, d, J=6.97 Hz, Ar—H), 7.82 (1H, d, J=15.65 Hz, CH═CH), 7.62-7.69 (3H, m, Ar—H), 7.57 (1H, d, J=7.82 Hz, Ar—H), 7.37 (1H, t, J=7.82 Hz, Ar—H), 7.02 (1H, t, J=7.97 Hz, Ar—H), 6.98 (1H, d, J=15.65 Hz, CH═CH), 4.82 (1H, m, N—CH—(CH₃)₂), 1.47 (9H, s, -Piv), 1.25 (3H, d, J=6.84 Hz, —N—CH—(CH₃)₂), 1.15 (3H, d, J=6.35 Hz, —N—CH—(CH₃)₂)

Example 32

Preparation of (E)-N'-(3-(1-benzoyl-1H-indol-3-yl)acryloyl)-N'-isopropylbenzohydrazide

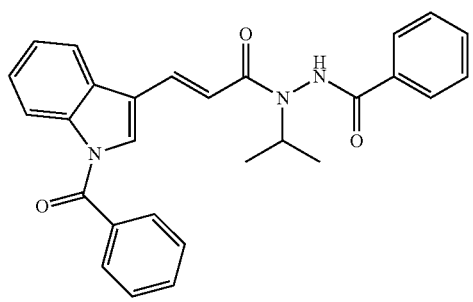 [SMILES: CC(C)N(NC(=O)c1ccccc1)C(=O)/C=C/c1cn(C(=O)c2ccccc2)c2ccccc12]

To a round bottom flask, (E)-N'-(3-(1H-indol-3-yl)acryloyl)-N'-isopropylbenzohydrazide (50 mg, 0.14 mmol, 1.0 equivalent), and DMAP (cat, 4.0 mg, 0.14 equivalent) were introduced and dissolved in CH₂Cl₂, after which DIPEA (0.04 ml, 0.20 mmol, 1.5 equivalent) was introduced. After introducing benzoyl chloride (0.02 ml, 0.17 mmol, 1.2 equivalent) at 0° C. and stirring at room temperature for 24 hr, the reaction mixture was diluted with EtOAc, washed with water and brine, dried with anhydrous MgSO₄, filtered, and concentrated under reduced pressure. The residue was separated through silica gel chromatography (n-hexane:EtOAc:=1:1) and dried so that solid form of (E)-N'-(3-(1-benzoyl-1H-indol-3-yl)acryloyl)-N'-isopropylbenzohydrazide was obtained. (48.0 mg, 77%).

¹H-NMR (DMSO, 500 MHz): δ 10.75 (1H, brs, —NH), 8.25 (1H, d, J=8.31 Hz, Ar—H), 7.92 (2H, m, Ar—H, CH═CH), 7.86 (1H, s, Ar—H), 7.75 (2H, d, J=8.31 Hz, Ar—H), 7.69-7.74 (2H, m, Ar—H), 7.58 (5H, d, J=7.82 Hz, Ar—H), 7.47 (1H, t, J=7.82 Hz, Ar—H), 7.37 (1H, t, J=7.82 Hz, Ar—H), 7.14 (1H, t, J=7.82 Hz, Ar—H), 6.88 (1H, d, J=15.65 Hz, CH═CH), 4.77 (1H, m, N—CH—(CH₃)₂), 1.17 (3H, d, J=6.84 Hz, —N—CH—(CH₃)₂), 1.10 (3H, d, J=6.35 Hz, —N—CH—(CH₃)₂)

Example 33

Preparation of (E)-N'-(3-(1-(3,3-dimethylbutanoyl)-1H-indol-3-yl)acryloyl)-N'-isopropylbenzohydrazide

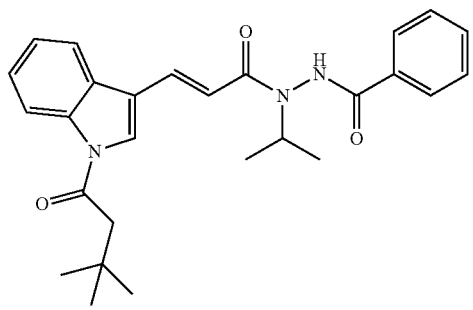 [SMILES: CC(C)N(NC(=O)c1ccccc1)C(=O)/C=C/c1cn(C(=O)CC(C)(C)C)c2ccccc12]

To a round bottom flask, (E)-N'-(3-(1H-indol-3-yl)acryloyl)-N'-isopropylbenzohydrazide (50 mg, 0.14 mmol, 1.0 equivalent), and DMAP (cat, 4.0 mg, 0.14 equivalent) were introduced and dissolved in CH₂Cl₂, after which DIPEA (0.04 ml, 0.20 mmol, 1.5 equivalent) was introduced. After introducing at 0° C. 3-3-dimethylbutyryl chloride (0.02 ml, 0.17 mmol, 1.2 equivalent) and stirring at room temperature for 24 hr, the reaction mixture was diluted with EtOAc, washed with water and brine, dried with anhydrous MgSO₄, filtered, and concentrated under reduced pressure. The residue was separated through silica gel chromatography (n-hexane:EtOAc:=2:1) and dried so that soli form of (E)-N'-(3-(1-(3,3-dimethylbutanoyl)-1H-indol-3-yl)acryloyl)-N'-isopropylbenzohydrazide was obtained. (39.7 mg, 62%).

¹H-NMR (DMSO, 500 MHz): δ 11.20 (1H, brs, —NH), 8.63 (1H, s, Ar—H), 8.39 (1H, d, J=7.82 Hz, Ar—H), 7.98 (2H, d, J=6.97 Hz, Ar—H), 7.82 (1H, d, J=15.65 Hz, CH═CH), 7.62-7.69 (3H, m, Ar—H), 7.57 (1H, d, J=7.82 Hz, Ar—H), 7.37 (1H, t, J=7.82 Hz, Ar—H), 7.02 (1H, t, J=7.97 Hz, Ar—H), 6.98 (1H, d, J=15.65 Hz, CH═CH), 4.82 (1H, m, N—CH-(CH₃)₂), 2.32 (2H, s, —CH₂—CH₃) 1.47 (9H, s, —CH₂—CH₃), 1.25 (3H, d, J=6.84 Hz, —N—CH—(CH₃)₂), 1.15 (3H, d, J=6.35 Hz, —N—CH—(CH₃)₂)

Example 34

Preparation of (E)-3-fluoro-N'-isopropyl-N'-(3-(1-(3-methylbut-2-enyl)-1H-indol-3-yl)acryloyl)benzohydrazide)

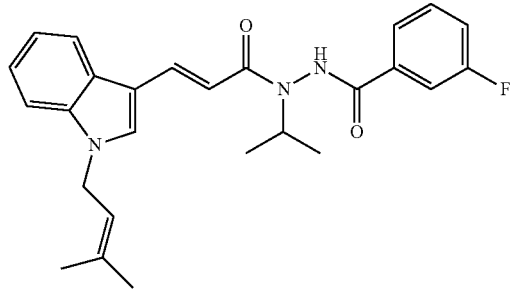 [SMILES: CC(C)=CCn1cc(/C=C/C(=O)N(NC(=O)c2cccc(F)c2)C(C)C)c2ccccc21]

To solution containing (3-(1-(3-methylbut-2-enyl)-1H-indol-3-yl)acrylic acid (200.0 mg, 0.78 mmol), 3-fluoro-N'-isopropylbenzohydrazide (229.6 mg, 1.17 mmol) and HATU (444.9 mg, 1.17 mmol) dissolved in DMF (5.0 ml), N,N-diisopropylethylamine (DIPEA)(0.2 ml, 1.17 mmol) was slowly drop-wise added and stirred at room temperature for 12 hr. The reaction mixture was diluted with EtOAc, washed with water and brine, dried with anhydrous MgSO₄, filtered, and concentrated under reduced pressure. The residue was separated through silica gel chromatography (50% EtOAc) and dried so that yellow (E)-3-fluoro-N'-isopropyl-N'-(3-(1-(3-methylbut-2-enyl)-1H-indol-3-yl)acroyl)benzohydrazide was obtained (286 mg, 88.2%).

¹H-NMR (CDCL₃, 500 MHz): δ 9.19 (1H, brs, —NH), 7.83 (1H, d, J=15.4 Hz, aromatic), 7.73 (1H, d, J=7.8 Hz, indole-CH═CH—), 7.67 (1H, d, J=8.3 Hz, aromatic), 7.56 (1H, s, aromatic), 7.39 (1H, d, J=5.6 Hz, aromatic), 7.21 (4H, m, aromatic), 6.97 (1H, s, aromatic), 6.75 (1H, d, J=15.4 Hz, indole-CH═CH—), 5.22 (1H, s, —N—CH₂—CH═(CH₃)₂), 4.90 (1H, brs, —N—CH—(CH₃)₂), 4.49 (2H, d, J=5.6 Hz, —N—CH₂—CH═(CH₃)₂), 1.73 (6H, d, J=13.2 Hz, —N—CH₂—CH═(CH₃)₂), 1.19 (6H, d, J=5.9 Hz, —N—CH—(CH₃)₂)

Example 35

Preparation of (E)-tert-butyl 3-(3-(2-(3-fluorobenzoyl)-1-isopropylhydrazinyl)-3-oxoprop-1-enyl)-5-methyl-1H-indole-1-carboxylate

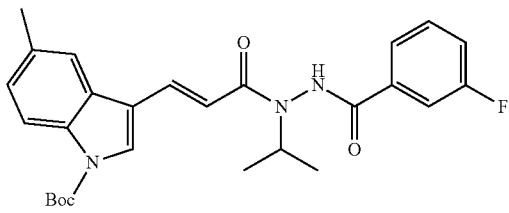 [SMILES: Cc1ccc2c(c1)c(/C=C/C(=O)N(NC(=O)c1cccc(F)c1)C(C)C)cn2C(=O)OC(C)(C)C]

Step 1: Preparation of (E)-ethyl-3-(5-methyl-1H-indol-3-yl)acrylate 5-methyl-1H-indole-3-carbaldehyde (900 mg, 5.65 mmol) was dissolved in benzene (100 ml), and ethyl(Triphenylphosphoranylidene)acetate (2954.1 mg, 8.48 ml) was drop-wise added. The temperature of mixture was raised to 80° C. and stirred under reflux for 12 hr. After completion of the reaction, the reaction mixture was cooled to room temperature, concentrated under reduced pressure, and refined through silica gel chromatography (n-hexane:EtOAc=4:1) to give target compound (1230 mg, 95%).

Step 2: Preparation of (E)-3-(5-methyl-1H-indol-3-yl)acrylic acid (E)-ethyl-3-(5-methyl-1H-indol-3-yl)acrylate (1222.4 g, 5.33 mmol) prepared at Step 1 was dissolved in 32 ml of mixture solution (THF/methanol/H2O=2:1:1), after which NaOH acqueous solution (639.8 mg, 16.0 mmol) was added. After raising temperature to 50° C., stirring for 12 hr, neutralization with 10% hydrochoric acid to pH 4, and dilution with EtOAc, washing with water and brine, drying with anhydrous MgSO4, and concentration under reduced pressure followed. The concentrated residue was refined with silica gel chromatography (n-hexane:EtOAc=2:1) and dried to give target compound. (1070.5 mg, 99.8%).

Step 3: Preparation of (E)-3-(1-(tert-butoxycarbonyl)-5-methyl-1H-indol-3-yl)acrylic acid (E)-3-(5-methyl-1H-indol-3-yl)acrylic acid (547 mg, 2.72 mmol) prepared at Step 2 was dissolved in 2 ml of mixture solution of CH3CN (20 ml) and THF/H2O=1:1. After adding DMAP (66.4 mg, 0.54 mmol), TEA (0.76 ml, 5.44 mmol) and di-tert-butyl dicarbonate (1186.6 mg, 5.44 mmol) in order, and stirring for 6 hr, the reaction mixture was recrystallized with 6N hydrochloric acid to give target compound (795 mg, 97%).

Step 4: Preparation of (E)-tert-butyl 3-(3-(2-(3-fluorobenzoyl)-1-isopropylhydrazinyl)-3-oxoprop-1-enyl)-5-methyl-1H-indole-1-carboxylate 3-(1-(tert-butoxycarbonyl)-5-methyl-1H-indol-3-yl)acrylic acid (100.0 mg, 0.33 mmol) of Step 3,3-fluoro-N'-isopropylbenzohydrazide (97.7 mg, 0.50 mmol) and HATU (189.3 mg, 0.50 mmol) dissolved in DMF (3.0 ml), and N,N-diisopropylethylamine (DIPEA)(0.08 ml, 0.50 mmol) were slowly drop-wise added and stirred at room temperature for 12 hr. The reaction mixture was diluted with EtOAc, washed with water and brine, dried with anhydrous MgSO4, filtered, and concentrated under reduced pressure. The residue was separated through silica gel chromatography (33% EtOAc) and dried so that white (E)-tert-butyl 3-(3-(2-(3-fluorobenzoyl)-1-isopropylhydrazinyl)-3-oxoprop-1-enyl)-5-methyl-1H-indole-1-carboxylate was obtained (71.8 mg, 45.4%).

$^1$H-NMR (DMSO, 500 MHz): δ 10.91 (1H, brs, —N$\underline{H}$), 8.07 (1H, s, aromatic), 7.94 (1H, d, J=8.6 Hz, aromatic), 7.85 (1H, d, J=7.6 Hz, aromatic), 7.81 (1H, d, J=9.5 Hz, aromatic), 7.70 (1H, d, J=15.9 Hz, indole-C$\underline{H}$=CH—), 7.64 (1H, m, aromatic), 7.51 (1H, m, aromatic), 7.25 (1H, s, aromatic), 7.13 (1H, d, J=8.3 Hz, aromatic), 6.86 (1H, d, J=15.9 Hz, indole-CH=C$\underline{H}$—), 4.80 (1H, m, —N—C$\underline{H}$—(CH3)2), 2.06 (3H, s, Indole-C$\underline{H}_3$), 1.58 (9H, s, Boc), 1.15 (6H, m, —N—CH—(C$\underline{H}_3$)2)

Example 36

Preparation of (E)-tert-butyl 3-(3-(2-(3-fluorobenzoyl)-1-isopropylhydrazinyl)-3-oxoprop-1-enyl)-6-isopropyl-1H-indole-1-carboxylate

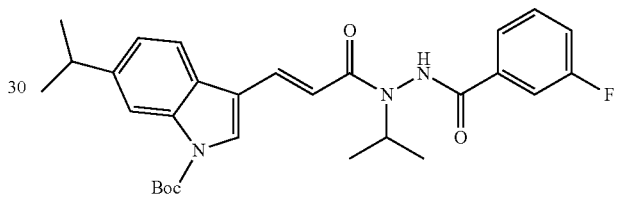

Step 1~3: Preparation of (E)-3-(1-(tert-butoxycarbonyl)-6-isopropyl-1H-indol-3-yl)acrylic acid The target compound was obtained in the same manner as that of Steps 1 to 3 of Example 35, except for the difference of using 6-isopropyl-1H-indole-3-carbaldehyde instead of 5-methyl-1H-indole-3-carbaldehyde of Step 1 of Example 35.

Step 4: Preparation of (E)-tert-butyl 3-(3-(2-(3-fluorobenzoyl)-1-isopropylhydrazinyl)-3-oxoprop-1-enyl)-6-isopropyl-1H-indole-1-carboxylate To solution containing 3-(1-(tert-butoxycarbonyl)-6-isopropyl-1H-indol-3-yl)acrylic acid (183.0 mg, 0.56 mmol), 3-fluoro-N'-isopropylbenzohydrazide (163.5 mg, 0.83 mmol) and HATU (316.9 mg, 0.83 mmol) dissolved in DMF (3.0 ml), N,N-diisopropylethylamine (DIPEA)(0.14 ml, 0.83 mmol) was slowly drop-wise added and stirred at room temperature for 12 hr. The reaction mixture was diluted with EtOAc, washed with water and brine, dried with anhydrous MgSO4, filtered, and concentrated under reduced pressure. The residue was separated through silica gel chromatography (33% EtOAc) for refinement, and dried so that white (E)-tert-butyl 3-(3-(2-(3-fluorobenzoyl)-1-isopropylhydrazinyl)-3-oxoprop-1-enyl)-5-methyl-1H-indole-1-carboxylate was obtained (138.0 mg, 48.6%).

$^1$H-NMR (DMSO, 500 MHz): δ 10.86 (1H, brs, —NH), 8.05 (1H, s, aromatic), 7.98 (1H, s, aromatic), 7.82 (1H, d, J=7.8 Hz, aromatic), 7.76 (1H, d, J=9.5 Hz, indole-C$\underline{H}$=CH—), 7.68 (2H, m, aromatic), 7.53 (1H, m, aromatic), 7.43 (1H, d, J=8.3 Hz, aromatic), 6.98 (1H, d, J=8.1 Hz, aromatic), 6.83 (1H, d, J=15.9 Hz, indole-CH=CH—), 4.80 (1H, m, —N—CH—(CH₃)₂), 2.96 (1H, m, -indole-CH—(CH₃)₂), 1.60 (9H, s, Boc), 1.16 (12H, m, -indole-CH—(CH₃)₂, —N—CH—(CH₃)₂)

Example 37

Preparation of (E)-tert-butyl 3-(3-(2-(3-fluorobenzoyl)-1-isopropylhydrazinyl)-3-oxoprop-1-enyl)-6-methyl-1H-indole-1-carboxylate

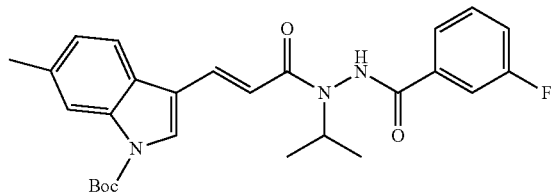 [SMILES: Cc1ccc2c(/C=C/C(=O)N(NC(=O)c3cccc(F)c3)C(C)C)cn(C(=O)OC(C)(C)C)c2c1]

Step 1~3: Preparation of (E)-3-(1-(tert-butoxycarbonyl)-6-methyl-1H-indol-3-yl)acrylic acid The target compound was obtained in the same manner as that of Steps 1 to 3 of Example 35, except for the difference of using 6-methyl-1H-indole-3-carbaldehyde instead of 5-methyl-1H-indole-3-carbaldehyde of Step 1 of Example 35.

Step 4: Preparation of (E)-tert-butyl 3-(3-(2-(3-fluorobenzoyl)-1-isopropylhydrazinyl)-3-oxoprop-1-enyl)-6-methyl-1H-indole-1-carboxylate To solution containing 3-(1-(tert-butoxycarbonyl)-6-methyl-1H-indol-3-yl)acrylic acid (200.0 mg, 0.66 mmol), 3-fluoro-N'-isopropylbenzohydrazide (195.4 mg, 1.00 mmol) and HATU (378.6 mg, 1.00 mmol) dissolved in DMF (5.0 ml), N,N-diisopropylethylamine (DIPEA)(0.16 ml, 1.00 mmol) was slowly drop-wise added and stirred at room temperature for 12 hr. The reaction mixture was diluted with EtOAc, washed with water and brine, dried with anhydrous MgSO₄, filtered, and concentrated under reduced pressure. The residue was separated through silica gel chromatography (50% EtOAc) for refinment and dried so that white (E)-tert-butyl 3-(3-(2-(3-fluorobenzoyl)-1-isopropylhydrazinyl)-3-oxoprop-1-enyl)-6-methyl-1H-indole-1-carboxylate was obtained (161.0 mg, 50.9%).

¹H-NMR (DMSO, 500 MHz): δ 10.87 (1H, brs, —NH), 8.03 (1H, s, aromatic), 7.92 (1H, s, aromatic), 7.82 (1H, d, J=7.8 Hz, aromatic), 7.76 (2H, d, J=9.3 Hz, aromatic, indole-CH=CH—), 7.67 (1H, m, aromatic), 7.52 (1H, m, aromatic), 7.39 (1H, d, J=8.1 Hz, aromatic), 6.90 (1H, d, J=8.1 Hz, aromatic), 6.82 (1H, d, J=15.9 Hz, indole-CH=CH—), 4.80 (1H, m, —N—CH—(CH₃)₂), 2.38 (3H, s, Indole-CH₃), 1.59 (9H, s, Boc), 1.15 (6H, m, —N—CH—(CH₃)₂)

Example 38

Preparation of (E)-tert-butyl 6-fluoro-3-(3-(2-(3-fluorobenzoyl)-1-isopropylhydrazinyl)-3-oxoprop-1-enyl)-1H-indole-1-carboxylate

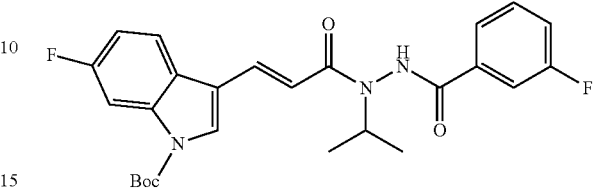

Step 1~3: Preparation of (E)-3-(1-(tert-butoxycarbonyl)-6-fluoro-1H-indol-3-yl)acrylic acid The target compound was obtained in the same manner as that of Steps 1 to 3 of Example 35, except for the difference of using 6-fluoro-1H-indole-3-carbaldehyde instead of 5-methyl-1H-indole-3-carbaldehyde of Step 1 of Example 35.

Step 4: Preparation of (E)-tert-butyl 6-fluoro-3-(3-(2-(3-fluorobenzoyl)-1-isopropylhydrazinyl)-3-oxoprop-1-enyl)-1H-indole-1-carboxylate To solution containing 3-(1-(tert-butoxycarbonyl)-6-fluoro-1H-indol-3-yl)acrylic acid (200.0 mg, 0.66 mmol), 3-fluoro-N'-isopropylbenzohydrazide (192.8 mg, 0.98 mmol) and HATU (376.6 mg, 0.98 mmol) dissolved in DMF (5.0 ml), N,N-diisopropylethylamine (DIPEA)(0.16 ml, 0.98 mmol) was slowly drop-wise added and stirred at room temperature for 12 hr. The reaction mixture was diluted with EtOAc, washed with water and brine, dried with anhydrous MgSO₄, filtered, and concentrated under reduced pressure. The residue was separated through silica gel chromatography (50% EtOAc) for refinment and dried so that white (E)-tert-butyl 6-fluoro-3-(3-(2-(3-fluorobenzoyl)-1-isopropylhydrazinyl)-3-oxoprop-1-enyl)-1H-indole-1-carboxylate was obtained (180.0 mg, 56.4%).

¹H-NMR (DMSO, 500 MHz): δ 10.86 (1H, brs, —NH), 8.18 (1H, s, aromatic), 8.06 (1H, dd, J=9.1, 4.7 Hz, aromatic), 7.81 (1H, d, J=7.8 Hz, aromatic), 7.76 (2H, d, J=9.29 Hz, aromatic), 7.70 (1H, d, J=15.9 Hz, indole-CH=CH—), 7.50 (1H, m, aromatic), 7.25 (1H, dd, J=9.5, 2.2 Hz, aromatic), 7.18 (1H, m, aromatic), 6.78 (1H, d, J=15.9 Hz, indole-CH=CH—), 4.80 (1H, m, —N—CH—(CH₃)₂), 1.59 (9H, s, Boc), 1.15 (6H, m, —N—CH—(CH₃)₂)

Example 39

Preparation of (E)-3-fluoro-N'-(3-(1-isopentyl-1H-indol-3-yl)acryloyl)-N'-isopropylbenzohydrazide

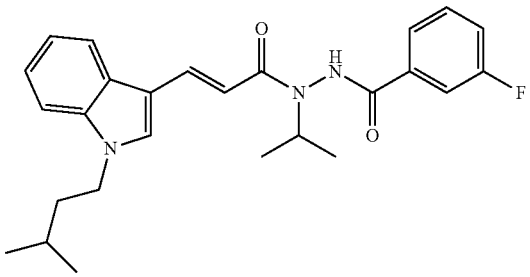 [SMILES: CC(C)CCn1cc(/C=C/C(=O)N(NC(=O)c2cccc(F)c2)C(C)C)c2ccccc21]

To solution containing (E)-3-(1-isopentyl-1H-indol-3-yl) acrylic acid (140.0 mg, 0.54 mmol), 3-fluoro-N'-isopropyl-benzohydrazide (158.9 mg, 0.81 mmol) and HATU (308.0 mg, 0.81 mmol) dissolved in DMF (3.0 ml), N,N-diisopropylethylamine (DIPEA)(0.14 ml, 0.81 mmol) was slowly drop-wise added and stirred at room temperature for 12 hr. The reaction mixture was diluted with EtOAc, washed with water and brine, dried with anhydrous MgSO₄, filtered, and concentrated under reduced pressure. The residue was separated through silica gel chromatography (30% EtOAc) for refinement and dried so that ivory (E)-3-fluoro-N'-(3-(1-isopentyl-1H-indol-3-yl)acryloyl)-N'-isopropylbenzohydrazide was obtained (104.0 mg, 44.2%).

¹H-NMR (CDCL₃, 500 MHz): δ 9.53 (1H, brs, —NH), 7.82 (1H, d, J=15.4 Hz, indole-CH=CH—), 7.75 (1H, d, J=7.6 Hz, aromatic), 7.70 (1H, d, J=6.6 Hz, aromatic), 7.55 (1H, s, aromatic), 7.38 (1H, d, J=5.4 Hz, aromatic), 7.24 (1H, d, J=9.3 Hz, aromatic), 7.15 (3H, m, aromatic), 6.94 (1H, s, aromatic), 6.78 (1H, d, J=15.7 Hz, indole-CH=CH—), 4.91 (1H, brs, —N—CH—(CH₃)₂), 3.91 (2H, m, —N—CH₂—CH₂—CH—(CH₃)₂), 1.58 (2H, d, J=6.8 Hz, —N—CH₂—CH₂—CH—(CH₃)₂), 1.49 (1H, m, —N—CH₂—CH₂—CH—(CH₃)₂), 1.19 (6H, m, —N—CH—(CH₃)₂), 0.89 (6H, m, —N—CH₂—CH₂—(CH₃)₂)

Example 40

Preparation of (E)-3-fluoro-N'-isopropyl-N'-(3-(1-methyl-1H-indol-3-yl)acryloyl)benzohydrazide

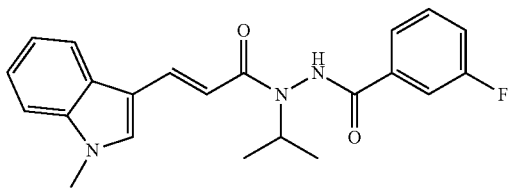 [SMILES: CC(C)N(NC(=O)c1cccc(F)c1)C(=O)/C=C/c1cn(C)c2ccccc12]

To solution containing (E)-3-(1-methyl-1H-indol-3-yl) acrylic acid (140.0 mg, 0.70 mmol), 3-fluoro-N'-isopropyl-benzohydrazide (209.0 mg, 1.05 mmol) and HATU (399.2 mg, 1.05 mmol) dissolved in DMF (3.0 ml), N,N-diisopropylethylamine (DIPEA)(0.18 ml, 1.05 mmol) was slowly drop-wise added and stirred at room temperature for 12 hr. The reaction mixture was diluted with EtOAc, washed with water and brine, dried with anhydrous MgSO₄, filtered, and concentrated under reduced pressure. The residue was separated through silica gel chromatography (30% EtOAc) for refinement and dried so that ivory (E)-3-fluoro-N'-isopropyl-N'-(3-(1-methyl-1H-indol-3-yl)acryloyl)benzohydrazide was obtained (37.0 mg, 13.9%).

¹H-NMR (MeOD, 500 MHz): δ 8.76 (1H, dd, J=4.4, 1.5 Hz, aromatic), 8.47 (1H, dd, J=8.4, 1.3 Hz, aromatic), 7.62 (2H, m, aromatic, indole-CH=CH—), 7.53 (3H, m, aromatic), 7.48 (2H, m, aromatic, indole-CH=CH—), 7.28 (2H, m, aromatic), 4.80 (1H, s, —N—CH—(CH₃)₂), 4.44 (3H, s, —N—CH₃), 1.12 (6H, d, J=6.4 Hz, —N—CH—(CH₃)₂)

Example 41

Preparation of (E)-N'-(3-(1-ethyl-1H-indol-3-yl) acryloyl)-3-fluoro-N'-isopropylbenzohydrazide

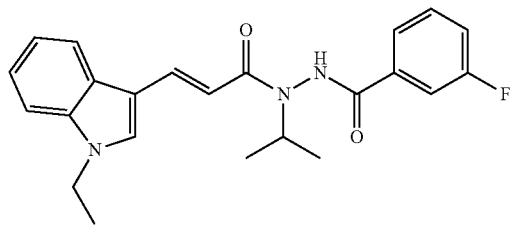 [SMILES: CCn1cc(/C=C/C(=O)N(NC(=O)c2cccc(F)c2)C(C)C)c2ccccc21]

To solution containing (E)-3-(1-ethyl-1H-indol-3-yl) acrylic acid (180.0 mg, 0.83 mmol), 3-fluoro-N'-isopropyl-benzohydrazide (245.3 mg, 1.25 mmol) and HATU (475.3 mg, 1.25 mmol) dissolved in DMF (5.0 ml), N,N-diisopropylethylamine (DIPEA)(0.22 ml, 1.25 mmol) was slowly drop-wise added and stirred at room temperature for 12 hr. The reaction mixture was diluted with EtOAc, washed with water and brine, dried with anhydrous MgSO₄, filtered, and concentrated under reduced pressure. The residue was separated through silica gel chromatography (30% EtOAc) and dried so that white (E)-N'-(3-(1-ethyl-1H-indol-3-yl)acryloyl)-3-fluoro-N'-isopropylbenzohydrazide was obtained (203.0 mg, 62.2%).

¹H-NMR (CDCL₃, 500 MHz): δ 9.47 (1H, brs, —NH), 7.82 (1H, d, J=15.4 Hz, aromatic), 7.75 (1H, d, J=7.3 Hz, aromatic), 7.69 (1H, d, J=6.6 Hz, indole-CH=CH—), 7.54 (1H, s, aromatic), 7.39 (1H, d, J=4.9 Hz, aromatic), 7.18 (4H, m, aromatic), 6.94 (1H, s, aromatic), 6.77 (1H, d, J=15.4 Hz, indole-CH=CH—), 4.91 (1H, brs, —N—CH₂—(CH₃)₂), 3.91 (2H, d, J=5.6 Hz, —N—CH₂—CH₃), 1.29 (3H, t, J=6.2 Hz, —N—CH₂—CH₃), 1.18 (6H, d, J=4.4 Hz, —N—CH—(CH₃)₂)

Example 42

Preparation of (E)-3-fluoro-N'-isopropyl-N'-(3-(1-propyl-1H-indol-3-yl)acryloyl)benzohydrazide

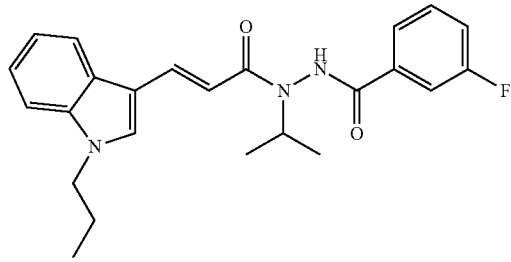 [SMILES: CCCn1cc(/C=C/C(=O)N(NC(=O)c2cccc(F)c2)C(C)C)c2ccccc21]

To solution containing (E)-3-(1-propyl-1H-indol-3-yl) acrylic acid (160.0 mg, 0.70 mmol), 3-fluoro-N'-isopropyl-benzohydrazide (206.0 mg, 1.05 mmol) and HATU (399.2 mg, 1.05 mmol) dissolved in DMF (3.0 ml), N,N-diisopropylethylamine (DIPEA)(0.18 ml, 1.05 mmol) was slowly drop-wise added and stirred at room temperature for 12 hr.

The reaction mixture was diluted with EtOAc, washed with water and brine, dried with anhydrous MgSO$_4$, filtered, and concentrated under reduced pressure. The residue was separated through silica gel chromatography (30% EtOAc) for refinement and dried so that white (E)-3-fluoro-N'-isopropyl-N'-(3-(1-propyl-1H-indol-3-yl)acryloyl)benzohydrazide was obtained (136.0 mg, 47.7%).

$^1$H-NMR (CDCL$_3$, 500 MHz): δ 9.32 (1H, brs, —NH̲), 7.83 (1H, d, J=15.4 Hz, aromatic), 7.75 (1H, d, J=7.3 Hz, aromatic), 7.69 (1H, d, J=5.1 Hz, indole-CH̲=CH—), 7.56 (1H, s, aromatic), 7.40 (1H, d, J=4.9 Hz, aromatic), 7.24 (1H, d, J=7.6 Hz, aromatic), 7.16 (3H, m, aromatic), 6.95 (1H, s, aromatic), 6.77 (1H, d, J=15.4 Hz, indole-CH=CH̲—), 4.91 (1H, brs, —N—CH̲—(CH$_3$)$_2$), 3.87 (2H, s, —N—CH̲$_2$—CH$_2$—CH$_3$), 1.72 (2H, d, J=6.6 Hz, —N—CH$_2$—CH̲$_2$—CH$_3$), 1.21 (6H, s, —N—CH—(CH̲$_3$)$_2$), 0.81 (3H, t, J=7.0 Hz, —N—CH$_2$—CH$_2$—CH̲$_3$)

Example 43

Preparation of (E)-tert-butyl 3-(3-(2-isonicotinoyl-1-isopropylhydrazinyl)-3-oxoprop-1-enyl)-1H-indole-1-carboxylate

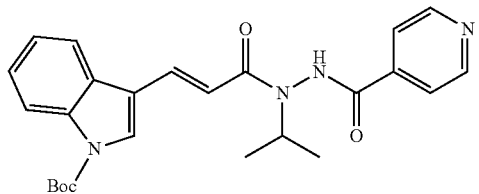 [SMILES: CC(C)N(NC(=O)c1ccncc1)C(=O)/C=C/c1cn(C(=O)OC(C)(C)C)c2ccccc12]

To solution containing (E)-3-(1-(tert-butoxycarbonyl)-1H-indol-3-yl)acrylic acid (200.0 mg, 0.70 mmol), N'-isopropylisonicotino hydrazide (188.2 mg, 1.05 mmol) and HATU (399.2 mg, 1.05 mmol) dissolved in DMF (5.0 ml), N,N-diisopropylethylamine (DIPEA)(0.18 ml, 1.05 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (n-hexane: EtOAc=3:1) for refinement and dried so that ivory (E)-tert-butyl 3-(3-(2-isonicotinoyl-1-isopropylhydrazinyl)-3-oxoprop-1-enyl)-1H-indole-1-carboxylate was obtained (108 mg, 34.4%).

$^1$H-NMR (MeOD, 500 MHz): δ 8.87 (2H, d, J=4.6 Hz, aromatic), 8.18 (1H, d, J=8.3 Hz, aromatic), 7.95 (3H, m, aromatic), 7.84 (1H, d, J=15.7 Hz, indole-CH̲=CH—), 7.58 (1H, m, aromatic), 7.34 (1H, t, J=7.6 Hz, aromatic), 7.13 (1H, m, aromatic), 6.96 (1H, d, J=15.2 Hz, indole-CH=CH̲—), 5.03 (1H, m, —N—CH̲—(CH$_3$)$_2$), 1.71 (9H, s, Boc), 1.33 (6H, m, —N—CH—(CH̲$_3$)$_2$)

Example 44

Preparation of (E)-tert-butyl 3-(3-(2-(4-fluorobenzoyl)-1-isopropylhydrazinyl)-3-oxoprop-1-enyl)-1H-indole-1-carboxylate

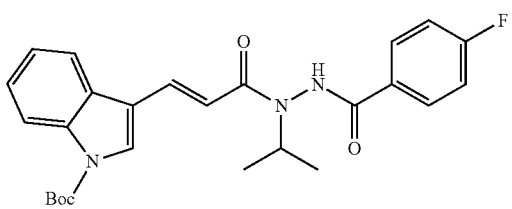 [SMILES: CC(C)N(NC(=O)c1ccc(F)cc1)C(=O)/C=C/c1cn(C(=O)OC(C)(C)C)c2ccccc12]

To solution containing 3-(1H-indol-3-yl)-acrylic acid 3-(1H-indol-3-yl)-acrylic acid (200.0 mg, 0.7 mmol), 4-fluoro-N'-isopropylbenzohydrazide (206.0 mg, 1.05 mmol) and HATU (399.2 mg, 1.05 mmol) dissolved in DMF (5.0 ml), N,N-diisopropylethylamine (DIPEA)(0.18 ml, 1.05 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (36% EtOAc) for refinement and dried so that white (E)-tert-butyl 3-(3-(2-(4-fluorobenzoyl)-1-isopropylhydrazinyl)-3-oxoprop-1-enyl)-1H-indole-1-carboxylate was obtained (162.0 mg, 49.7%).

$^1$H-NMR (MeOD, 500 MHz): δ 8.11 (1H, d, J=8.3 Hz, aromatic), 8.03 (2H, m, aromatic), 7.83 (1H, s, aromatic), 7.76 (1H, d, J=15.7 Hz, indole-CH̲=CH—), 7.48 (1H, d, J=7.6 Hz, aromatic), 7.29 (3H, m, aromatic), 7.03 (1H, t, J=7.3 Hz, aromatic), 6.91 (1H, d, J=15.7 Hz, indole-CH=CH̲—), 4.95 (1H, m, —N—CH̲—(CH$_3$)$_2$), 1.64 (9H, s, Boc), 1.25 (6H, m, —N—CH—(CH̲$_3$)$_2$)

Example 45

Preparation (E)-tert-butyl 3-(3-(2-(3-chlorobenzoyl)-1-isopropylhydrazinyl)-3-oxoprop-1-enyl)-1H-indole-1-carboxylate

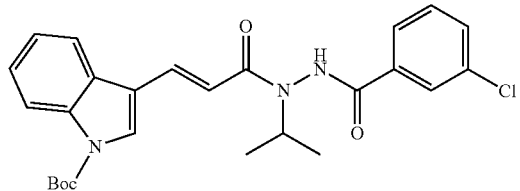 [SMILES: CC(C)N(NC(=O)c1cccc(Cl)c1)C(=O)/C=C/c1cn(C(=O)OC(C)(C)C)c2ccccc12]

To solution containing (E)-3-(1-(tert-butoxycarbonyl)-1H-indol-3-yl)acrylic acid (200.0 mg, 0.70 mmol), 3-chloro-N'-isopropylbenzohydrazide (223.3 mg, 1.05 mmol) and HATU (399.2 mg, 1.05 mmol) dissolved in DMF (5.0 ml), N,N-diisopropylethylamine (DIPEA)(0.18 ml, 1.05 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (40% EtOAc) for refinement and dried so that white ((E)-tert-butyl 3-(3-(2-(3-chlorobenzoyl)-1-isopropylhydrazinyl)-3-oxoprop-1-enyl)-1H-indole-1-carboxylate was obtained (166.0 mg, 49.2%).

$^1$H-NMR (MeOD, 500 MHz): δ 8.11 (1H, d, J=8.3 Hz, aromatic), 7.97 (1H, s, aromatic), 7.88 (1H, d, J=7.6 Hz, aromatic), 7.84 (1H, s, aromatic), 7.76 (1H, d, J=15.7 Hz, indole-CH̲=CH—), 7.65 (1H, d, J=7.6 Hz, aromatic), 7.55 (1H, t, J=7.8 Hz, aromatic), 7.50 (1H, d, J=7.3 Hz, aromatic), 7.27 (1H, t, J=7.7 Hz, aromatic), 7.06 (1H, t, J=6.5 Hz, aromatic), 6.90 (1H, d, J=15.9 Hz, indole-CH=CH̲—), 4.94 (1H, m, —N—CH̲—(CH$_3$)$_2$), 1.64 (9H, s, Boc), 1.26 (6H, m, —N—CH—(CH̲$_3$)$_2$)

Example 46

Preparation of (E)-4-fluoro-N'-(3-(1-isopentyl-1H-indol-3-yl)acryloyl)-N'-isopropylbenzohydrazide

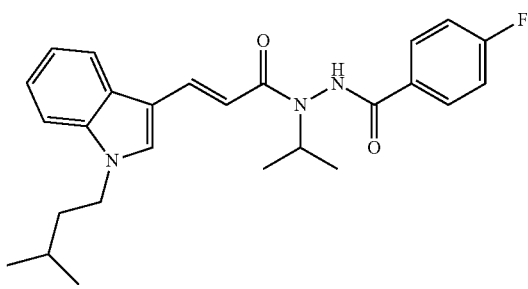 [SMILES: CC(C)CCn1cc(/C=C/C(=O)N(NC(=O)c2ccc(F)cc2)C(C)C)c2ccccc21]

To solution containing (E)-3-(1-isopentyl-1H-indol-3-yl)acrylic acid (170 mg, 0.66 mmol), 4-fluoro-N'-isopropylbenzohydrazide (194.3 mg, 0.99 mmol) and HATU (376.4 mg, 0.99 mmol) dissolved in DMF (3.0 ml), N,N-diisopropylethylamine (DIPEA)(0.17 ml, 0.99 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (30% EtOAc) for refinement and dried so that ivory (E)-4-fluoro-N'-(3-(1-isopentyl-1H-indol-3-yl)acryloyl)-N'-isopropylbenzohydrazide was obtained (160.0 mg, 55.7%).

$^1$H-NMR (CDCL$_3$, 500 MHz): δ 9.73 (1H, brs, —NH), 7.99 (2H, s, aromatic), 7.82 (1H, d, J=15.4 Hz, indole-CH=CH—), 7.50 (1H, s, aromatic), 7.23 (1H, m, aromatic), 7.07 (4H, m, aromatic), 6.88 (1H, s, indole-CH=CH—), 4.89 (1H, brs, —N—CH—(CH$_3$)$_2$), 3.88 (2H, s, —N—CH$_2$—CH$_2$—CH—(CH$_3$)$_2$), 1.56 (2H, d, J=5.9 Hz, —N—CH$_2$—CH$_2$—CH—(CH$_3$)$_2$), 1.48 (1H, m, —N—CH$_2$—CH$_2$—CH—(CH$_3$)$_2$), 1.15 (6H, s, —N—CH—(CH$_3$)$_2$), 0.88 (6H, s, —N—CH$_2$—CH$_2$—(CH$_3$)$_2$)

Example 47

Preparation of (E)-tert-butyl 3-(3-(1-isopropyl-2-(3-methylbenzoyl)hydrazinyl)-3-oxoprop-1-enyl)-1H-indole-1-carboxylate

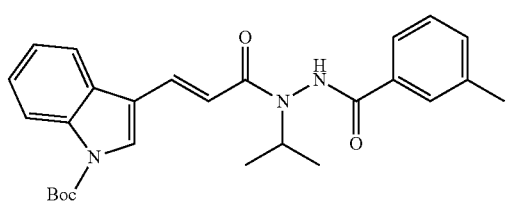 [SMILES: Cc1cccc(C(=O)NN(C(=O)/C=C/c2cn(C(=O)OC(C)(C)C)c3ccccc23)C(C)C)c1]

To solution containing (E)-3-(1-(tert-butoxycarbonyl)-1H-indol-3-yl)acrylic acid (150.0 mg, 0.52 mmol), N'-isopropyl-3-methylbenzohydrazide (150.0 mg, 0.78 mmol) and HATU (296.6 mg, 0.78 mmol) dissolved in DMF (3.0 ml), N,N-diisopropylethylamine (DIPEA)(0.14 ml, 0.78 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (30% EtOAc) for refinement and dried so that white (E)-tert-butyl 3-(3-(1-isopropyl-2-(3-methylbenzoyl)hydrazinyl)-3-oxoprop-1-enyl)-1H-indole-1-carboxylate was obtained (92.0 mg, 48.3%).

$^1$H-NMR (CDCL$_3$, 500 MHz): δ 8.81 (1H, brs, —NH), 8.07 (1H, d, J=7.3 Hz, aromatic), 7.73 (3H, m, aromatic, indole-CH=CH—), 7.63 (1H, s, aromatic), 7.48 (1H, s, aromatic), 7.35 (2H, s, aromatic), 7.24 (1H, m, aromatic), 7.00 (1H, s, aromatic), 6.88 (1H, d, J=15.7 Hz, indole-CH=CH—), 4.95 (1H, m, —N—CH—(CH$_3$)$_2$), 2.38 (3H, s, aromatic-CH$_3$), 1.64 (9H, s, Boc), 1.21 (6H, d, J=3.7 Hz, —N—CH—(CH$_3$)$_2$)

Example 48

Preparation of (E)-tert-butyl 3-(3-(1-isopropyl-2-(4-methylbenzoyl)hydrazinyl)-3-oxoprop-1-enyl)-1H-indole-1-carboxylate

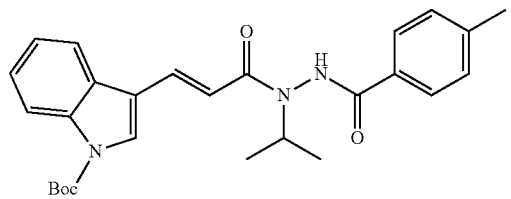 [SMILES: Cc1ccc(C(=O)NN(C(=O)/C=C/c2cn(C(=O)OC(C)(C)C)c3ccccc23)C(C)C)cc1]

To solution containing (E)-3-(1-(tert-butoxycarbonyl)-1H-indol-3-yl)acrylic acid (150.0 mg, 0.52 mmol), N'-isopropyl-4-methylbenzohydrazide (150.0 mg, 0.78 mmol) and HATU (296.6 mg, 0.78 mmol) dissolved in DMF (3.0 ml), N,N-diisopropylethylamine (DIPEA)(0.14 ml, 0.78 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (30% EtOAc) for refinement and dried so that white (E)-tert-butyl 3-(3-(1-isopropyl-2-(4-methylbenzoyl)hydrazinyl)-3-oxoprop-1-enyl)-1H-indole-1-carboxylate was obtained (141.0 mg, 58.8%).

$^1$H-NMR (MeOD, 500 MHz): δ 8.03 (1H, d, J=8.1 Hz, aromatic), 7.85 (2H, d, J=7.8 Hz, aromatic), 7.71 (2H, m, aromatic, indole-CH=CH—), 7.43 (1H, d, J=7.3 Hz, aromatic), 7.31 (2H, d, J=7.6 Hz, aromatic), 7.19 (1H, t, J=7.2 Hz, aromatic), 6.92 (2H, m, aromatic, indole-CH=CH—), 4.94 (1H, m, —N—CH—(CH$_3$)$_2$)), 2.37 (3H, s, aromatic-CH$_3$), 1.59 (9H, s, Boc), 1.24 (6H, m-N—CH—(CH$_3$)$_2$)

Example 49

Preparation of (E)-4-fluoro-N'-isopropyl-N'-(3-(1-(3-methylbut-2-enyl)-1H-indol-3-yl)acryloyl)benzohydrazide

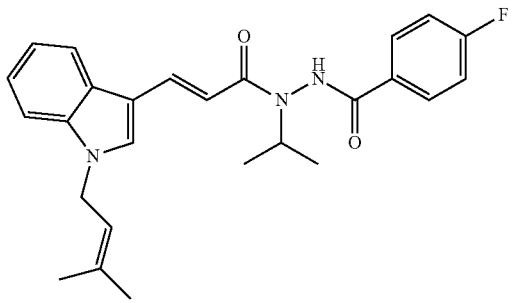 [SMILES: CC(C)=CCn1cc(/C=C/C(=O)N(NC(=O)c2ccc(F)cc2)C(C)C)c2ccccc21]

To solution containing (E)-3-(1-(3-methylbut-2-enyl)-1H-indol-3-yl)acrylic acid (161 mg, 0.63 mmol), 4-fluoro-N'-isopropylbenzohydrazide (82.4 mg, 0.42 mmol) and HATU (239.5 mg, 0.63 mmol) dissolved in DMF (3.0 ml), N,N-diisopropylethylamine (DIPEA)(0.11 ml, 0.63 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (35% EtOAc) for refinement and dried so that ivory (E)-4-fluoro-N'-isopropyl-N'-(3-(1-(3-methylbut-2-enyl)-1H-indol-3-yl)acryloyl)benzohydrazide was obtained (116.0 mg, 42.5%).

$^1$H-NMR (CDCL$_3$, 500 MHz): δ 9.16 (1H, brs, —NH), 7.96 (2H, m, aromatic), 7.83 (1H, d, J=15.4 Hz, indole-CH═CH—), 7.52 (1H, s, aromatic), 7.24 (1H, d, J=10.5 Hz, aromatic), 7.11 (4H, m, aromatic), 6.93 (1H, s, aromatic), 6.75 (1H, d, J=15.7 Hz, indole-CH═CH—), 5.22 (1H, s, —N—CH$_2$—CH═(CH$_3$)$_2$), 4.89 (1H, brs, —N—CH—(CH$_3$)$_2$), 4.49 (2H, s, —N—CH$_2$—CH═(CH$_3$)$_2$), 1.74 (6H, d, J=12.5 Hz, —N—CH$_2$—CH═(CH$_3$)$_2$), 1.18 (6H, s, —N—CH—(CH$_3$)$_2$)

Example 50

Preparation of (E)-N'-isopropyl-3-methyl-N'-(3-(1-(3-methylbut-2-enyl)-1H-indol-3-yl)acryloyl)benzohydrazide

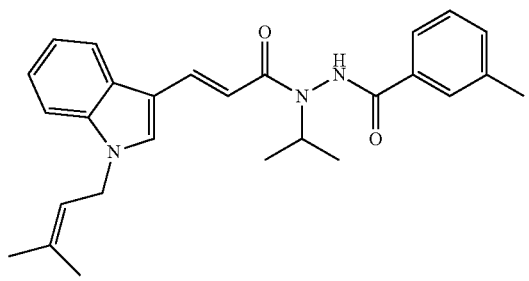 [SMILES: CC(C)=CCn1cc(/C=C/C(=O)N(NC(=O)c2cccc(C)c2)C(C)C)c2ccccc21]

To solution containing (E)-3-(1-(3-methylbut-2-enyl)-1H-indol-3-yl)acrylic acid (100.0 mg, 0.39 mmol), N'-isopropyl-3-methylbenzohydrazide (113.4 mg, 0.59 mmol) and HATU (224.3 mg, 0.59 mmol) dissolved in DMF (3.0 ml), N,N-diisopropylethylamine (DIPEA)(0.10 ml, 0.59 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (35% EtOAc) for refinement and dried so that white (E)-N'-isopropyl-3-methyl-N'-(3-(1-(3-methylbut-2-enyl)-1H-indol-3-yl)acryloyl)benzohydrazide was obtained (115.0 mg, 68.7%).

$^1$H-NMR (CDCL$_3$, 500 MHz): δ 9.07 (1H, brs, —NH), 7.77 (3H, m, aromatic, indole-CH═CH—), 7.56 (1H, d, J=7.1 Hz, aromatic), 7.31 (2H, s, aromatic), 7.22 (1H, d, J=8.3 Hz, aromatic), 7.13 (2H, m, aromatic), 6.92 (1H, s, aromatic), 6.78 (1H, d, J=15.4 Hz, indole-CH═CH—), 5.19 (1H, m, —N—CH$_2$—CH═(CH$_3$)$_2$), 4.92 (1H, brs, —N—CH—(CH$_3$)$_2$), 4.46 (2H, d, J=6.4 Hz, —N—CH$_2$—CH═(CH$_3$)$_2$), 2.36 (3H, s, aromatic-CH$_3$), 1.72 (6H, d, J=12.7 Hz, —N—CH$_2$—CH═(CH$_3$)$_2$), 1.18 (6H, d, J=5.6 Hz, —N—CH—(CH$_3$)$_2$)

Example 51

Preparation of (E)-N'-isopropyl-4-methyl-N'-(3-(1-(3-methylbut-2-enyl)-1H-indol-3-yl)acryloyl)benzohydrazide

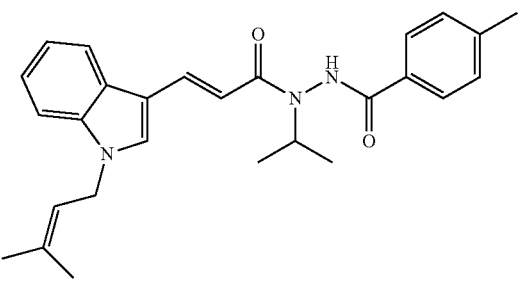 [SMILES: CC(C)=CCn1cc(/C=C/C(=O)N(NC(=O)c2ccc(C)cc2)C(C)C)c2ccccc21]

To solution containing (E)-3-(1-(3-methylbut-2-enyl)-1H-indol-3-yl)acrylic acid (100.0 mg, 0.39 mmol), N'-isopropyl-4-methylbenzohydrazide (113.4 mg, 0.59 mmol) and HATU (224.3 mg, 0.59 mmol) dissolved in DMF (3.0 ml), N,N-diisopropylethylamine (DIPEA)(0.10 ml, 0.59 mmol) was slowly drop-wise added and stirred at room temperature for 12 hr. The reaction mixture was diluted with EtOAc, washed with water and brine, dried with anhydrous MgSO$_4$, filtered, and concentrated under reduced pressure. The residue was separated through silica gel chromatography (35% EtOAc) for refinement and dried so that white (E)-N'-isopropyl-4-methyl-N'-(3-(1-(3-methylbut-2-enyl)-1H-indol-3-yl)acryloyl)benzohydrazide was obtained (74.0 mg, 44.1%).

$^1$H-NMR (CDCL$_3$, 500 MHz): δ 9.50 (1H, brs, —NH), 7.84 (3H, m, aromatic, indole-CH═CH—), 7.57 (1H, d, J=9.6 Hz, aromatic), 7.25 (3H, m, aromatic), 7.17 (2H, m, aromatic), 6.97 (1H, s, aromatic), 6.75 (1H, d, J=15.4 Hz, indole-CH═CH—), 5.26 (1H, t, J=6.4 Hz, —N—CH$_2$—CH═(CH$_3$)$_2$), 4.96 (1H, brs, —N—CH—(CH$_3$)$_2$), 4.53 (2H, d, J=6.8 Hz, —N—CH$_2$—CH═(CH$_3$)$_2$), 2.38 (3H, s, aromatic-CH$_3$), 1.75 (6H, d, J=14.2 Hz, —N—CH$_2$—CH═(CH$_3$)$_2$), 1.22 (6H, d, J=6.4 Hz, —N—CH—(CH$_3$)$_2$)

Experimental Example 1

DGAT Enzyme Inhibition Test

To investigate inhibitory effect of the compounds of Examples 1-33 against DGAT enzyme activity, DGAT enzyme inhibition and DGAT2 selectivity were investigated using zymogen including:
1) hDGAT1 and hDGAT2 enzymes, derived from insect cell overexpressing human DGAT1 and DGAT2 ('sf9'), respectively,
2) DGAT enzyme derived from human duodenal adenocarcinoma ('Hutu 80'), and
3) rat liver-derived DGAT enzyme.

To be specific, for the purpose of measuring human-derived DGAT enzyme inhibitory activity, using the zymogen, including enzymes derived from insect cell overexpressing human DGAT1 and DGAT2 ('sf9'), microsomal protein isolated from human duodenal adenocarcinoma ('Hutu 80'), and microsomal protein isolated from rat, and according to Coleman et al., (*Methods Enzymol.*, 98-103, 1992), and substrate including 1,2-diacylglycerol(Sigma, D0138) and [$^{14}$C] palmitoyl-CoA (Amersham, CFA583), the amount of radiation of [$^{14}$C]triacylglycerol produced after enzymatic reaction was measured.

To be more specific, to the reaction solution containing 175 mM Tris-HCl (pH 8.0), 20 μl bovine serum albumin (10 mg/ml), 100 mM magnesium chloride, 30 μM [$^{14}$C]palmitoyl CoA (0.02 μCi, Amersham) and 200 μM 1,2-dioleoylglycerol, reagent dissolved in dimethylsulfoxide (10.0 μl) was added. After introducing 100 to 200 μg isolated microsomal protein and allowing the same to react at 25° C. for 10 min, the reaction was stopped by adding 1.5 ml stop solution (2-propanol:heptane:water=80:20:2, v:v:v). To isolate the product of the reaction (i.e., [$^{14}$C]triacylglycerol), 1 ml heptane and 0.5 ml distilled water were added and then decocted. After taking 1 ml supernatant, 2 ml alkaline ethanol solution (ethanol:0.5 N sodium hydroxide:water=50:10:40, v:v:v) were added and then decocted. After taking 0.65 ml supernatant from the decoction, the amount of radiation was measured with liquid scintillation counter (LSC). The DGAT inhibitory activity was calculated with Mathematical Expression 1 below:

$$\text{Inhibitory Activity (\%)} = \left(1 - \frac{T-B}{C-B}\right) \times 100 \quad \text{Mathematical Expression 1}$$

where,

T denotes cpm of experimental group in which the enzymatic reaction solution was treated with the sample, C denotes cpm of control group in which the enzymatic reaction solution was not treated with the sample, and B denotes cpm of control group treated with the sample without zymogen.

The result of the above experiment is tabulated below.

TABLE 2

| Ex. | hDGAT-1 (sf9) IC$_{50}$ (μM) | hDGAT-2 (sf9) inhibition rate(%) at 10 μM | hDGAT-1 (HuTu 80) IC$_{50}$ (μM) | DGAT-1 (rat liver) IC$_{50}$ (μM) |
|---|---|---|---|---|
| 1 | 9.6 | 7.5 | 1.4 | 1.1 |
| 2 | >100 | —[a] | 11.2 | 7.6 |
| 3 | >100 | — | 6.5 | 3.9 |
| 4 | >100 | — | 12.4 | 22.4 |
| 5 | 22.5 | — | 6.6 | 16.3 |
| 6 | >100 | 0.3 | 5.2 | 2.1 |
| 7 | >100 | — | 11.6 | 8.7 |
| 8 | >100 | — | 9.3 | 2.5 |
| 9 | >100 | — | 19.6 | 11.8 |
| 10 | 36.4 | 8.3 | 7.7 | 2.6 |
| 11 | >100 | — | 10.0 | 3.7 |
| 12 | 6.8 | 3.9 | 2.6 | 1.7 |
| 13 | 20.4 | 2.3 | 8.1 | 9.1 |
| 14 | 8.8 | — | 2.7 | 2.8 |
| 15 | 20.4 | — | 1.1 | 0.4 |
| 16 | >100 | 3.7 | 10.7 | 26.3 |
| 17 | >100 | — | >100 | 83.6 |
| 18 | >100 | — | 3.2 | 20.3 |
| 19 | >100 | — | >100 | 45.5 |
| 20 | >100 | — | 73.3 | >100 |
| 21 | >100 | 1.3 | 29.6 | 29.1 |
| 22 | >100 | — | 44.6 | 33.0 |
| 23 | 95.1 | — | 25.8 | 31.4 |
| 24 | >100 | — | 9.2 | 8.6 |
| 25 | 28.3 | — | 29.2 | 9.3 |
| 26 | 13.6 | 5.0 | 2.9 | 2.4 |
| 27 | 11.8 | 1.2 | 2.6 | 0.5 |
| 28 | 41.6 | — | 8.1 | 2.9 |
| 29 | 24.6 | — | 4.6 | 1.9 |
| 30 | 65.3 | — | 27.0 | 22.5 |
| 31 | 9.3 | 4.4 | 5.1 | 3.4 |
| 32 | 5.7 | 11.0 | 0.97 | 0.7 |
| 33 | 5.3 | — | 2.1 | 1.4 |
| 34 | 7.2 | 18.5 | ND | ND |
| 35 | 3.2 | 2.0 | ND | ND |
| 36 | >100 | 3.6 | ND | ND |
| 37 | >100 | 2.9 | ND | ND |
| 38 | >100 | — | ND | ND |
| 39 | 1.8 | 42.3 | ND | ND |
| 40 | >100 | 2.2 | ND | ND |
| 41 | 8.1 | 20.3 | ND | ND |
| 42 | 3.6 | 32.4 | ND | ND |
| 43 | 4.0 | 0.6 | ND | ND |
| 44 | 2.1 | 28.9 | ND | ND |
| 45 | 2.2 | 28.7 | ND | ND |
| 46 | 1.0 | 64.0 | ND | ND |
| 47 | 2.9 | 34.1 | ND | ND |
| 48 | 9.8 | 22.1 | ND | ND |
| 49 | 1.5 | 28.0 | ND | ND |
| 50 | 4.6 | 39.0 | ND | ND |
| 51 | 9.9 | 37.1 | ND | ND |

[a]—: no inhibition

As shown in Table 2, as a result of measuring DGAT enzyme inhibitory activity using enzyme isolated from insect cells ('sf9') overexpressing hDGAT1 and hDGAT2, with 1,2-diacylglycerol and [$^{14}$C] palmitoyl-CoA as substrate, it was revealed that the compounds of Examples 1, 5, 10, 12, 13, 14, 15, 26 to 29, 31 to 35, 39 and 41 to 51 exhibited superior hDGAT1 enzyme activity concentration-dependently. In addition, the compounds of Examples 1, 5, 10, 12, 13, 14, 15, 26 to 29, 31 to 33, 35 and 43 exhibited less than 11% hDGAT2 inhibition at a concentration of 10 μM, thus indicating that it provides selective inhibitory effect on hDGAT1.

Accordingly, since the indole derivative according to the present invention effectively inhibited the activity of the DGAT enzyme, the indole derivative can be advantageously used as a pharmaceutical composition for preventing or treating metabolic diseases.

Experimental Example 2

DGAT Inhibitory Effect in Hep62 Cells

To investigate inhibition effect on intracellular DGAT enzyme activity of the compounds obtained in Examples 1-51, intracellular DGAT enzyme activity was measured using human-derived liver HepG2 cells.

HepG2 cells were purchased from ATCC, and cultured in 37° C., 5% CO$_2$ incubator including minimum essential medium (2 mM L-glutamine, earle's BSS adjusted to contain 1.5 g/L sodium bicarbonate, 0.1 mM nonessential amino acids, and 1 mM sodium pyruvate) added with 10% fetal bovine serum (FBS) and 1% antibiotic (100 U/ml penicillin and 100 g/ml streptomycin).

The intracellular DGAT enzyme activity was measured based on an amount of triglycerides produced in the cultured HepG2 cells, by adding 10 μM enzyme inhibitor compounds obtained in Examples 1-51, respectively, and then determining the effect of the enzyme inhibitors according to reduction rate of the triglyceride production.

Specifically, cells were seeded 1×10$^6$ cell/ml per well of the 24 well culture plate, and 24 hours after incubation, medium was exchanged with FBS-free DMEM medium, and sample of 0.2 mCi [$^{14}$C]glycerol (Amersham) was added as substrate, and the reaction was allowed to occur for 6 hr. The induced production of triglyceride was catalyzed by the DGAT enzyme, and DGAT enzyme activity was determined based on the amount of production of triglyceride which was measured based on the amount of radiation. The sample was dissolved in dimethylsulfoxide (DMSO) to be used, and the control group in the triglyceride production reaction was reacted with dimethylsulfoxide only (i.e., without sample), and the amount of the triglyceride production rate was set to 100.

After the reaction completed, the substrate [$^{14}$C]glycerol which was either not absorbed into cells or not used for the reaction, were removed with phosphate-buffer-saline (PBS), and 0.5 ml extraction solvent (hexane:isopropanol=3:2, v:v) was added to extract full fat containing triglycerides. With 0.5 ml extraction solvent, extract was obtained two times for 30 min each, and 1 ml of the extract was concentrated with nitrogen gas. After removing the extraction solvent, the total fat was dissolved in organic solvent (chloroform:methanol=2:1) and spotted with thin-layer chromatography (TLC: silica gel 60F254, thickness: 0.5 mm, Merck) on the developing solvent (hexane:diethyl ether:acetic acid=80:20:1, v: v: v). Triglycerides (Rf value: 0.4) were isolated on TLC, and after exposing the TLC plate to the film with photosensitivity to radiation energy (imaging plate' Fujifilm, BMS-MS 2040) for 3 hr, the amount of [$^{14}$C] radiation of triglyceride was measured by imaging analysis (FLA 7000). The remaining cells after the extraction were dissolved in 0.3 ml 0.1 N sodium hydroxide for use in the measurement of protein concentration of the cells used for the reaction.

The experimental errors among the respective experimental groups were compensated with the experimental value which was obtained by dividing the measured radiation of triglyceride by protein concentration, and the production rate of triglyceride according to the respective compounds of Examples 1-51 are tabulated below.

TABLE 3

| Ex. | Triglyceride production rate (%)/HepG2 cells at 10 μM |
|---|---|
| 1 | 60.1 |
| 2 | 64.2 |
| 3 | 66.8 |
| 4 | 86.7 |
| 5 | 62.2 |
| 6 | 74.8 |
| 7 | 85.8 |
| 8 | 85.2 |
| 9 | 83.79 |
| 10 | 62.0 |
| 11 | 72.6 |
| 12 | 93.5 |
| 13 | 87.1 |
| 14 | 84.4 |
| 15 | 71.2 |
| 16 | 61.7 |
| 17 | 81.7 |
| 18 | 102.3 |
| 19 | 102.6 |
| 20 | 109.4 |
| 21 | 103.1 |
| 22 | 115.6 |
| 23 | 87.7 |
| 24 | 60.7 |
| 25 | 88.61 |
| 26 | 59.8 |
| 27 | 58.5 |
| 28 | 64.4 |
| 29 | 59.6 |
| 30 | 89.0 |
| 31 | 93.3 |

TABLE 3-continued

| Ex. | Triglyceride production rate (%)/HepG2 cells at 10 μM |
|---|---|
| 32 | 91.4 |
| 33 | 78.2 |
| 34 | 58.0 |
| 35 | 57.6 |
| 36 | 75.0 |
| 37 | 79.2 |
| 38 | 85.7 |
| 39 | 50.8 |
| 40 | 90.0 |
| 41 | 79.4 |
| 42 | 79.9 |
| 43 | 81.3 |
| 44 | 94.8 |
| 45 | 97.9 |
| 46 | 63.5 |
| 47 | 74.7 |
| 48 | 96.7 |
| 49 | 55.7 |
| 50 | N.D. |
| 51 | N.D. |

As shown in Table 3, as a result of measuring inhibition effect against biosynthesis of triglycerides of the compounds obtained in Examples 1-51, by treating human-derived hepatoma cells (HepG2) with 10 μM concentration of the respective compounds, the compounds of Examples 1 to 3, 5, 10, 16, 24, 26 to 29, 34, 35, 39, 46 and 49 exhibited 30-40% biosynthesis inhibition rate of triglyceride, and the compounds of Examples 6, 11, 15, 33, 36, 37, 41, 42 and 47 exhibited 20-30% biosynthesis inhibition rate of triglyceride, respectively. In other words, it was confirmed that the compounds according to the present invention enter the cells to inhibit DGAT1 enzyme activity and thus inhibit biosynthesis of triglyceride within the cells.

Therefore, according to the present invention, the indole derivative effectively inhibits biosynthesis of triglycerides within the cells, and thus can be advantageously used as a pharmaceutical composition for the prevention or treatment of metabolic diseases.

Experimental Example 3

DGAT Activity Inhibitory Effect in HuTu80 Cells

HuTu80 cells were seeded in 24-well culture plate by $2 \times 10^5$ cells/well. After 24 hr, the medium was exchanged with FBS-free DMEM and concurrently treated with sample and substrate. For the substrate, 0.5 μCi [$^{14}$C]oleate was respectively added and allowed to react for 2 hr. After the reaction, the substrate that was either not absorbed into cells or not used for the reaction were washed with PBS two times, and total fat containing triglyceride was extracted by adding 1 ml extraction solvent (n-hexane/2-propanol=3/2, v/v). The extract was concentrated with nitrogen gas. The total fat after elimination of extraction solvent was dissolved in organic solvent (chloroform/methanol=2/1, v/v), spotted on thin layer chromatography (TLC: silica gel 60F$_{254}$, 0.5 mm, Merck), and developed on developing solvent (n-hexane/diethyl ether/acetic acid=80/20/1, v/v/v). After isolating triglyceride (R$_f$ value: 0.4) from TLC, exposing to the film with photosensitivity to energy of radioactive elements (imaging plate's Fujifilm, BAS-MS 2040) for 3 hr, and the radioactive dose of triglyceride was measured by conducting image analysis (FLA 7000).

The remaining cells after the extraction were dissolved in 0.3 ml 0.1N NaOH to measure the protein concentration of the cells used for the reaction. The protein quantification was performed with Lowry method-based, protein quantification kit (Bio-Rad). After seeding protein on 96-well, round bottom culture plate, 25 μl of solution containing 1 ml protein analysis reagent (bio-rad, alkaline copper tartrate solution) and 20 μl protein reagent S (bio-rad, surfactant solution) was seeded per well, to induce reaction between copper ion and protein. After reaction with copper ion, 200 μl reagent B (bio-rad, folin reagent) was seeded per well to allow reduction reaction of the folin reagent to occur. For the amount of protein, the light absorptivity at 750 nm was measured based on the blue coloring of the folin reagent as the reduction occurred, and the concentrations of the protein corresponding to respective light absorptivities were quantified by obtaining standard curves with the standard material as bovine serum albumin (BSA). Using the experiment value, which is obtained by dividing the measured radiation dose of the triglyceride by the protein concentration, the above process was repeated three or more times, and the mean value with ±standard error was obtained, as tabulated below.

TABLE 4

| Ex. | Triglyceride Production Rate (% of control)/HuTu80cells | | | |
| --- | --- | --- | --- | --- |
|  | 10 μM | 3 μM | 1 μM | 0.3 μM |
| Ex. 27 | 13.1 ± 0.9 | ND | ND | ND |
| Ex. 44 | 20.0 ± 1.2 | 29.0 ± 0.9 | 43.7 ± 0.3 | 63.9 ± 4.3 |
| Ex. 46 | 20.0 ± 1.8 | 20.0 ± 1.2 | 30.0 ± 1.3 | 30.0 ± 0.3 |
| Ex. 47 | 13.7 ± 1.5 | 19.0 ± 5.0 | 30.2 ± 1.2 | 56.1 ± 0.1 |
| Ex. 48 | 23.9 ± 0.8 | ND | ND | ND |
| Ex. 49 | 13.1 ± 0.9 | 21.4 ± 0.3 | 33.4 ± 4.4 | 66.9 ± 3.0 |

Referring to Table 3, the human duodenal adenocarcinoma cells (Hutu 80 cells) were treated with [$^{14}$C]oleate, and the inhibitory effect on intracellular biosynthesis of triglycerides was measured. As a result, the five compounds of Examples 27, 44, 46, 47 and 49 exhibited superior inhibitory activity (approx. 70-80%) at 10 uM concentration. Among the compounds, those of Examples 44, 46, 47 and 49 particularly inhibited biosynthesis of triglycerides in a concentration-dependent manner, by inhibiting DGAT1 in Huto 80 cells. Accordingly, it was confirmed that the compounds according to the present invention enter the cells to inhibit DGAT1 enzyme activity and thus inhibit biosynthesis of triglyceride within the cells.

Therefore, according to the present invention, the indole derivative effectively inhibits biosynthesis of triglycerides within the cells, and thus can be advantageously used as a pharmaceutical composition for the prevention or treatment of metabolic diseases.

Experimental Example 4

Oral Lipid Tolerance Test (OLTT) on Compounds

For experiment, 8-week-old male C57BL/6J mice were purchased from Biolink, adapted to environment in bio clean room (Temp. 22±3° C., Humidity 50±10%, Lighting 12 hr interval) for 1 week, and one day before the experiment, fasted for 16 hr. The mice were allowed to freely eat radiation-sterilized solid rodent feed (Harlan, Ind., USA), except for the 16 hr fasting period before the administration of test sample, and were also allowed to freely have a sufficient amount of drinking water which was sterilized in autoclave throughout the test period.

Seven C57BL/6J mice were allocated for solvent control group (V.C., Vehicle Control), and another seven for experimental group (sample group), after which sample was administered as follows.

The normal control group was administered with administration medium (0.5% CMC; carboxy methyl cellulose) only, while the experimental group was orally administered with the compounds of Examples 27 and 49 by 10, 30 mg/kg concentrations, respectively. Before administering the samples to all the animals of the experimental group, the animals were fasted for 16 hr, after which the corresponding sample was orally administered one time, using sonde for oral administration. After 60 min, 6 ml/kg liquid measure of corn oil was orally administered. Blood samples were taken immediately before administration of the corn oil (at 0 hr), and after the corn coil administration, the blood samples were taken directly using heparin-treated capillary tube from retro-orbital sinus at predetermined time (at 2 hr and at 4 hr). The blood samples were centrifuged at 3,000 rpm for 10 min to separate plasma, and the concentration of triglyceride was directly analyzed with automated hematology chemistry analyzer (Hitachi 7150, Japan). The results are tabulated below.

TABLE 5

| (n = 7) | Dose (mg/kg) | Serum TG (mg/dl) | | |
| --- | --- | --- | --- | --- |
|  |  | 0 hr | 2 hr | 4 hr |
| Solvent control (0.5% CMC) | 0 | 45.2 ± 9.8 | 196.6 ± 74.6 | 110.2 ± 49.5 |
| Ex. 27 | 10 | 62.8 ± 20.6 | 171.0 ± 61.7 | 83.0 ± 22.8 |
|  | 30 | 45.4 ± 7.2 | 104.2 ± 40.3 | 79.8 ± 37.3 |
| Ex. 49 | 10 | 78.8 ± 23.2 | 90.8 ± 28.2* | 43.2 ± 12.9* |
|  | 30 | 45.8 ± 6.1 | 86.4 ± 11.1* | 50.0 ± 11.9* |

Effective Number (t-test): * $p < 0.05$ (Compared to Solvent Control)

Referring to Table 5, the compounds of Examples 27 and 49, when administered to mice, exhibited superior effect of decreasing blood triglyceride concentration. That is, compared to the solvent control which was administered with carboxy methyl cellulose then administered with corn oil, and showed approximately 4.3-fold increase of the triglyceride concentration after 2 hr and approximately 2.4-fold increase of the triglyceride concentration after 4 hr of administration, the mice administered with 30 mg/kg of the compounds of Examples 27 and 49 and then administered with corn oil showed approximately 1.9- and 2.3-fold increase of triglyceride concentration after 2 hr, and approximately 1.1- and 1.8-fold increase of triglyceride concentration after 4 hr of administration. Further, the mice administered with 10 mg/kg of the compound according to the present invention also showed lower increasing rate of triglyceride concentration, compared with the mice administered with 30 mg/kg. Based on the findings, it was confirmed that the compound according to the present invention inhibits triglyceride concentration in mice and that such effect is capacity-dependent.

Therefore, according to the present invention, the indole derivative effectively inhibits biosynthesis of triglycerides within the cells, and thus can be advantageously used as a pharmaceutical composition for the prevention or treatment of metabolic diseases.

Experimental Example 5

Acute Toxicity Assay

In order to investigate acute toxicity of the indole derivatives according to the present invention, mice (20±5 g, Central Lab. Animal Inc.) and rats (235±10 g, Central Lab. Animal Inc.) were used for the acute toxicity assay of compound 1.

A total of four groups of 10 ICR mice were orally administered with compound 1 according to the present invention by the dose of 100, 250 mg/kg, respectively. The observation on toxicity over the following two weeks revealed no death in any of the four groups, nor did the groups show any specific difference on the outside.

Accordingly, since the indole derivative according to the present invention has no biological toxicity, the indole derivative can be advantageously used for a pharmaceutical composition for preventing or treating metabolic diseases.

Hereinbelow, examples of the formulations using the composition containing indole derivative of Formula 1 according to the present invention will be explained.

Preparation Example 1

Preparation of Powder

| | |
|---|---|
| Indole derivative of Formula 1 | 2 g |
| Lactose | 1 g |

After the above ingredients were mixed and charged into sachet, the powder preparation was made.

Preparation Example 2

Preparation of Tablets

| | |
|---|---|
| Indole derivatives of Formula 1 | 100 mg |
| Cornstarch | 100 mg |
| Lactose | 100 mg |
| Magnesium stearate | 2 mg |

The above ingredients were mixed and tabulated into tablet according to general tablet manufacturing method.

Preparation Example 3

Preparation of Capsules

| | |
|---|---|
| Indole derivatives of Formula 1 | 100 mg |
| Cornstarch | 100 mg |
| Lactose | 100 mg |
| Magnesium stearate | 2 mg |

The above ingredients were mixed and charged in gelatin capsule according to general capsule manufacturing method.

Preparation Example 4

Preparation of Injection

| | |
|---|---|
| Indole derivative of Formula 1 | 10 µg/ml |
| Dilute hydrochloric acid | until pH 3.5 |
| Sodium chloride BP for Injection | Max. 1 ml |

After dissolving the compound of Formula 1 according to the present invention to appropriate volume of sodium chloride BP for injection, and regulating the pH of the produced solution to pH 3.5 using dilute hydrochloric acid, the volume was adjusted using sodium chloride BP for injection and sufficiently mixed. The injection was prepared after charging the solution in 5 ml type I ampoule of transparent glass, and sterilizing in autoclave at 120° C. for 15 min or longer.

Preparation Example 5

Preparation of Health Food

| | |
|---|---|
| Indole derivative of Formula 1 | 500 ng |
| Vitamin compound | suitable amount |
| Vitamin A acetate | <70 µg |
| Vitamin E | 1.0 mg |
| Vitamin | 0.13 mg |
| Vitamin B2 | 0.15 mg |
| Vitamin B6 | 0.5 mg |
| Vitamin B12 | 0.2 µg |
| Vitamin C | 10 mg |
| Biotin | 10 µg |
| Nicotinic acid amide | 1.7 mg |
| Folic acid | 50 mg |
| Calcium pantothenate | 0.5 mg |
| Mineral mixture | suitable amount |
| Ferrous sulfate | 1.75 mg |
| Zinc oxide | 0.82 mg |
| Magnesium carbonate | 25.3 mg |
| Mono potassium phosphate | 15 mg |
| Dicalcium phosphate | 55 mg |
| Potassium citrate | 90 mg |
| Potassium carbonate | 100 mg |
| Magnesium chloride | 24.8 mg |

Although the vitamins and mineral mixtures were so selected and also adjusted at such a ratio to be relatively suitable for the purpose of health food, the mixing ratio may be arbitrarily varied and it is also possible to mix the above-mentioned ingredient to prepare granules according to general health food manufacturing method and then use the same for the preparation of health food composition according to general method.

Preparation Example 6

Preparation of Health Beverage

| | |
|---|---|
| Indole derivative of Formula 1 | 500 ng |
| Citric acid | 1000 mg |
| Oligosaccharide | 100 g |
| Asian apricot concentration | 2 g |
| Taurine | 1 g |
| Whole volume with distilled water | 900 ml |

The above ingredients were mixed according to general health beverage manufacturing method and stirred and heated for approximately 1 hr at 85° C., filtered and received in sterilized receptor, sealed and sterilized, refrigerated and used for the manufacture of health beverage composition.

Although the above-mentioned ingredients were selected and mixed at ratio for the purpose of relatively favorite beverages, the mixing ratio may arbitrarily varied depending on locations or cultural preferences such as the consumer groups, countries, or purposes of consumption.

It will be appreciated by those skilled in the art that modifications can be made to the embodiments disclosed and remain within the inventive concept. Therefore, this disclosure is not limited to the specific embodiments disclosed, but is intended to cover changes within the scope and spirit of the claims.

Various references are cited throughout this specification, each of which is incorporated herein by reference in its entirety.

The invention claimed is:

1. An indole derivative represented by Formula 1 below or a pharmaceutically acceptable salt thereof:

[Formula 1]

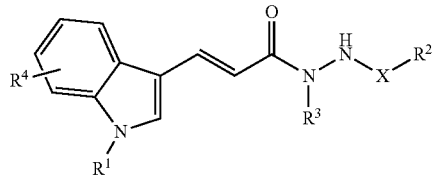

where, $R^1$ is —H, $C_{1-10}$ linear or branched alkyl group, $C_{2-10}$ linear or branched alkenyl group, $C_{3-12}$ cycloalkyl group, $C_{3-12}$ cycloalkyl $C_{1-5}$ alkyl group, $C_{5-12}$ aryl group, $C_{1-5}$ aryl $C_{1-5}$ alkyl group, $C_{5-12}$ aryl carbonyl group, $C_{1-10}$ linear or branched alkyl carbonyl group or $C_{1-10}$ linear or branched alkoxy carbonyl group;

$R^2$ is $C_{5-12}$ aryl group or $C_{5-12}$ heteroaryl group including one or more of N, O and S in a ring, wherein the aryl group or heteroaryl group is non-substituted or substituted with —OH, $C_{1-10}$ linear or branched alkyl group, halogen or

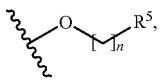

$R^5$ is —H, —OH, —NH$_2$, carboxyl group, amino carbonyl group, $C_{1-10}$ linear or branched alkyl group, $C_{1-5}$ linear or branched alkoxy group, $C_{1-10}$ linear or branched alkoxy carbonyl group or $C_{5-12}$ heterocycloalkyl group including one or more of N, O and S in a ring, n is an integer between 0-5;

$R^3$ is —H or $C_{1-5}$ linear or branched alkyl group;

$R^4$ is —H, $C_{1-5}$ linear or branched alkyl group or halogen;

X is carbonyl group or sulfonyl group; and

===== is single or double bond.

2. The indole derivative according to claim 1, wherein $R^1$ is —H, $C_{1-5}$ linear or branched alkyl group, $C_{2-6}$ linear or branched alkenyl group, $C_{3-6}$ cycloalkyl group, $C_{3-6}$ cycloalkyl $C_{1-3}$ alkyl group, $C_{5-7}$ aryl group, $C_{5-7}$ aryl $C_{1-3}$ alkyl group, $C_{5-7}$ arylcarbonyl group, $C_{1-6}$ linear or branched alkylcarbonyl group or $C_{1-5}$ linear or branched alkoxycarbonyl group;

$R^2$ is $C_{5-7}$ aryl group or $C_{5-7}$ heteroaryl group including one or more of N, O and S in a ring, in which the aryl group or heteroaryl group is non-substituted or substituted with —OH, $C_{1-5}$ linear or branched alkyl group, halogen or

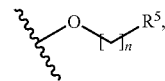

$R^5$ is —H, —OH, —NH$_2$, carboxyl group, aminocarbonyl group, $C_{1-5}$ linear or branched alkyl group, $C_{1-5}$ linear or branched alkoxy group, $C_{1-5}$ linear or branched alkoxycarbonyl group or $C_{5-7}$ heterocycloalkyl group including one or more of N, O and S in a ring, n is integer between 0-3;

$R^3$ is —H or $C_{1-10}$ linear or branched alkyl group;

$R^4$ is —H, $C_{1-10}$ linear or branched alkyl group or halogen;

X is carbonyl group or sulfonyl group; and

===== is single or double bond.

3. The indole derivative according to claim 1, wherein $R^1$ is —H, —CH$_3$,

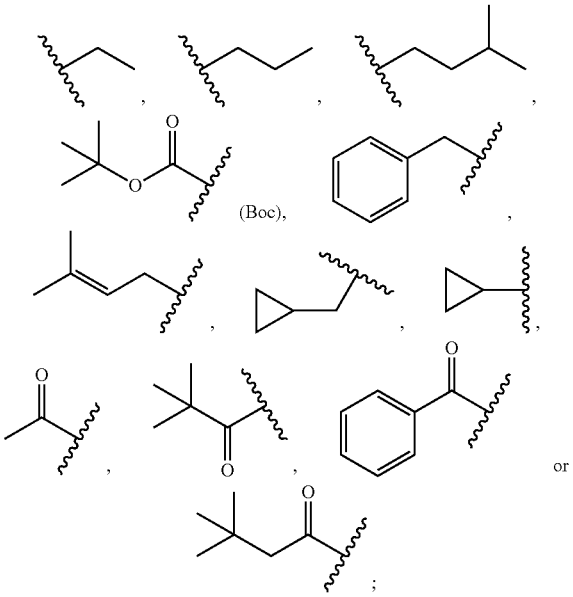

$R^3$ is independently —H or isopropyl;

$R^4$ is —H, —CH$_3$, isopropyl or fluoro;

X is carbonyl group or sulfonyl group; and

===== is single or double bond.

4. The indole derivative according to claim 1, wherein the indole derivative is selected from the group consisting of:

1) (E)-tert-butyl 3-(3-(2-benzoyl-1-isopropylhydrazinyl)-3-oxoprop-1-enyl)-1H-indole-1-carboxylate;

2) (E)-tert-butyl 3-(3-(1-isopropyl-2-picolinoylhydrazinyl)-3-oxoprop-1-enyl)-1H-indole-1-carboxylate;

3) (E)-tert-butyl 3-(3-(1-isopropyl-2-nicotinoylhydrazinyl)-3-oxoprop-1-enyl)-1H-indole-1-carboxylate;

4) (E)-tert-butyl 3-(3-(2-(3-hydroxybenzoyl)-1-isopropylhydrazinyl)-3-oxoprop-1-enyl)-1H-indole-1-carboxylate;

5) (E)-tert-butyl 3-(3-(2-(4-hydroxybenzoyl)-1-isopropylhydrazinyl)-3-oxoprop-1-enyl)-1H-indole-1-carboxylate;

6) (E)-tert-butyl 3-(3-(1-isopropyl-2-(3-methoxybenzoyl)hydrazinyl)-3-oxoprop-1-enyl)-1H-indole-1-carboxylate;

7) (E)-tert-butyl 3-(3-(1-isopropyl-2-(4-methoxybenzoyl) hydrazinyl)-3-oxoprop-1-enyl)-1H-indole-1-carboxylate;
8) (E)-tert-butyl 3-(3-(1-isopropyl-2-(3-(2-morpholinoethoxy)benzoyl)hydrazinyl)-3-oxoprop-1-enyl)-1H-indole-1-carboxylate;
9) (E)-tert-butyl 3-(3-(1-isopropyl-2-(4-(2-morpholinoethoxy)benzoyl)hydrazinyl)-3-oxoprop-1-enyl)-1H-indole-1-carboxylate;
10) (E)-tert-butyl 3-(3-(1-isopropyl-2-(3-(2-methoxyethoxy)benzoyl)hydrazinyl)-3-oxoprop-1-enyl)-1H-indole-1-carboxylate;
11) (E)-tert-butyl 3-(3-(1-isopropyl-2-(4-(2-methoxyethoxy)benzoyl)hydrazinyl)-3-oxoprop-1-enyl)-1H-indole-1-carboxylate;
12) (E)-tert-butyl 3-(3-(2-(3-bromobenzoyl)-1isopropylhydrazinyl)-3-oxoprop-1-enyl)-1H-indole-1-carboxylate;
13) (E)-tert-butyl 3-(3-(2-(4-bromobenzoyl)-1-isopropylhydrazinyl)-3-oxoprop-1-enyl)-1H-indole-1-carboxylate;
14) (E)-tert-butyl 3-(3-(2-(4-chlorobenzoyl)-1-isopropylhydrazinyl)-3-oxoprop-1-enyl)-1H-indole-1-carboxylate;
15) (E)-tert-butyl 3-(3-(2-(3-fluorobenzoyl)-1-isopropylhydrazinyl)-3-oxoprop-1-enyl)-1H-indole-1-carboxylate;
16) (E)-tert-butyl 3-(3-(2-benzoylhydrazinyl)-3-oxoprop-1-enyl)-1H-indole-1-carboxylate;
17) (E)-tert-butyl 3-(3-oxo-3-(2-(phenylsulfonyl)hydrazinyl)prop-1-enyl)-1H-indole-1-carboxylate;
18) (E)-tert-butyl 3-(3-(1-isopropyl-2-(3-(2-methoxy-2-oxoethoxy)benzoyl)hydrazinyl)-3-oxoprop-1-enyl)-1H-indole-1-carboxylate;
19) (E)-2-(3-(2-(3-(1-(tert-butoxycarbonyl)-1H-indol-3-yl)acryloyl)-2-isopropylhydrazinecarbonyl)phenoxy) acetic acid;
20) (E)-tert-butyl 3-(3-(2-(3-(2-amino-2-oxoethoxy)benzoyl)-1-isopropylhydrazinyl)-3-oxoprop-1-enyl)-1H-indole-1-carboxylate;
21) N'-(3-(1-benzyl-1H-indol-3-yl)propanoyl)-N'-isopropylbenzohydrazide;
22) (E)-N'-(3-(1H-indol-3-yl)acryloyl)-N'-isopropylbenzohydrazide;
23) N'-(3-(1H-indol-3-yl)propanoyl)-N'-isopropylbenzohydrazide;
24) tert-butyl 3-(3-(2-benzoyl-1-isopropylhydrazinyl)-3-oxopropyl)-1H-indole-1-carboxylate;
25) (E)-N'-isopropyl-N'-(3-(1-methyl-1H-indol-3-yl) acryloyl)benzohydrazide);
26) (E)-N'-(3-(1-benzyl-1H-indol-3-yl)acryloyl)-N'-isopropylbenzohydrazide;
27) (E)-N'-isopropyl-N'-(3-(1-(3-methylbut-2-enyl)-1H-indol-3-yl)acryloyl)benzohydrazide;
28) (E)-N'-(3-(1-(cyclopropylmethyl)-1H-indol-3-yl) acryloyl)-N'-isopropylbenzohydrazide;
29) (E)-N'-(3-(1-cyclopropyl-1H-indol-3-yl)acryloyl)-N'-isopropylbenzohydrazide;
30) (E)-N'-(3-(1-acetyl-1H-indol-3-yl)acryloyl)-N'-isopropylbenzohydrazide;
31) (E)-N'-isopropyl-N'-(3-(1-pivaloyl-1H-indol-3-yl) acryloyl)benzohydrazide;
32) (E)-N'-(3-(1-benzoyl-1H-indol-3-yl)acryloyl)-N'-isopropylbenzohydrazide;
33) (E)-N'-(3-(1-(3,3-dimethylbutanoyl)-1H-indol-3-yl) acryloyl)-N'-isopropylbenzohydrazide;
34) (E)-3-fluoro-N'-isopropyl-N'-(3-(1-(3-methylbut-2-enyl)-1H-indol-3-yl)acryloyl)benzohydrazide);
35) (E)-tert-butyl 3-(3-(2-(3-fluorobenzoyl)-1-isopropylhydrazinyl)-3-oxoprop-1-enyl)-5-methyl-1H-indole-1-carboxylate;
36) (E)-tert-butyl 3-(3-(2-(3-fluorobenzoyl)-1-isopropylhydrazinyl)-3-oxoprop-1-enyl)-6-isopropyl-1H-indole-1-carboxylate;
37) (E)-tert-butyl 3-(3-(2-(3-fluorobenzoyl)-1-isopropylhydrazinyl)-3-oxoprop-1-enyl)-6-methyl-1H-indole-1-carboxylate;
38) (E)-tert-butyl 6-fluoro-3-(3-(2-(3-fluorobenzoyl)-1-isopropylhydrazinyl)-3-oxoprop-1-enyl)-1H-indole-1-carboxylate;
39) (E)-3-fluoro-N'-(3-(1-isopentyl-1H-indol-3yl) acryloyl)-N'-isopropylbenzohydrazide;
40) (E)-3-fluoro-N'-isopropyl-N'-(3-(1-methyl-1H-indol-3-yl)acryloyl)benzohydrazide;
41) (E)-N'-(3-(1-ethyl-1H-indol-3-yl)acryloyl)-3-fluoro-N'-isopropylbenzohydrazide;
42) (E)-3-fluoro-N'-isopropyl-N'-(3-(1-propyl-1H-indol-3-yl)acryloyl)benzohydrazide;
43) (E)-tert-butyl 3-(3-(2-isonicotinoyl-1-isopropylhydrazinyl)-3-oxoprop-1-enyl)-1H-indole-1-carboxylate;
44) (E)-tert-butyl 3-(3-(2-(4-fluorobenzoyl)-1-isopropylhydrazinyl)-3-oxoprop-1-enyl)-1H-indole-1-carboxylate;
45) (E)-tert-butyl 3-(3-(2-(3-chlorobenzoyl)-1-isopropylhydrazinyl)-3-oxoprop-1-enyl)-1H-indole-1-carboxylate;
46) (E)-4-fluoro-N'-(3-(1-isopentyl-1H-indol-3-yl)acryloyl)-N'-isopropylbenzohydrazide;
47) (E)-tert-butyl 3-(3-(1-isopropyl-2-(3-methylbenzoyl) hydrazinyl)-3-oxoprop-1-enyl)-1H-indole-1-carboxylate;
48) (E)-tert-butyl 3-(3-(1-isopropyl-2-(4-methylbenzoyl) hydrazinyl)-3-oxoprop-1-enyl)-1H-indole-1-carboxylate;
49) (E)-4-fluoro-N'-isopropyl-N'-(3-(1-(3-methylbut-2-enyl)-1H-indol-3-yl)acryloyl)benzohydrazide;
50) (E)-N'-isopropyl-3-methyl-N'-(3-(1-(3-methylbut-2-enyl)-1H-indol-3-yl)acryloyl)benzohydrazide; and
51) (E)-N'-isopropyl-4-methyl-N'-(3-(1-(3-methylbut-2-enyl)-1H-indol-3-yl)acryloyl)benzohydrazide.

5. A method for preparing the indole derivatives according to claim 1, comprising a step of obtaining compound represented by Formula 1a, by dehydration reacting indole derivative represented by Formula 2 with compound represented by Formula 3, as indicated by Reaction Formula 1 below:

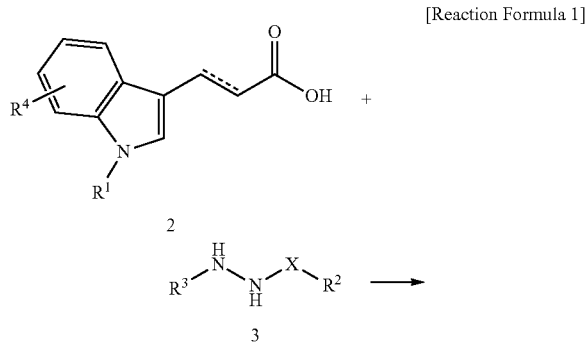

[Reaction Formula 1]

-continued

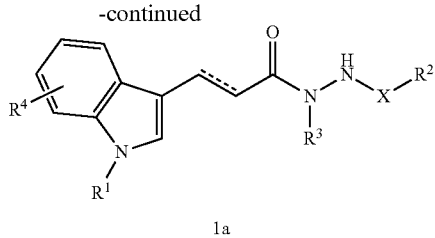

1a where, $R^1$, $R^2$, $R^3$, $R^4$, X and ===== are as defined in Formula 1 as set forth in claim 1; and Formula 1a is included in Formula 1.

6. A method for preparing the indole derivative of claim 1, comprising, as indicated by Reaction Formula 2 below:

adding iodomethane to (E)-3-(1H-indol-3-yl)acrylic acid for the purpose of introducing protecting group, for methylation which gives (E)-methyl 3-(1H-indol-3-yl) acrylate (step 1);

obtaining compound 4a introduced with $R^6$ substituent, by alkylation of nitrogen in (E)-methyl 3-(1H-indol-3-yl) acrylate obtained at step 1 (step 2);

obtaining compound 4b by adding sodium hydroxide to the compound of 4a obtained at step 2 for de-protecting purpose (step 3); and obtaining compound 1b by adding N'-isopropylbenzohydrazide to the compound 4b obtained at step 3 for dehydration purpose (step 4):

-continued

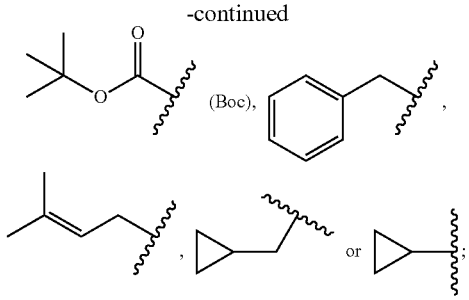

and

Formula 1b is included in Formula 1.

7. A method for preparing the indole derivative according to claim 1, the preparation method comprising following steps, as indicated by Reaction Formula 3 below:

obtaining (E)-N'-(3-(1H-indol-3-yl)acryloyl)-N'-isopropylbenzohydrazide by adding N'-isopropylbenzohydrazide to (E)-3-(1H-indol-3-yl)acrylic acid for dehydration reaction (step 1); and obtaining compound 1c introduced with $R^7$ substituent, by alkylation of nitrogen in the (E)-N'-(3-(1H-indol-3-yl) acryloyl)-N'-isopropyl benzohydrazide obtained at step 1 (step 2):

[Reaction Formula 2]

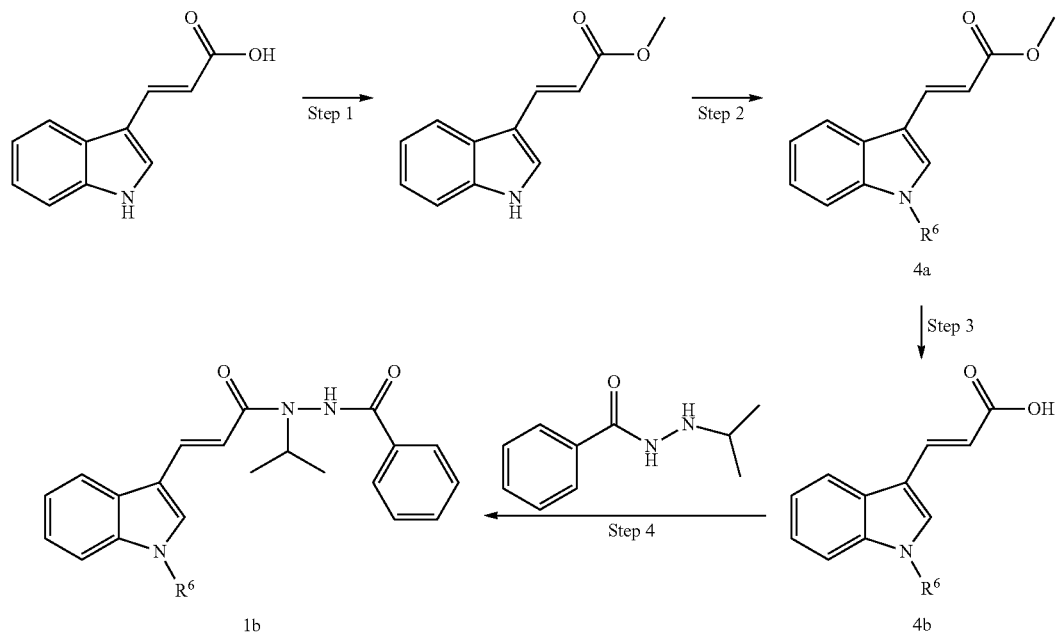

where $R^6$ is —$CH_3$,

[Reaction Formula 3]

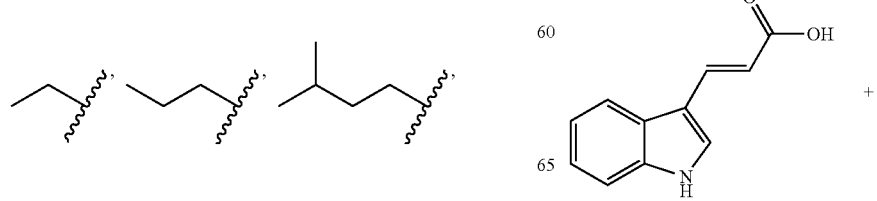

-continued

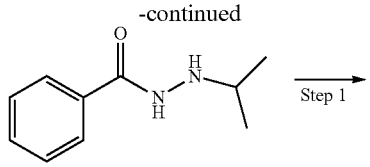
Step 1

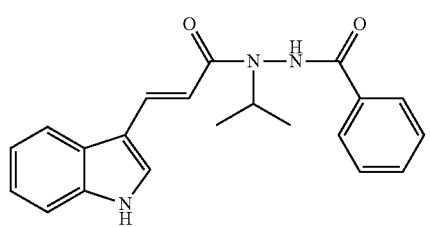

Step 2

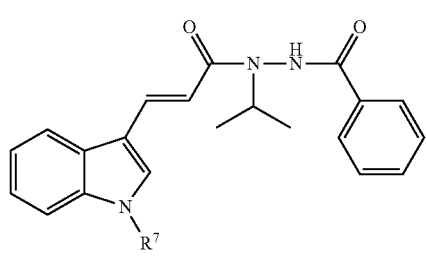

1c where, R⁷ is

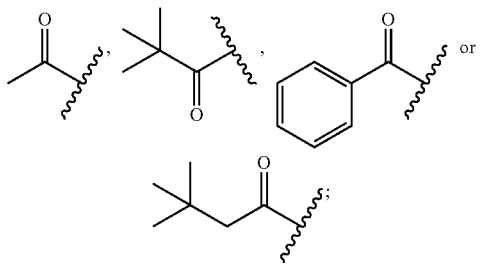

and
Formula 1c is included in Formula 1.

8. A method for preparing the indole derivative according to claim 1, comprising following steps, as indicated by Reaction Formula 4 below:
preparing compound represented by Formula 6 by allowing the compound represented by Formula 5 to react with ethyl(triphenylphosphoranylidene)acetate (step 1);
preparing compound represented by Formula 7 by adding sodium hydroxide to the compound of Formula 6 prepared at step 1 for deprotecting purpose (step 2);
preparing compound represented by Formula 4c with protected amino group, by allowing amino group of compound represented by Formula 7 prepared at step 2 to react with di-tert-buthyl dicarbonate (step 3); and
preparing compound represented by Formula 1d by dehydrating the compound of Formula 4c prepared at step 3 with the compound represented by Formula 3a (step 4):

[Reaction Formula 4]

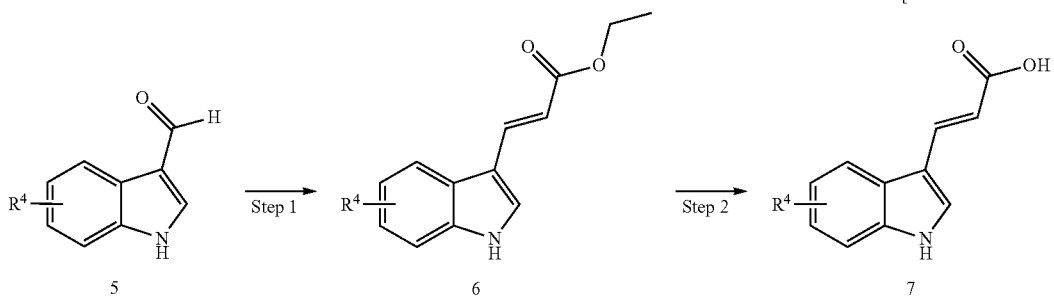

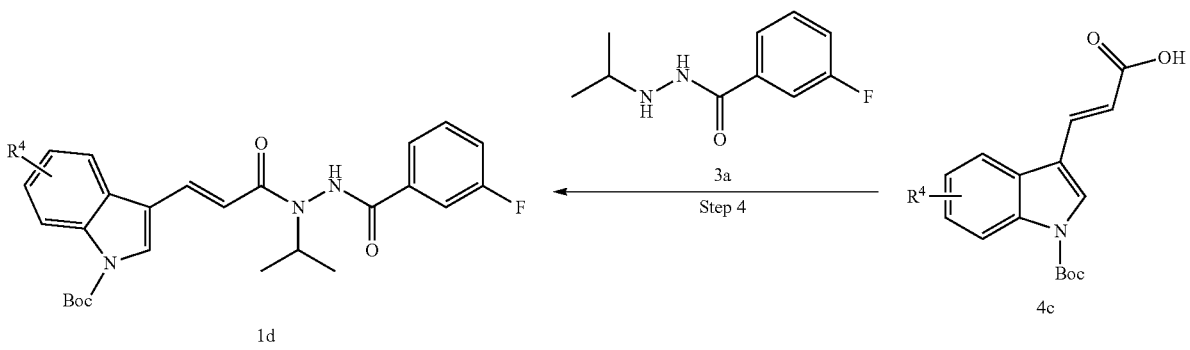

where, $R^4$ is as defined in Formula 1;
Boc is

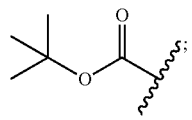

and

Formula 1d is included in Formula 1.

9. A composition comprising the indole derivative represented by Formula 1 according to claim 1 as active ingredient.

10. A method for treating metabolic disease in a patient in need thereof comprising administering to a patient in need thereof an amount of the indole derivative according to claim 1 effective to treat said metabolic disease, wherein said metabolic disease is selected from the group consisting of obesity, type 2 diabetes, hyperlipidemia and fatty liver.

11. A diacylglycerol acyltransferase (DGAT) activity inhibitor, comprising the indole derivative represented by Formula 1 according to claim 1 as active ingredient.

\* \* \* \* \*